(12) United States Patent
Hadley et al.

(10) Patent No.: US 7,429,579 B2
(45) Date of Patent: Sep. 30, 2008

(54) TETRAHYDROBENZAZEPINE DERIVATIVES USEFUL AS MODULATORS OF DOPAMINE D3 RECEPTORS (ANTIPSYCHOTIC AGENTS)

(75) Inventors: Michael Stewart Hadley, Harlow (GB); Andrew Lightfoot, Harlow (GB); Gregor James MacDonald, Harlow (GB); Geoffrey Stemp, Stevenage (GB)

(73) Assignee: SmithKline Beecham, PLC, Brentford, Middlesex (GB)

( * ) Notice: Subject to any disclaimer, the term of this patent is extended or adjusted under 35 U.S.C. 154(b) by 346 days.

(21) Appl. No.: 10/416,377

(22) PCT Filed: Nov. 12, 2001

(86) PCT No.: PCT/EP01/13140

§ 371 (c)(1),
(2), (4) Date: Nov. 11, 2003

(87) PCT Pub. No.: WO02/40471

PCT Pub. Date: May 23, 2002

(65) Prior Publication Data

US 2004/0171606 A1   Sep. 2, 2004

(30) Foreign Application Priority Data

Nov. 14, 2000 (GB) ................. 0027784.8
Dec. 20, 2000 (GB) ................. 0031082.1

(51) Int. Cl.
*A61P 25/18* (2006.01)
*A61K 31/55* (2006.01)
*C07D 223/16* (2006.01)

(52) U.S. Cl. .................. 514/217.01; 540/594

(58) Field of Classification Search ............ 514/217.01; 540/594
See application file for complete search history.

(56) References Cited

U.S. PATENT DOCUMENTS

| 4,233,217 A | 11/1980 | Shetty | 260/239 BB |
|---|---|---|---|
| 4,352,754 A | 10/1982 | Weinstock | 260/330.3 |
| 4,824,839 A * | 4/1989 | Bondinell et al. | 514/217.01 |
| 6,602,867 B1 | 8/2003 | Starck et al. | 514/217.07 |

FOREIGN PATENT DOCUMENTS

| WO | WO 00 21951 | 4/2000 |
|---|---|---|
| WO | WO 00 42036 | 7/2000 |

OTHER PUBLICATIONS

Austin, N. E. et al., "Novel 2,3,4,5-tetrahydro-1H-3-benzazepines with high affinity and selectivity for the dopamine D3 receptor"., Bioorganic & Medicinal Chemistry Letters, Oxford, GB, Vo. 10., No. 22, Nov. 20, 2000 (pp. 2553-2555, XP004224262.

* cited by examiner

*Primary Examiner*—Brenda L Coleman
(74) *Attorney, Agent, or Firm*—James M. Kanagy; Stephen Venetianer; Charles M. Kinzig

(57) ABSTRACT

The invention provides compounds of formula (I): wherein: $R^2$ and $R^3$ independently represent various substituents; $R^1$ and $R^4$ independently represent H, F, Cl, Br, $C_{1-2}$alkyl, $C_1$alkoxy, OH, CN, or $NO_2$; B represents a sulfur atom or a —$CH_2$-group; t represents 3 or 4; and A represents an optionally substituted 5- or 6-membered aromatic heterocyclic ring, or an optionally substituted bicyclic heterocyclic ring system in which at least the ring bound to the group B in Formula (I) is aromatic; or a salt thereof. Preferably, A is selected from one of the groups (i), (ii) or (iii): wherein $X^1$ and $X^2$ are independently N or $CR^8$, and $X^3$ is $NR^8$, O or S; $Y^1$ and $Y^3$ are independently N or $CR^9$, and $Y^2$ is $NR^9$, O or S; $Z^1$ is $NR^{10}$, O or S, and $Z^2$ and $Z^3$ are independently N or $CR^{10}$; $R^8$, $R^9$, and $R^{10}$ are as herein defined, and $R^7$ is H, a halogen atom, OH, cyano, nitro, $C_{1-4}$alkyl, $C_{1-4}$alkoxy, $C_{1-4}$alkylenedioxy, $C_{1-4}$alkanoyl, or $C_{1-4}$alkylsulfonyl, an optionally substituted 3-, 4-, 5- or 6-membered cycloalkyl ring, or a group of the formula (a), (b), (c) or (d) as defined by the formulas (a), (b), (c) or (d). The compounds are modulators of dopamine $D_3$ receptors and have potential in the treatment of psychotic conditions (e.g. schizophrenia) or substance abuse.

8 Claims, No Drawings

TETRAHYDROBENZAZEPINE DERIVATIVES USEFUL AS MODULATORS OF DOPAMINE D3 RECEPTORS (ANTIPSYCHOTIC AGENTS)

This application is a national stage entry under 35 U.S.C. § 371 of PCT/EP01/13140, filed Nov. 12, 2001.

The present invention relates to novel tetrahydrobenzazepine derivatives, processes for their preparation, intermediates used in these processes, pharmaceutical compositions containing them and their use in therapy, as modulators of dopamine $D_3$ receptors, in particular as antipsychotic agents.

BACKGROUND TO THE INVENTION

U.S. Pat. No. 5,294,621 describes tetrahydropyridine derivatives of the formula:

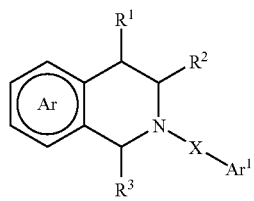

wherein

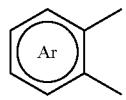

is an optionally substituted thienyl or optionally substituted phenyl ring; $R^1$, $R^2$ and $R^3$ are each inter alia hydrogen; X is inter alia $(CH_2)mNR^7CO$; m is 2-4; and $Ar^1$ is an optionally substituted heterocyclic ring or an optionally substituted phenyl ring. The compounds are said to be useful as antiarrhythmic agents.

EPA 431,580 describes compounds which are said to be dopaminergic agents useful as antipsychotics, antihypertensives, etc. WO 95/10513 describes benzothiophene derivatives and related compounds as estrogen agonists.

EP 0 494 623 A1 (Laboratoires Glaxo) discloses acridine derivatives of the following general formula:

where n is 1 or 2. There are many examples of the chain —A—B—$CH_2$— including —$S(CH_2)_3$—. The preferred compounds are tetrahydroisoquinoline acridines. These compounds are disclosed as being capable of sensitizing multi-drug-resistant cancer cells to chemotherapeutic agents. There appears to be no disclosure that these compounds have affinity for dopamine $D_3$ receptors or could be used in the treatment of psychotic conditions.

WO 93/03025 (EP 0 596 120), WO 93/13105 (EP 0 596 125) and JP 07070135-A (all Yoshitomi Pharmaceutical Industries) disclose antipsychotic thiophene and condensed thiophene compounds. WO 93/20099 (Ferring) discloses CCK and/or gastrin receptor ligands to treat ulcers, anxiety, psychoses, etc. WO 98/07421 (Ishihara Sangyo Kaisha) discloses cycloalkyl-isoquinolinone and isoindolinone compounds as inhibitors of amino-peptidase N-enzyme.

WO 97/43262, WO 98/06699, WO 98/49145, WO 98/50363, WO 98/50364, WO98/51671, WO 99/64412, WO 00/24717 (all SmithKline Beecham plc), N. E. Austin et al., *Bioorg. Med. Chem. Lett.*, 1999, 9(2), 179-184, G. Stemp et al., *J. Med. Chem.*, 2000, 43(9), 1878-1885, C. Reavill et al., *J. Pharmacol. Exp. Ther.*, 2000, 294(3), 1154-1165, and C. R. Ashby et al., *J. Pharmacol. Exp. Ther.*, 2000, 294(3), 1166-1174, disclose tetrahydroisoquinoline derivatives having affinity for the dopamine $D_3$ receptor. WO 00/21950 discloses isoindoles having similar activity. Other D3 modulators are disclosed in WO 96/30333, WO 97/47602, WO 94/03426, WO 94/24129, WO 95/00508, WO 95/16674, WO 95/21165, WO 95/22542, WO 97/00243 (all SmithKline Beecham) and in K.Y. Avenell, et al., *Bioorg. Med. Chem. Lett.*, 1999, 9(18), 2715-2720, K. Y. Avenell et al., *Bioorg. Med. Chem. Lett.*, 1998, 8(20), 2859-2864, I. Boyfield et al., *Bioorg. Med. Chem. Lett.*, 1997, 7(15), 1995-1998, D. Bolton et al., *Bioorg. Med. Chem. Lett.*, 1997, 7(4), 485-488 and I. Boyfield et al., *Bioorg. Med. Chem. Lett.*, 1997, 7(3), 327-330.

Other publications disclosing compounds allegedly having affinity for dopamine receptor(s) include: JP 10287631 A2 and EP 773223 A1 (Adir), JP 09291034 A2 (Yoshitomi), WO 97/38989, WO 97/34889, WO 97/31916, U.S. Pat. No. 5,633,376, WO 96/25411, WO 96/16040, and WO 96/10018 (all Neurogen), WO 97/34889 and U.S. Pat. No. 5,414,010 (Warner-Lambert), WO 95/29891 and WO 95/08533 (Yamanouchi), and U.S. Pat. No. 5,478,934 (Jun Yuan).

WO 00/42036 (BASF) discloses a series of 1,2,4-triazoles linked by various linking groups to tetrahydroisoquinolines or isoindoles, which are disclosed as having affinity for the dopamine $D_3$ receptor. Other alleged $D_3$ modulators are dis-

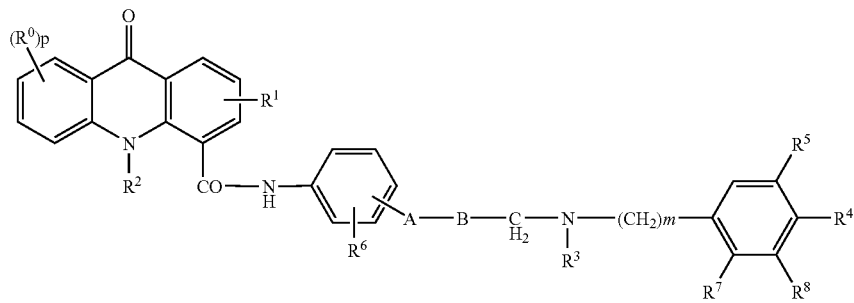

where A is O, S, a bond or $CH_2NR^9$; B represents an optionally substituted $C_{1-4}$alkylene chain, m is 1 or 2; $R^3$ is H or alkyl and $R^7$ is H or $R^3$ and $R^7$ together from a group $(CH_2)_n$ closed in WO 00/42037, WO 00/42038, DE 19728996 A1, WO 96/02519, WO 97/25324, WO 96/02249, WO 96/02246, WO 96/02520 and DE 4425146 (all BASF).

WO 00/21951 (SmithKline Beecham) discloses tetrahydrobenzazepine compounds of the following formula:

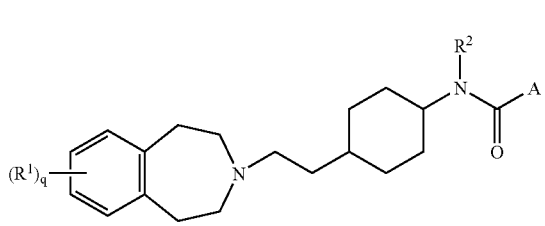

wherein $R^1$ and $R^2$ are independently H or various substituents; q is 1 or 2; and A represents a group of the formula (a), (b), (c) or (d):

—Ar  (a)

—$Ar^1$—Y—$Ar^2$  (b)

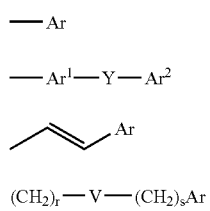 (c)

$(CH_2)_r$—V—$(CH_2)_s$Ar  (d)

wherein Ar represents an optionally substituted phenyl ring or an optionally substituted 5- or 6-membered aromatic heterocyclic ring; or an optionally substituted bicyclic ring system; $Ar^1$ and $Ar^2$ each independently represent an optionally substituted phenyl ring or an optionally substituted 5- or 6-membered aromatic heterocyclic ring; Y represents a bond or various linking groups; r and s independently represent an integer from zero to 3 such that the sum of r and s is equal to an integer from 1 to 4; and V is a bond, O or S. These compounds were found to exhibit affinity for dopamine $D_3$ receptor and are disclosed as being useful in the treatment of psychotic conditions, e.g. schizophrenia.

N-(Cyclohexylethyl)-tetrahydrobenzazepine compounds having affinity at the $D_3$ receptor are also disclosed in N. E. Austin et al., *Bioorg. Med. Chem. Lett.*, 2000, 10, 2553-2555.

WO 01/23357 (Amgen) discloses benzazepine derivatives useful in the treatment of diseases, conditions or disorders mediated by integrin derivatives, for example atherosclerosis, restenosis, inflammation, cancer, osteoporosis and the like. There appears to be no disclosure that these compounds have affinity for dopamine $D_3$ receptors or could be used in the treatment of psychotic conditions.

SUMMARY OF THE INVENTION

We have now found a novel class of tetrahydrobenzazepine derivatives which have affinity for dopamine receptors, in particular the dopamine $D_3$ receptor. These derivatives thus have potential in the treatment of conditions wherein modulation, especially antagonism/inhibition, of the $D_3$ receptor is beneficial, e.g. as antipsychotic agents.

In a first aspect the present invention provides a compound of formula (I):

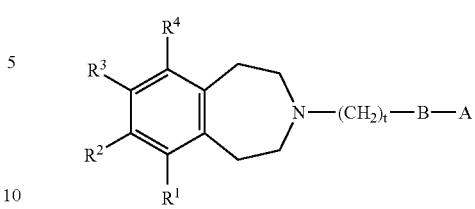

Formula (I)

wherein:

$R^2$ and $R^3$ independently represent:

a hydrogen or halogen atom; a hydroxy, cyano, nitro, oxime, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group;

a group $R^5OCO(CH_2)_p$, $R^5CON(R^6)(CH_2)_p$, $R^5R^6NCO(CH_2)_p$ or $R^5R^6NSO_2(CH_2)_p$, in which p represents zero or an integer from 1 to 4, and (for all four groups) each of $R^5$ and $R^6$ independently represents a hydrogen atom or a $C_{1-4}$alkyl group, or (in groups $R^5CON(R^6)(CH_2)_p$, $R^5R^6NCO(CH_2)_p$ and $R^5R^6NSO_2(CH_2)_p$) $R^5CONR^6$ or $R^5R^6N$ together form a 4-,5-,6- or 7-membered azacyclic group optionally containing one additional O, N or S atom in the azacycle and having 3-8 carbon atoms (including the carbon atoms contained in any optional substituent(s) of the azacycle); or a group $Ar^3$—Z, wherein $Ar^3$ represents an optionally substituted phenyl ring or an optionally substituted 5- or 6-membered aromatic heterocyclic ring and Z represents a bond, O, S, $SO_2$ or $CH_2$;

$R^1$ and $R^4$ independently represent H, F, Cl, Br, $C_{1-2}$alkyl, $C_1$alkoxy, OH, CN, or $NO_2$;

B represents a sulfur atom or a —$CH_2$— group;

t represents 3 or 4; and

A represents an optionally substituted 5- or 6-membered aromatic heterocyclic ring, or an optionally substituted bicyclic heterocyclic ring system in which at least the ring bound to the group B in Formula (I) is aromatic;

or a salt thereof.

In the compounds of formula (I) above an "alkyl" group or moiety may be straight or branched, and includes alkyl groups with one, two, three or more fluorine substituents. Alkyl groups which may be employed include methyl, trifluoromethyl, ethyl, pentafluoroethyl, n-propyl, n-butyl, n-pentyl, n-hexyl and any branched isomers thereof such as isopropyl, t-butyl, sec-butyl, isobutyl, and the like.

A corresponding meaning, including optional fluorine substituents, is intended for "alkoxy", "alkylene", and like terms derived from alkyl. For example, "alkoxy" includes methoxy, trifluoromethoxy, ethoxy, and oxy derivatives of the alkyls listed above. "Alkylsulfonyl" such as $C_{1-4}$alkylsulfonyl includes methylsulfonyl (methanesulfonyl), ethylsulfonyl, trifluoromethanesulfonyl, pentafluoroethylsulfonyl, and others derived from the alkyls listed above. "Alkylsulfonyloxy" such as $C_{1-4}$alkylsulfonyloxy includes methanesulfonyloxy (methylsulfonyloxy), trifluoromethanesulfonyloxy, ethanesulfonyloxy, pentafluoroethanesulfonyloxy et al.

"Cycloalkyl", for example $C_{3-6}$cycloalkyl, includes cyclopropyl, cyclobutyl, cyclopentyl and cyclohexyl, and the like.

A halogen atom present in the compounds of formula (I) may be fluorine, chlorine, bromine or iodine.

Preferably, B represents a sulfur atom.

Preferably, t represents 3.

More preferably, B is a sulfur atom and t is 3 and the invention is a compound of formula (IA) or a salt thereof:

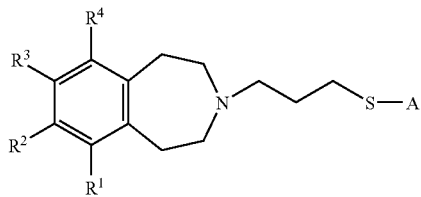

Formula (IA)

Preferably, A represents an optionally substituted 5- or 6-membered aromatic heterocyclic ring, or an optionally substituted bicyclic heterocyclic aromatic ring system (i.e. both rings of the optionally substituted bicyclic heterocyclic ring system are aromatic). It is preferred that A represents an optionally substituted 5- or 6-membered aromatic heterocyclic ring, and more preferred that A is an optionally substituted 5-membered aromatic heterocyclic ring.

It is preferred that A is selected from one of the groups (i), (ii) or (iii):

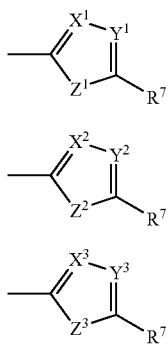

wherein:

$X^1$ and $X^2$ are independently N or $CR^8$, and $X^3$ is $NR^8$, O or S;

$Y^1$ and $Y^3$ are independently N or $CR^9$, and $Y^2$ is $NR^9$, O or S;

$Z^1$ is $NR^{10}$, O or S, and $Z^2$ and $Z^3$ are independently N or $CR^{10}$; and wherein:

$R^7$ is H, a halogen atom, OH, cyano, nitro, $C_{1-4}$alkyl, $C_{1-4}$alkoxy, $C_{1-4}$alkylenedioxy, $C_{1-4}$alkanoyl, or $C_{1-4}$alkylsulfonyl, an optionally substituted 3-, 4-, 5- or 6-membered cycloalkyl ring, or a group of the formula (a), (b), (c) or (d):

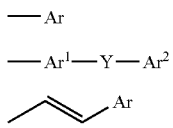

(a) —Ar
(b) —$Ar^1$—Y—$Ar^2$
(c) ⌒Ar

-continued

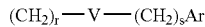

$(CH_2)_r$—V—$(CH_2)_s$Ar (d)

in which:

Ar represents an optionally substituted phenyl ring or an optionally substituted 5- or 6-membered aromatic heterocyclic ring; or an optionally substituted bicyclic ring system, $Ar^1$ and $Ar^2$ each independently represent an optionally substituted phenyl ring or an optionally substituted 5- or 6-membered aromatic heterocyclic ring, and Y represents a bond, —NHCO—, —CONH—, —$CH_2$—, or —$(CH_2)_m Y^A (CH_2)_n$—, wherein $Y^A$ represents O, S, $SO_2$, or CO and m and n each represent zero or 1 such that the sum of m+n is zero or 1, r and s independently represent an integer from zero to 3 such that the sum of r and s is equal to an integer from 1 to 4, and V represents a bond, O or S; and $R^9$ is H, a halogen atom, OH, cyano, nitro, $C_{1-4}$alkyl, $C_{1-4}$alkoxy, $C_{1-4}$alkylenedioxy, $C_{1-4}$alkanoyl, or $C_{1-4}$alkylsulfonyl, an optionally substituted 3-, 4-, 5- or 6-membered cycloalkyl ring, or a group of the formula (a), (b), (c) or (d) as defined herein, provided that $R^9$ is not a halogen atom, OH, cyano, nitro, $C_{1-4}$alkoxy or $C_{1-4}$alkylenedioxy when $R^9$ is linked to N;

or $R^9$ together with $R^7$ and the intervening atoms of the 5-membered heterocyclic ring illustrated in groups (i), (ii) or (iii) form part of an optionally substituted 5-, 6-, or 7-membered carbocyclic or heterocyclic ring; and wherein:

$R^8$ is H, OH or $C_{1-2}$alkyl, provided that $R^8$ is H or $C_{1-2}$alkyl when $R^8$ is linked to N;

$R^{10}$ is H, OH, $C_{1-6}$alkyl, hydroxy-substituted $C_{1-6}$alkyl, $C_{1-2}$alkoxy$C_{1-4}$alkyl, phenyl$C_{1-4}$alkyl, a 3-, 4-, 5- or 6-membered cycloalkyl ring, or phenyl; wherein in phenyl, phenyl$C_{1-4}$alkyl or cycloalkyl the ring is optionally substituted by one or two fluoro or $C_1$alkyl groups; and provided that $R^{10}$ is not OH when $R^{10}$ is linked to N.

Note that in groups (i), (ii) and (iii) the pendant bond at the left-hand side of each group indicates that there is a direct bond between the group B of Formula (I) and the heterocycle carbon atom located between $X^{1,2,3}$ and $Z^{1,2,3}$.

In any groups of the formula (a), (b), (c) or (d), the rings or ring systems Ar, $Ar^1$ or $Ar^2$ are preferably each independently optionally substituted by one or more substituents selected from: a halogen atom, or a hydroxy, oxo, cyano, nitro, $C_{1-4}$alkyl, $C_{1-4}$alkoxy, $C_{1-4}$alkylenedioxy, $C_{1-4}$alkanoyl, $C_{1-4}$alkylsulfonyl, $C_{1-4}$alkylsulfonyloxy, $C_{1-4}$alkylsulfinyl, $C_{1-4}$alkylthio, $R^{13}SO_2N(R^{14})$—, $R^{13}R^{14}NSO_2$—, $R^{13}R^{14}N$—, $R^{13}R^{14}NCO$—, or $R^{13}CON(R^{14})$— group wherein each of $R^{13}$ and $R^{14}$ independently represents a hydrogen atom or a $C_{1-4}$ alkyl group, or $R^{13}R^{14}$ together form a $C_{3-6}$ alkylene chain.

Alternatively or additionally, Ar and $Ar^2$ may be independently optionally substituted by one or more 5- or 6-membered aromatic heterocyclic rings, e.g. as defined below, optionally substituted by a $C_{1-2}$ alkyl or $R^{13}R^{14}N$— group; wherein $R^{13}$ and $R^{14}$ are as defined above.

In the rings Ar and $Ar^2$ substituents positioned ortho to one another may be linked to form a 5- or 6-membered ring. Preferably in this case Ar and $Ar^2$ are optionally substituted phenyl rings, and here linking two ortho substituents can for example form a benzoxazinone ring system.

It is preferred that the rings Ar, $Ar^1$, or $Ar^2$ are each independently unsubstituted or substituted by one or more substituents selected from: a halogen atom, or a cyano, $C_{1-2}$alkyl (e.g. methyl or trifluoromethyl), $C_{1-2}$alkoxy (e.g. methoxy or trifluoromethoxy), $C_{1-2}$alkylenedioxy (e.g. methylenedioxy), $C_{2-3}$alkanoyl (e.g. acetyl), $C_2$alkanoylamino (e.g. acetylamino), $C_1$ alkylsulfonyl (e.g. methylsulfonyl or trifluoromethylsulfonyl), $C_1$alkylsulfonyloxy (e.g. methylsulfonyloxy), $C_1$alkylaminosulfonyl (e.g. methylaminosulfonyl), $C_1$alkylsulfonylamino (e.g. methylsulfonylamino), or $C_1$alkylaminocarbonyl (e.g. methylaminocarbonyl) group.

The 3-, 4-, 5- or 6-membered cycloalkyl ring in e.g. $R^7$, $R^9$, and (later) $R^{11}$ can, unless stated otherwise, be independently optionally substituted by one or two F or $C_{1-2}$ alkyl groups or a $R^{15}R^{16}N$— group; wherein each of $R^{15}$ and $R^{16}$ independently represents a hydrogen atom or a $C_{1-4}$ alkyl group, or $R^{15}R^{16}$ together form a $C_{3-6}$ alkylene chain.

Preferably, $R^7$ is not H. It is advantageous that $R^7$ is a group of the formula (a), (b), (c) or (d). It is thought that these $R^7$ aryl-containing groups help to increase the compound's affinity (binding) to the dopamine $D_3$ receptor. More advantageously, $R^7$ is a group of the formula (a), (b) or (c). Still more advantageously, $R^7$ is a group of the formula (a) or (b).

It is preferred that when $R^7$ represents a group of formula (a) or (b), and Ar or $Ar^1$ is optionally substituted phenyl, there is either no substituent present in Ar or $Ar^1$ para to the 5-membered heterocycle illustrated in group (i), (ii) or (iii) or such para substituent is a either fluoro or $C_1$alkyl (e.g. $CF_3$) group. A fluoro or no substituent at such para position is preferred.

$R^7$ being an optionally substituted 3-, 4-, 5- or 6-membered cycloalkyl ring, such as an optionally substituted cyclohexyl ring, is also advantageous.

Preferably, $R^9$ is not taken together with $R^7$ and the intervening ring atoms to form part of an optionally substituted 5-, 6-, or 7-membered carbocyclic or heterocyclic ring. More preferably, $R^9$ is H or a group of the formula (a) as defined herein, still more preferably H or optionally substituted phenyl.

When $R^7$ and/or $R^9$, especially $R^7$, is/are a group of formula (a), Ar is preferably optionally substituted phenyl, quinolinyl e.g. 2-, 3-, 4-, 5- or 6-quinolinyl, furyl e.g. 2-furyl, thienyl e.g. 2-thienyl, pyridyl e.g. 4-pyridyl, indolyl, pyrazolopyrimidyl e.g. pyrazolo[1,5-a]pyrimidyl, cinnolinyl, benzo[b]furanyl or pyrrolopyridyl. More preferably, $R^7$ is optionally substituted phenyl in particular unsubstituted phenyl or fluorophenyl (e.g. 4-fluorophenyl), or optionally substituted quinolinyl e.g. 6-quinolinyl.

When $R^7$ and/or $R^9$, especially $R^7$, is/are a group of formula (b), $Ar^1$ is preferably optionally substituted phenyl, and/or Y is preferably a bond, and/or $Ar^2$ is preferably optionally substituted phenyl, pyridyl, pyrimidinyl, or a 5-membered heterocyclic aromatic ring containing at least one N and one O atom e.g. isoxazolyl, oxazolyl or oxadiazolyl. A highly preferred embodiment is wherein $Ar^1$ is optionally substituted phenyl (preferably phenyl), Y is a bond, and $Ar^2$ is optionally substituted phenyl, pyridyl, pyrimidinyl, isoxazolyl, oxazolyl or oxadiazolyl. Most preferably, $Ar^2$ is optionally substituted isoxazolyl e.g. isoxazol-5-yl (i.e. 1,2-oxazol-5-yl), oxazolyl e.g. 1,3-oxazol-2-yl, or oxadiazolyl e.g. 1,2,4-oxadiazol-3-yl.

Optimally $Ar^2$ has no substituents or is substituted by a $C_1$ alkyl e.g. methyl group, this optional substituent preferably being situated two $Ar^2$-ring-atoms from the connection point to the $Ar^1$—Y— e.g. $Ar^1$— group. For example $Ar^2$ being 5-methyl-1,2,4-oxadiazol-3-yl (see e.g. Example 30), 5-methyl-1,3-oxazol-2-yl or 4-methyl-1,3-oxazol-2-yl is preferred.

For a group of formula (b), $Ar^2$—Y— is advantageously joined to the atom of the $Ar^1$ ring two atoms removed from the $Ar^1$ atom connected to the main A ring. So, for example, where $Ar^1$ is optionally substituted phenyl, $Ar^2$—Y— is preferably joined to the meta-position of the phenyl ring relative to the main (e.g. triazolyl, imidazolyl) A ring. See for example Example 30 hereinafter.

When $R^7$ and/or $R^9$, especially $R^7$, is/are a group of formula (c), preferred examples of Ar include optionally substituted phenyl.

When $R^7$ and/or $R^9$, especially $R^7$, is/are a group of formula (d), preferably r is 1 or 2, V is a bond, and S is zero; i.e. group (d) is —$(CH_2)_r$—Ar where r is 1 or 2.

Where $R^9$ together with $R^7$ and the intervening atoms of the 5-membered heterocyclic ring illustrated in groups (i), (ii) or (iii) form part of an optionally substituted 5-, 6-, or 7-membered carbocyclic or heterocyclic ring, the latter ring is preferably a 6-membered ring, more preferably a phenyl ring (e.g. see Examples 18 and 23).

$R^{10}$ is preferably H, $C_{1-4}$alkyl or cyclopropyl, more preferably H or $C_1$alkyl (e.g. methyl or trifluoromethyl).

Preferably, $X^1$ and $X^2$ are independently N or $CR^8$, and $X^3$ is $NR^8$. More preferably, $X^1$ and $X^2$ are independently N and $X^3$ is $NR^8$.

Preferably, $Y^1$ and $Y^3$ are independently N or $CR^9$, and $Y^2$ is $NR^9$.

Preferably, $Z^1$ is $NR^{10}$, and $Z^2$ and $Z^3$ are independently N.

For A, the tautomeric form shown in group (i) is preferred. In group (i), it is preferred that one or both of $X^1$ and $Y^1$ is N.

Without intending to be limited by theory, it is thought that one or both of $X^1/X^2/X^3$ and $Y^1/Y^2/Y^3$ advantageously are or contain a ring heteroatom, ideally a N atom, for optimum $D_3$ binding.

It is preferred that A is group (i) and $Z^1$=$NR^{10}$, in which case $R^{10}$ is preferably H, $C_{1-4}$alkyl or cyclopropyl.

More preferably, B is a sulfur atom, t is 3, A is group (i), $X^1$=$Y^1$=N and $Z^1$ is $NR^{10}$, so that A is optionally substituted 1,2,4-triazol-3-yl and the invention is a compound of formula (IB) or a salt thereof:

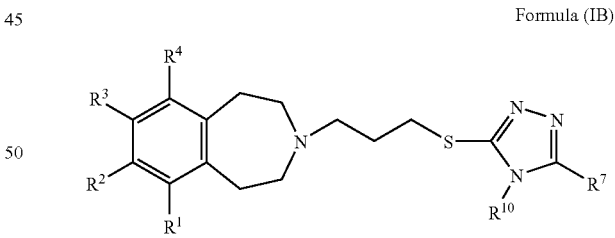

Formula (IB)

Preferably, $R^7$ is a group of formula (a), in particular an optionally substituted bicyclic ring or an optionally substituted phenyl ring, more particularly, quinolinyl, e.g. 2-, 3-, 4-, 5-, or 6-quinolinyl.

Also preferred is the embodiment wherein B is a sulfur atom, t is 3 and A is group (i), $X^1$ is N, $Y^1$ is $CR^9$, and $Z^1$ is $NR^{10}$, so that the invention is a compound of formula (IC) or a salt thereof:

Formula (IC)

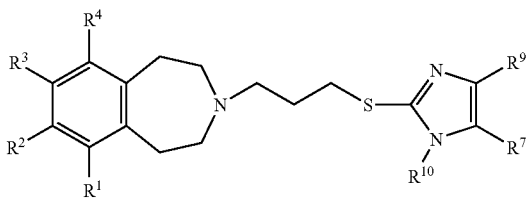

In Formula (IC) it is further preferred that $R^9$ is not taken together with $R^7$ and the intervening ring atoms to form part of an optionally substituted 5-, 6-, or 7-membered carbocyclic or heterocyclic ring. In this case, A is optionally substituted imidazol-2-yl. Preferably, $R^7$ is a group of formula (a), in particular an optionally substituted bicyclic ring or an optionally substituted phenyl ring, more particularly, quinolinyl, e.g. 2-, 3-, 4-, 5-, or 6-quinolinyl.

Also preferred is the embodiment wherein B is a sulfur atom, t is 3 and A is group (i), $X^1$ is $CR^8$, $Y^1$ is N and $Z^1$ is $NR^{10}$, so that the invention is a compound of Formula (ID) or a salt thereof:

Formula (ID)

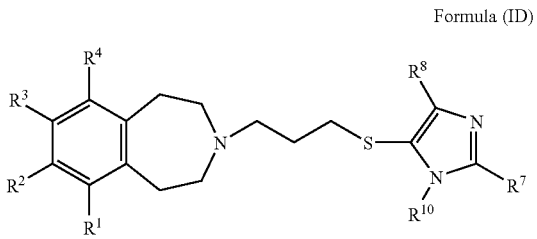

In Formula (ID), A is optionally substituted imidazol-4-yl or -5-yl, and preferably $R^8$ is H. Preferably, $R^7$ is a group of formula (a), in particular an optionally substituted bicyclic ring or an optionally substituted phenyl ring, more particularly, quinolinyl, e.g. 2-, 3-, 4-, 5-, or 6-quinolinyl.

Another embodiment is where A is the following group (iv):

(iv)

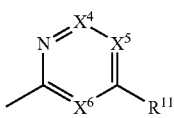

where $R^{11}$ has the same (essential and preferable) definitions as $R^7$ herein (but including H in the definitions where H is excluded from $R^7$); $X^4$ is $CR^{12a}$ or N, $X^5$ is $CR^{12b}$ or N, and $X^6$ is $CR^{12c}$ or N provided that both $X^4$ and $X^5$ are not N; and wherein $R^{12a,b,c}$, independently of each other, are as defined for the optional substituents of group A described below (i.e. including H as a possibility); and/or wherein either (a) $X^4$ and $X^5$, or (b) $X^5$, $R^{11}$ and the intervening carbon atom, or (c) $X^6$, $R^{11}$ and the intervening carbon atom, together form part of an optionally substituted 5-, 6-, or 7-membered carbocyclic or heterocyclic ring (e.g. as preferably defined for groups (i), (ii) and (iii) above for when $R^7$ and $R^9$ together form a ring).

Preferably, $R^{11}$ has the same definition(s) as $R^7$ herein (but including H in the definitions where H is excluded from $R^7$); $X^4$ is $CR^{12a}$ or N, $X^5$ is $CR^{12b}$ or N, and $X^6$ is $CR^{12c}$ or N provided that both $X^4$ and $X^5$ are not N; and wherein $R^{12a,b,c}$, independently of each other, are as defined for the optional substituents of group A described below (i.e. including H as a possibility)—i.e. there is no extra optionally substituted 5-, 6-, or 7-membered carbocyclic or heterocyclic ring fused to group (iv) above.

Preferably, $X^6$ is N, and/or $R^{11}$ is H or $C_{1-4}$alkyl (e.g. $CF_3$).

The following features are preferred or optional for any of the compounds of Formulae (I), (IA), (IB), (IC) or (ID) or salts thereof.

An optionally substituted 5- or 6-membered heterocyclic aromatic ring, as defined for any of the groups A, Ar, $Ar^1$, $Ar^2$ or $Ar^3$ may contain from 1 to 4 heteroatoms, preferably from 1 to 3 heteroatoms, selected from O, N and S. When the ring contains 2-4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl, and isoxazolyl. For group A, preferred examples include triazolyl (especially 1,2,4-triazol-3-yl) and imidazolyl (especially imidazol-2-yl). For group Ar, preferred examples include furyl e.g. 2-furyl, thienyl e.g. 2-thienyl, and pyridyl e.g. 4-pyridyl.

Examples of bicyclic ring systems for the group A include bicyclic heteroaromatic ring systems, such as indazolyl, indolyl, benzofuranyl, benzothienyl, benzothiazolyl, benzimidazolyl e.g. benzimidazol-2-yl, benzoxazolyl e.g. benzoxazol-2-yl, benzisoxazolyl, benzisothiazolyl, quinolinyl, quinoxolinyl, quinazolinyl, cinnolinyl, or isoquinolinyl.

Examples of bicyclic ring systems for Ar (e.g. in groups $R^7$, $R^9$, etc. in groups (i), (ii) or (iii)) include bicyclic aromatic, e.g. bicyclic heteroaromatic, ring systems such as: naphthyl e.g. 2-naphthyl, indazolyl, indolyl, benzofuranyl, benzothienyl, benzothiazolyl, benzimidazolyl e.g. benzimidazol-2-yl, benzoxazolyl e.g. benzoxazol-2-yl, benzisoxazolyl, benzisothiazolyl, quinolinyl e.g. 2-, 3-, 4-, 5- or 6-quinolinyl, quinoxolinyl, quinazolinyl, cinnolinyl, isoquinolinyl, naphthyridinyl, pyrazolopyrimidyl e.g. pyrazolo[1,5-a]pyrimidyl, pyrrolopyridyl e.g. pyrrolo[3,2-b]pyridyl or pyrrolo[3,2-c]pyridyl, thienothiophenyl e.g. thieno[3,2-b]thiophenyl, 1,2-dihydro-2-oxo-quinolinyl, 3,4-dihydro-3-oxo-2H-benzoxazinyl, or 1,2-dihydro-2-oxo-3H-indolyl. Preferred examples include quinolinyl, e.g. 2-, 3-, 4-, 5- or 6-quinolinyl or thienopyridine.

The groups/rings/ring systems A or $Ar^3$ may each independently be optionally substituted by one or more substituents selected from: a halogen atom, or a hydroxy, oxo, cyano, nitro, $C_{1-4}$alkyl, $C_{1-4}$alkoxy, $C_{1-4}$alkylenedioxy, $C_{1-4}$alkanoyl, or $C_{1-4}$alkylsulfonyl group.

Alternatively, the ring/ring system A may be optionally substituted by one or more groups of the formula (a), (b), (c), or (d) as defined herein; and/or by one or more non-aromatic 3-, 4-, 5-, 6-, or 7-membered heterocyclic or carbocyclic rings optionally substituted by one or two F or $C_{1-2}$ alkyl groups or a $R^{15}R^{16}N$— group; wherein each of $R^{15}$ and $R^{16}$ independently represents a hydrogen atom or a $C_{1-4}$ alkyl group, or $R^{15}R^{16}$ together form a $C_{3-6}$ alkylene chain.

In the group A substituents positioned ortho to one another may be linked to form a 5- or 6-membered ring.

It is preferred that the groups A or $Ar^3$ are each independently optionally substituted by one or more substituents selected from: a halogen atom, or a cyano, $C_{1-2}$alkyl (e.g. methyl or trifluoromethyl), $C_{1-2}$alkoxy (e.g. methoxy), $C_{1-2}$alkylenedioxy (e.g. methylenedioxy), $C_{2-3}$alkanoyl (e.g. acetyl), $C_2$alkanoylamino (e.g. acetylamino), or $C_1$alkylsulfonyl (e.g. methylsulfonyl or trifluoromethylsulfonyl) group. It is more preferred that $Ar^3$ is optionally substituted by a $C_1$alkyl (e.g. methyl) group.

When $R^2$ and/or $R^3$ represents an aryl$C_{1-4}$alkoxy, arylsulfonyl, arylsulfonyloxy, arylsulfonyl$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety may be selected from an optionally substituted phenyl ring or an optionally substituted 5- or 6-membered heterocyclic ring. In the group $R^2$ and/or $R^3$ an aryl moiety may be optionally substituted by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$alkanoyl, or $R^{17}R^{18}NCO$ where each of $R^{17}$ and $R^{18}$ independently represents a hydrogen atom or $C_{1-4}$alkyl group.

Where $R^2$ and/or $R^3$ independently represent the group $R^5CON(R^6)(CH_2)_p$, $R^5R^6NCO(CH_2)_p$ or $R^5R^6NSO_2(CH_2)_p$ in which $R^5CONR^6$ or $R^5R^6N$ together form a 4-,5-,6- or 7-membered azacyclic group, then this can be characterised by: (i) containing one additional O, N or S atom in the azacycle, for example the azacyclic group being 1,4-morpholin-4-yl and/or (ii) having 1-2 optional $C_{1-2}$alkyl substituents whose carbon atoms are included in the azacyclic group's 3-8 carbon atoms. One, two or more F atoms can optionally be included as substituents of the carbon atoms of the heterocycle. The term 'azacyclic group' should be interpreted to cover only stable azacycles such as 1,4-morpholine and piperazine and not for example 1,3-morpholine. Saturated azacycles, in particular piperidinyl, pyrrolidinyl, 1,4-morpholinyl, and including the corresponding α-oxo-azacycles $R^5CONR^6$, are preferred.

The substituents $R^2$ and $R^3$ may be the same or different. Preferably, $R^2$ is other than hydrogen.

It is preferred that $R^2$ represents a substituent selected from: a halogen atom, cyano, acetyl, trifluoromethyl, pentafluoroethyl, trifluoromethoxy, $C_{1-4}$alkylsulfonyl, $C_{1-4}$alkylsulfonyloxy; a $R^5R^6NSO_2$ group where each of $R^5$ and $R^6$ independently represents a hydrogen atom or a $C_{1-4}$alkyl group, or $R^5R^6N$ together form a 4-, 5-, 6- or 7-membered azacyclic group optionally containing one additional O, N or S atom in the azacycle and having 3-8 carbon atoms; or a group $Ar^3Z$, where Z is a bond and $Ar^3$ is an optionally substituted 5- or 6-membered heterocyclic aromatic ring.

More preferably, $R^2$ represents a substituent selected from: $C_{1-4}$alkylsulfonyl (e.g. methylsulfonyl, trifluoromethylsulfonyl, or ethylsulfonyl), $C_{1-4}$alkylsulfonyloxy (e.g. methylsulfonyloxy or trifluoromethylsulfonyloxy); a $R^5R^6NSO_2$ group where each of $R^5$ and $R^6$ independently represents a hydrogen atom or a $C_{1-4}$alkyl group (e.g. a N,N-dimethylaminosulfonyl group), or $R^5R^6N$ together form a 4-,5-, 6- or 7-membered azacyclic group optionally containing one additional O, N or S atom in the azacycle and having 3-8 carbon atoms (e.g. a piperidin-1-ylsulfonyl, pyrrolidin-1-ylsulfonyl or 1,4-morpholin-4-ylsulfonyl group); or a group $Ar^3Z$, where Z is a bond and $Ar^3$ is an optionally substituted 5- or 6-membered heterocyclic aromatic ring.

Still more preferably, $R^2$ represents a methylsulfonyl, ethylsulfonyl, N,N-dimethylaminosulfonyl, pyrrolidin-1-ylsulfonyl, 1,4-morpholin-4-ylsulfonyl or methylsulfonyloxy group, or $R^2$ represents a pyrazin-2-yl, 5-methyl-oxazol-2-yl or 5-methyl-isoxazol-3-yl group.

Preferably, $R^3$ is hydrogen or one of the substituents preferred for $R^2$. More preferably, $R^3$ is hydrogen.

It is preferred that at least one of $R^1$ and $R^4$ is H, more preferred that both $R^1$ and $R^4$ are H, and most preferred that $R^1$, $R^3$, and $R^4$ are all H.

It will be appreciated that for use in medicine the salts of the compounds of the invention should be pharmaceutically (i.e physiologically) acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-pharmaceutically acceptable salts eg. oxalates, may be used, for example in the isolation of compounds of the invention and are included within the scope of this invention. Also included within the scope of the invention are solvates, hydrates, complexes and prodrugs of compounds of the invention.

Certain of the compounds of the invention may form acid addition salts with one or more equivalents of the acid. The present invention includes within its scope all possible stoichiometric and non-stoichiometric forms. Certain groups/substituents included in the present invention may be present as isomers. The present invention includes within its scope all such isomers, including racemates, enantiomers and mixtures thereof. When A represents a group (c) the compounds may also exist as geometric isomers around the double bond; all isomers are included though trans geometry of the double bond in (c) is preferred.

Preferred compounds have a molecular weight of 800 or less. Still more preferred are compounds having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

Certain of the substituted heteroaromatic ring systems included in compounds of formula (I) may exist in one or more tautomeric forms. The present invention includes within its scope all such tautomeric forms, including mixtures. For example, where $R^7$, $R^8$, $R^9$, and/or $R^{10}$ is/are OH, in A groups (i), (ii) or (iii) above, the 5-membered ring can be in the keto or enol forms.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Particular compounds and salts according to the invention include those specifically exemplified in Table 1 and Examples 173 to 177 and those specifically exemplified and named hereinafter, for example:—

Ex 1. 3-{3-[(4-methyl-5-phenyl-4H-1,2,4-triazol-3-yl)thio]propyl}-2,3,4,5-tetrahydro-1H-3-benzazepin-7-yl methanesulfonate;

Ex 2. 3-{3-[(4-methyl-5-phenyl-4H-1,2,4-triazol-3-yl)thio]propyl}-2,3,4,5-tetrahydro-1H-3-benzazepine-7-carbonitrile;

Ex 3. 7-(5-methyl-1,2,4-oxadiazol-3-yl)-3-{3-[(4-methyl-5-phenyl-4H-1,2,4-triazol-3-yl)thio]propyl}-2,3,4,5-tetrahydro-1H-3-benzazepine;

Ex 4. 3-{3-[(4-methyl-5-phenyl-4H-1,2,4-triazol-3-yl)thio]propyl}-7-(methylsulfonyl)-2,3,4,5-tetrahydro-1H-3-benzazepine;

Ex 5. 3-{3-[(4,5-diphenyl-1H-imidazol-2-yl)thio]propyl}-7-(methylsulfonyl)-2,3,4,5-tetrahydro-1H-3-benzazepine;

Ex 6. 3-(3-{[4-methyl-5-(6-quinolinyl)-4H-1,2,4-triazol-3-yl]thio} propyl)-7-(methylsulfonyl)-2,3,4,5-tetrahydro-1H-3-benzazepine;

Ex 7. 3-(3-{[5-(2-furanyl)-4-methyl-4H-1,2,4-triazol-3-yl]thio}propyl)-2,3,4,5-tetrahydro-1H-3-benzazepin-7-yl methanesulfonate;

Ex 8. 3-(3-{[4-methyl-5-(2-thienyl)-4H-1,2,4-triazol-3-yl]thio}propyl)-2,3,4,5-tetrahydro-1H-3-benzazepin-7-yl methanesulfonate;

Ex 9. 3-(3-{[4-methyl-5-(4-pyridinyl)-4H-1,2,4-triazol-3-yl]thio}propyl)-2,3,4,5-tetrahydro-1H-3-benzazepin-7-yl methanesulfonate;

Ex 10. 3-[3-({5-[4-(1,1-dimethylethyl)phenyl]-4-methyl-4H-1,2,4-triazol-3-yl}thio)propyl]-2,3,4,5-tetrahydro-1H-3-benzazepin-7-yl methanesulfonate;

Ex 11. 3-(3-{[4-methyl-5-(5-methyl-3-isoxazolyl)-4H-1,2,4-triazol-3-yl]thio}propyl)-2,3,4,5-tetrahydro-1H-3-benzazepin-7-yl methanesulfonate;

Ex 12. 3-(3-{[5-(2,4-dichlorophenyl)-4-methyl-4H-1,2,4-triazol-3-yl]thio}propyl)-2,3,4,5-tetrahydro-1H-3-benzazepin-7-yl methanesulfonate;

Ex 13. 3-(3-{[4-methyl-5-(6-quinolinyl)-4H-1,2,4-triazol-3-yl]thio}propyl)-2,3,4,5-tetrahydro-1H-3-benzazepin-7-yl methanesulfonate;

Ex 14. 3-(3-{[5-(4-fluorophenyl)-4-methyl-4H-1,2,4-triazol-3-yl]thio}propyl)-2,3,4,5-tetrahydro-1H-3-benzazepin-7-yl methanesulfonate;

Ex 15. 3-[3-({4-methyl-5-[4-(trifluoromethyl)phenyl]-4H-1,2,4-triazol-3-yl}thio)propyl]-2,3,4,5-tetrahydro-1H-3-benzazepin-7-yl methanesulfonate;

Ex 16. 3-(3-{[5-(4-chlorophenyl)-1-methyl-1H-imidazol-2-yl]thio}propyl)-2,3,4,5-tetrahydro-1H-3-benzazepin-7-yl methanesulfonate;

Ex 17. 3-{3-[(5-phenyl-1,3,4-oxadiazol-2-yl)thio]propyl}-2,3,4,5-tetrahydro-1H-3-benzazepin-7-yl methanesulfonate;

Ex 18. 3-[3-(1,3-benzoxazol-2-ylthio)propyl]-2,3,4,5-tetrahydro-1H-3-benzazepin-7-yl methanesulfonate;

Ex 19. 3-{3-[(4-methyl-4H-1,2,4-triazol-3-yl)thio]propyl}-2,3,4,5-tetrahydro-1H-3-benzazepin-7-yl methanesulfonate;

Ex 20. 3-{3-[(1-methyl-1H-imidazol-2-yl)thio]propyl}-2,3,4,5-tetrahydro-1H-3-benzazepin-7-yl methanesulfonate;

Ex 21. 3-{3-[(2,5-dimethyl-3-furanyl)thio]propyl}-2,3,4,5-tetrahydro-1H-3-benzazepin-7-yl methanesulfonate;

Ex 22. 3-{3-[(4,5-diphenyl-1H-imidazol-2-yl)thio]propyl}-2,3,4,5-tetrahydro-1H-3-benzazepin-7-yl methanesulfonate;

Ex 23. 3-[3-(1H-benzimidazol-2-ylthio)propyl]-2,3,4,5-tetrahydro-1H-3-benzazepin-7-yl methanesulfonate;

Ex 24. 3-[3-(2-pyridinylthio)propyl]-2,3,4,5-tetrahydro-1H-3-benzazepin-7-yl methanesulfonate;

Ex 25. 3-[3-(2-pyrimidinylthio)propyl]-2,3,4,5-tetrahydro-1H-3-benzazepin-7-yl methanesulfonate;

Ex 26. 3-[3-(2-quinolinylthio)propyl]-2,3,4,5-tetrahydro-1H-3-benzazepin-7-yl methanesulfonate;

Ex 27. 3-(3-{[4-(trifluoromethyl)-2-pyrimidinyl]thio}propyl)-2,3,4,5-tetrahydro-1H-3-benzazepin-7-yl methanesulfonate;

Ex 28. 3-{3-[(4-phenyl-2-pyrimidinyl)thio]propyl}-2,3,4,5-tetrahydro-1H-3-benzazepin-7-yl methanesulfonate;

Ex 29. 3-{3-[(5-phenyl-3-pyridazinyl)thio]propyl}-2,3,4,5-tetrahydro-1H-3-benzazepin-7-yl methanesulfonate;

Ex 30. 3-[3-({4-methyl-5-[3-(5-methyl-1,2,4-oxadiazol-3-yl)phenyl]-4H-1,2,4-triazol-3-yl}thio)propyl]-2,3,4,5-tetrahydro-1H-3-benzazepin-7-yl methanesulfonate;

Ex 31. 3-(3-{[5-(3-cyanophenyl)-4-methyl-4H-1,2,4-triazol-3-yl]thio}propyl)-2,3,4,5-tetrahydro-1H-3-benzazepin-7-yl methanesulfonate;

Ex 32. 3-(3-{[4-methyl-5-(2-methyl-5-quinolinyl)-4H-1,2,4-triazol-3-yl]thio}propyl)-2,3,4,5-tetrahydro-1H-3-benzazepin-7-yl methanesulfonate;

Ex 33. 3-(3-{[4-methyl-5-(3-quinolinyl)-4H-1,2,4-triazol-3-yl]thio} propyl)-2,3,4,5-tetrahydro-1H-3-benzazepin-7-yl methanesulfonate;

Ex 34. 3-[3-({4-methyl-5-[3-(trifluoromethyl)phenyl]-4H-1,2,4-triazol-3-yl}thio)propyl]-2,3,4,5-tetrahydro-1H-3-benzazepin-7-yl methanesulfonate;

Ex 35. 3-(3-{[5-(4-fluorophenyl)-1-methyl-1H-imidazol-2-yl]thio}propyl)-2,3,4,5-tetrahydro-1H-3-benzazepin-7-yl methanesulfonate;

Ex 36. 3-{3-[(1-methyl-4,5-diphenyl-1H-imidazol-2-yl)thio]propyl}-2,3,4,5-tetrahydro-1H-3-benzazepin-7-yl methanesulfonate;

Ex 37. 3-(3-{[5-(2-fluorophenyl)-4-methyl-4H-1,2,4-triazol-3-yl]thio}propyl)-2,3,4,5-tetrahydro-1H-3-benzazepin-7-yl methanesulfonate;

Ex 38. 3-(3-{[5-(3-fluorophenyl)-4-methyl-4H-1,2,4-triazol-3-yl]thio}propyl)-2,3,4,5-tetrahydro-1H-3-benzazepin-7-yl methanesulfonate;

Ex 39. 3-(3-{[5-(3,4-difluorophenyl)-4-methyl-4H-1,2,4-triazol-3-yl]thio}propyl)-2,3,4,5-tetrahydro-1H-3-benzazepin-7-yl methanesulfonate;

Ex 40. 3-{3-[(5-cyclohexyl-4-methyl-4H-1,2,4-triazol-3-yl)thio]propyl}-2,3,4,5-tetrahydro-1H-3-benzazepin-7-yl methanesulfonate;

Ex 41. 3-(3-{[5-(4-fluorophenyl)-4-methyl-4H-1,2,4-triazol-3-yl]thio}propyl)-7-(methylsulfonyl)-2,3,4,5-tetrahydro-1H-3-benzazepine;

Ex 42. 7-(methylsulfonyl)-3-{3-[(4-phenyl-1,3-thiazol-2-yl)thio]propyl}-2,3,4,5-tetrahydro-1H-3-benzazepine;

Ex 43. 3-[3-({5-[(E)-2-(4-fluorophenyl)ethenyl]-4-methyl-4H-1,2,4-triazol-3-yl}thio)propyl]-7-(methylsulfonyl)-2,3,4,5-tetrahydro-1H-3-benzazepine;

Ex 44. 7-(ethylsulfonyl)-3-(3-{[5-(4-fluorophenyl)-4-methyl-4H-1,2,4-triazol-3-yl]thio}propyl)-2,3,4,5-tetrahydro-1H-3-benzazepine;

Ex 45. 7-(ethylsulfonyl)-3-(3-{[4-methyl-5-(6-quinolinyl)-4H-1,2,4-triazol-3-yl]thio}propyl)-2,3,4,5-tetrahydro-1H-3-benzazepine;

Ex 46. 7-(ethylsulfonyl)-3-{3-[(1-methyl-2-phenyl-1H-imidazol-5-yl)thio]propyl}-2,3,4,5-tetrahydro-1H-3-benzazepine;

Ex 47. 3-(3-{[5-(4-fluorophenyl)-4-methyl-4H-1,2,4-triazol-3-yl]thio}propyl)-7-(1-pyrrolidinylsulfonyl)-2,3,4,5-tetrahydro-1H-3-benzazepine;

Ex 48. 3-(3-{[4-methyl-5-(6-quinolinyl)-4H-1,2,4-triazol-3-yl]thio} propyl)-7-(1-pyrrolidinylsulfonyl)-2,3,4,5-tetrahydro-1H-3-benzazepine;

Ex 49. 3-{3-[(4,5-diphenyl-1H-imidazol-2-yl)thio]propyl}-7-(1-pyrrolidinylsulfonyl)-2,3,4,5-tetrahydro-1H-3-benzazepine;

Ex 50. 3-(3-{[5-(4-fluorophenyl)-4-methyl-4H-1,2,4-triazol-3-yl]thio}propyl)-7-(4-morpholinylsulfonyl)-2,3,4,5-tetrahydro-1H-3-benzazepine;

Ex 51. 3-(3-{[4-methyl-5-(6-quinolinyl)-4H-1,2,4-triazol-3-yl]thio} propyl)-7-(4-morpholinylsulfonyl)-2,3,4,5-tetrahydro-1H-3-benzazepine;

Ex 52. 3-(3-{[5-(4-fluorophenyl)-4-methyl-4H-1,2,4-triazol-3-yl]thio}propyl)-7-(2-pyrazinyl)-2,3,4,5-tetrahydro-1H-3-benzazepine;

Ex 53. 3-(3-{[4-methyl-5-(6-quinolinyl)-4H-1,2,4-triazol-3-yl]thio} propyl)-7-(2-pyrazinyl)-2,3,4,5-tetrahydro-1H-3-benzazepine;

Ex 54. 3-(3-{[5-(4-fluorophenyl)-4-methyl-4H-1,2,4-triazol-3-yl]thio}propyl)-N,N-dimethyl-2,3,4,5-tetrahydro-1H-3-benzazepine-7-sulfonamide;

Ex 55. N,N-dimethyl-3-(3-{[4-methyl-5-(6-quinolinyl)-4H-1,2,4-triazol-3-yl]thio}propyl)-2,3,4,5-tetrahydro-1H-3-benzazepine-7-sulfonamide;

Ex 56. 3-(3-{[4-methyl-5-(4-quinolinyl)-4H-1,2,4-triazol-3-yl]thio} propyl)-7-(methylsulfonyl)-2,3,4,5-tetrahydro-1H-3-benzazepine;

Ex 57. 7-(ethylsulfonyl)-3-[3-({4-methyl-5-[3-(5-methyl-1,2,4-oxadiazol-3-yl)phenyl]-4H-1,2,4-triazol-3-yl}thio)propyl]-2,3,4,5-tetrahydro-1H-3-benzazepine;

Ex 58. 7-(ethylsulfonyl)-3-(3-{[4-methyl-5-(2-methyl-5-quinolinyl)-4H-1,2,4-triazol-3-yl]thio}propyl)-2,3,4,5-tetrahydro-1H-3-benzazepine;

Ex 59. 7-(ethylsulfonyl)-3-[3-({5-[(E)-2-(4-fluorophenyl)ethenyl]-4-methyl-4H-1,2,4-triazol-3-yl}thio)propyl]-2,3,4,5-tetrahydro-1H-3-benzazepine;

Ex 60. 3-(3-{[5-(4-fluorophenyl)-4-methyl-4H-1,2,4-triazol-3-yl]thio}propyl)-7-(5-methyl-1,3-oxazol-2-yl)-2,3,4,5-tetrahydro-1H-3-benzazepine;

Ex 61. 7-(5-methyl-1,3-oxazol-2-yl)-3-(3-{[4-methyl-5-(6-quinolinyl)-4H-1,2,4-triazol-3-yl]thio}propyl)-2,3,4,5-tetrahydro-1H-3-benzazepine;

Ex 62. 3-(3-{[5-(4-fluorophenyl)-4-methyl-4H-1,2,4-triazol-3-yl]thio}propyl)-7-(5-methyl-3-isoxazolyl)-2,3,4,5-tetrahydro-1H-3-benzazepine;

Ex 63. 7-(5-methyl-3-isoxazolyl)-3-(3-{[4-methyl-5-(6-quinolinyl)-4H-1,2,4-triazol-3-yl]thio}propyl)-2,3,4,5-tetrahydro-1H-3-benzazepine;

Ex 64. 3-(3-{[4-methyl-5-(6-quinolinyl)-4H-1,2,4-triazol-3-yl]thio} propyl)-7-(1-piperidinylsulfonyl)-2,3,4,5-tetrahydro-1H-3-benzazepine;

Ex 65. 3-(3-{[5-(4-fluorophenyl)-4-methyl-4H-1,2,4-triazol-3-yl]thio}propyl)-7-(1-piperidinylsulfonyl)-2,3,4,5-tetrahydro-1H-3-benzazepine;

Ex 66. 3-(3-{[4-methyl-5-(6-quinolinyl)-4H-1,2,4-triazol-3-yl]thio}propyl)-7-(phenylsulfonyl)-2,3,4,5-tetrahydro-1H-3-benzazepine;

Ex 67. 3-(3-{[5-(2,4-difluorophenyl)-4-methyl-4H-1,2,4-triazol-3-yl]thio}propyl)-7-(phenylsulfonyl)-2,3,4,5-tetrahydro-1H-3-benzazepine;

Ex 68. 3-(3-{[5-(4-fluorophenyl)-4-methyl-4H-1,2,4-triazol-3-yl]thio}propyl)-7-(phenylsulfonyl)-2,3,4,5-tetrahydro-1H-3-benzazepine;

Ex 69. 3-{3-[(5-cyclohexyl-4-methyl-4H-1,2,4-triazol-3-yl)thio]propyl}-7-(4-morpholinylsulfonyl)-2,3,4,5-tetrahydro-1H-3-benzazepine;

Ex 70. 3-(3-{[5-(2,4-difluorophenyl)-4-methyl-4H-1,2,4-triazol-3-yl]thio}propyl)-7-(4-morpholinylsulfonyl)-2,3,4,5-tetrahydro-1H-3-benzazepine;

Ex 71. 3-(3-{[1-methyl-5-(6-quinolinyl)-1H-imidazol-2-yl]thio} propyl)-7-(4-morpholinylsulfonyl)-2,3,4,5-tetrahydro-1H-3-benzazepine;

Ex 72. 3-(3-{[5-(1H-indol-2-yl)-4-methyl-4H-1,2,4-triazol-3-yl]thio}propyl)-7-(methylsulfonyl)-2,3,4,5-tetrahydro-1H-3-benzazepine;

Ex 73. 3-(3-{[4-methyl-5-(2-methyl-6-quinolinyl)-4H-1,2,4-triazol-3-yl]thio}propyl)-7-(methylsulfonyl)-2,3,4,5-tetrahydro-1H-3-benzazepine;

Ex 74. 3-(3-{[4-methyl-5-(1-methyl-1H-indol-5-yl)-4H-1,2,4-triazol-3-yl]thio}propyl)-7-(methylsulfonyl)-2,3,4,5-tetrahydro-1H-3-benzazepine;

Ex 75. 3-(3-{[5-(1H-indol-6-yl)-4-methyl-4H-1,2,4-triazol-3-yl]thio}propyl)-7-(methylsulfonyl)-2,3,4,5-tetrahydro-1H-3-benzazepine;

Ex 76. 3-[3-({5-[(E)-2-(phenyl)ethenyl]-4-methyl-4H-1,2,4-triazol-3-yl}thio)propyl]-7-(methylsulfonyl)-2,3,4,5-tetrahydro-1H-3-benzazepine Ex 77. 3-(3-{[4-methyl-5-(2-naphthalenyl)-4H-1,2,4-triazol-3-yl]thio}propyl)-7-(methylsulfonyl)-2,3,4,5-tetrahydro-1H-3-benzazepine;

Ex 78. 3-(3-{[5-(1-benzothien-2-yl)-4-methyl-4H-1,2,4-triazol-3-yl]thio}propyl)-7-(methylsulfonyl)-2,3,4,5-tetrahydro-1H-3-benzazepine;

Ex 79. 3-(3-{[4-methyl-5-(1-methyl-1H-indol-2-yl)-4H-1,2,4-triazol-3-yl]thio}propyl)-7-(methylsulfonyl)-2,3,4,5-tetrahydro-1H-3-benzazepine;

Ex 80. 3-(3-{[5-(1-benzofuran-2-yl)-4-methyl-4H-1,2,4-triazol-3-yl]thio}propyl)-7-(methylsulfonyl)-2,3,4,5-tetrahydro-1H-3-benzazepine;

Ex 81. 3-(3-{[5-(1H-indol-5-yl)-4-methyl-4H-1,2,4-triazol-3-yl]thio}propyl)-7-(methylsulfonyl)-2,3,4,5-tetrahydro-1H-3-benzazepine;

Ex 82. 3-(3-{[4-methyl-5-(1-methyl-1H-indol-3-yl)-4H-1,2,4-triazol-3-yl]thio}propyl)-7-(methylsulfonyl)-2,3,4,5-tetrahydro-1H-3-benzazepine;

Ex 83. 3-(3-{[5-(1H-indol-4-yl)-4-methyl-4H-1,2,4-triazol-3-yl]thio}propyl)-7-(methylsulfonyl)-2,3,4,5-tetrahydro-1H-3-benzazepine;

Ex 84. 3-[3-({4-methyl-5-[3-(5-methyl-1,2,4-oxadiazol-3-yl)phenyl]-4H-1,2,4-triazol-3-yl}thio)propyl]-7-(methylsulfonyl)-2,3,4,5-tetrahydro-1H-3-benzazepine;

Ex 85. 3-(3-{[5-(1H-indol-7-yl)-4-methyl-4H-1,2,4-triazol-3-yl]thio}propyl)-7-(methylsulfonyl)-2,3,4,5-tetrahydro-1H-3-benzazepine;

Ex 86. 3-(3-{[5-(1-benzothien-3-yl)-4-methyl-4H-1,2,4-triazol-3-yl]thio}propyl)-7-(methylsulfonyl)-2,3,4,5-tetrahydro-1H-3-benzazepine;

Ex 87. 7-(methylsulfonyl)-3-{3-[(4-methyl-5-thieno[2,3-b]pyridin-3-yl-4H-1,2,4-triazol-3-yl)thio]propyl}-2,3,4,5-tetrahydro-1H-3-benzazepine;

Ex 88. 3-{3-[(4-ethyl-5-phenyl-4H-1,2,4-triazol-3-yl)thio]propyl}-7-(methylsulfonyl)-2,3,4,5-tetrahydro-1H-3-benzazepine;

Ex 89. 7-(ethylsulfonyl)-3-(3-{[5-(1H-indol-6-yl)-4-methyl-4H-1,2,4-triazol-3-yl]thio}propyl)-2,3,4,5-tetrahydro-1H-3-benzazepine;

Ex 90. 7-(ethylsulfonyl)-3-(3-{[5-(1H-indol-5-yl)-4-methyl-4H-1,2,4-triazol-3-yl]thio}propyl)-2,3,4,5-tetrahydro-1H-3-benzazepine;

Ex 91. 3-(3-{[5-(1-benzothien-2-yl)-4-methyl-4H-1,2,4-triazol-3-yl]thio}propyl)-7-(ethylsulfonyl)-2,3,4,5-tetrahydro-1H-3-benzazepine;

Ex 92. 3-{3-[(5-cyclohexyl-4-methyl-4H-1,2,4-triazol-3-yl)thio]propyl}-7-(ethylsulfonyl)-2,3,4,5-tetrahydro-1H-3-benzazepine;

Ex 93. 7-(ethylsulfonyl)-3-(3-{[5-(1H-indol-2-yl)-4-methyl-4H-1,2,4-triazol-3-yl]thio}propyl)-2,3,4,5-tetrahydro-1H-3-benzazepine;

Ex 94. 7-(ethylsulfonyl)-3-(3-{[4-methyl-5-(2-methyl-6-quinolinyl)-4H-1,2,4-triazol-3-yl]thio}propyl)-2,3,4,5-tetrahydro-1H-3-benzazepine;

Ex 95. 3-(3-{[5-(1-benzofuran-2-yl)-4-methyl-4H-1,2,4-triazol-3-yl]thio}propyl)-7-(ethylsulfonyl)-2,3,4,5-tetrahydro-1H-3-benzazepine;

Ex 96. 3-(3-{[5-(1-benzofuran-4-yl)-4-methyl-4H-1,2,4-triazol-3-yl]thio}propyl)-7-(ethylsulfonyl)-2,3,4,5-tetrahydro-1H-3-benzazepine;

Ex 97. 7-(ethylsulfonyl)-3-(3-{[1-methyl-5-(6-quinolinyl)-1H-imidazol-2-yl]thio}propyl)-2,3,4,5-tetrahydro-1H-3-benzazepine;

Ex 98. 7-(ethylsulfonyl)-3-{3-[(3-phenyl-1H-1,2,4-triazol-5-yl)thio]propyl}-2,3,4,5-tetrahydro-1H-3-benzazepine;

Ex 99. 7-(ethylsulfonyl)-3-(3-{[4-methyl-5-(1-methyl-1H-indol-2-yl)-4H-1,2,4-triazol-3-yl]thio}propyl)-2,3,4,5-tetrahydro-1H-3-benzazepine;

Ex 100. 3-(3-{[5-(1-benzofuran-7-yl)-4-methyl-4H-1,2,4-triazol-3-yl]thio}propyl)-7-(ethylsulfonyl)-2,3,4,5-tetrahydro-1H-3-benzazepine;

Ex 101. 7-(ethylsulfonyl)-3-(3-{[5-(4-fluorophenyl)-1-methyl-1H-imidazol-2-yl]thio}propyl)-2,3,4,5-tetrahydro-1H-3-benzazepine;

Ex 102. 7-(ethylsulfonyl)-3-(3-{[5-(1H-indol-3-yl)-4-methyl-4H-1,2,4-triazol-3-yl]thio}propyl)-2,3,4,5-tetrahydro-1H-3-benzazepine;

Ex 103. 3-(3-{[5-(2,4-difluorophenyl)-4-methyl-4H-1,2,4-triazol-3-yl]thio}propyl)-7-(ethylsulfonyl)-2,3,4,5-tetrahydro-1H-3-benzazepine;

Ex 104. 7-(ethylsulfonyl)-3-{3-[(1-methyl-5-phenyl-1H-imidazol-2-yl)thio]propyl}-2,3,4,5-tetrahydro-1H-3-benzazepine;

Ex 105. 7-(ethylsulfonyl)-3-[3-({4-methyl-5-[3-(3-methyl-5-isoxazolyl)phenyl]-4H-1,2,4-triazol-3-yl}thio)propyl]-2,3,4,5-tetrahydro-1H-3-benzazepine;

Ex 106. 3-(3-{[5-(1-benzothien-3-yl)-4-methyl-4H-1,2,4-triazol-3-yl]thio}propyl)-7-(ethylsulfonyl)-2,3,4,5-tetrahydro-1H-3-benzazepine;

Ex 107. 7-(ethylsulfonyl)-3-(3-{[5-(1H-indol-4-yl)-4-methyl-4H-1,2,4-triazol-3-yl]thio}propyl)-2,3,4,5-tetrahydro-1H-3-benzazepine;

Ex 108. 7-(ethylsulfonyl)-3-(3-{[5-(3-(pyrazin-3-yl)phenyl]-4-methyl-4H-1,2,4-triazol-3-yl)thio}propyl)-2,3,4,5-tetrahydro-1H-3-benzazepine;

Ex 109. 7-(ethylsulfonyl)-3-(3-{[5-(1H-indol-7-yl)-4-methyl-4H-1,2,4-triazol-3-yl]thio}propyl)-2,3,4,5-tetrahydro-1H-3-benzazepine;

Ex 110. 4-[5-({3-[7-(ethylsulfonyl)-1,2,4,5-tetrahydro-3H-3-benzazepin-3-yl]propyl}thio)-4-methyl-4H-1,2,4-triazol-3-yl]benzonitrile;

Ex 111. 7-(ethylsulfonyl)-3-(3-{[4-methyl-5-(1-methyl-1H-indol-3-yl)-4H-1,2,4-triazol-3-yl]thio}propyl)-2,3,4,5-tetrahydro-1H-3-benzazepine;

Ex 112. 7-(ethylsulfonyl)-3-(3-{[4-methyl-5-(7-quinolinyl)-4H-1,2,4-triazol-3-yl]thio}propyl)-2,3,4,5-tetrahydro-1H-3-benzazepine;

Ex 113. 7-(ethylsulfonyl)-3-(3-{[4-(4-fluorophenyl)-1-methyl-1H-imidazol-2-yl]thio}propyl)-2,3,4,5-tetrahydro-1H-3-benzazepine;

Ex 114. 3-(3-{[5-(4-fluorophenyl)-4-methyl-4H-1,2,4-triazol-3-yl]thio}propyl)-7-(hexahydro-1H-azepin-1-ylsulfonyl)-2,3,4,5-tetrahydro-1H-3-benzazepine;

Ex 115. 7-(hexahydro-1H-azepin-1-ylsulfonyl)-3-(3-{[4-methyl-5-(6-quinolinyl)-4H-1,2,4-triazol-3-yl]thio}propyl)-2,3,4,5-tetrahydro-1H-3-benzazepine;

Ex 116. 7-(2-furanylsulfonyl)-3-(3-{[4-methyl-5-(2-methyl-6-quinolinyl)-4H-1,2,4-triazol-3-yl]thio}propyl)-2,3,4,5-tetrahydro-1H-3-benzazepine;

Ex 117. 3-(3-{[5-(4-fluorophenyl)-4-methyl-4H-1,2,4-triazol-3-yl]thio}propyl)-7-(2-furanylsulfonyl)-2,3,4,5-tetrahydro-1H-3-benzazepine;

Ex 118. 3-(3-{[5-(2,4-difluorophenyl)-4-methyl-4H-1,2,4-triazol-3-yl]thio}propyl)-7-(2-furanylsulfonyl)-2,3,4,5-tetrahydro-1H-3-benzazepine;

Ex 119. 7-(2-furanylsulfonyl)-3-(3-{[4-methyl-5-(6-quinolinyl)-4H-1,2,4-triazol-3-yl]thio}propyl)-2,3,4,5-tetrahydro-1H-3-benzazepine;

Ex 120. 3-(3-{[4-methyl-5-(4-quinolinyl)-4H-1,2,4-triazol-3-yl]thio}propyl)-2,3,4,5-tetrahydro-1H-3-benzazepin-7-yl methanesulfonate;

Ex 121. 3-(3-{[4-methyl-5-(6-quinolinyl)-4H-1,2,4-triazol-3-yl]thio}propyl)-7-(1-pyrrolidinylcarbonyl)-2,3,4,5-tetrahydro-1H-3-benzazepine;

Ex 122. 3-(3-{[4-methyl-5-(6-quinolinyl)-4H-1,2,4-triazol-3-yl]thio}propyl)-7-(1-piperidinylcarbonyl)-2,3,4,5-tetrahydro-1H-3-benzazepine;

Ex 123. N,N-diethyl-3-(3-{[4-methyl-5-(6-quinolinyl)-4H-1,2,4-triazol-3-yl]thio}propyl)-2,3,4,5-tetrahydro-1H-3-benzazepine-7-carboxamide;

Ex 124. (1E)-1-[3-(3-{[4-methyl-5-(6-quinolinyl)-4H-1,2,4-triazol-3-yl]thio}propyl)-2,3,4,5-tetrahydro-1H-3-benzazepin-7-yl]ethanone O-methyloxime;

Ex 125. 3-(3-{[5-(4-fluorophenyl)-4-methyl-4H-1,2,4-triazol-3-yl]thio}propyl)-7-(3-methyl-5-isoxazolyl)-2,3,4,5-tetrahydro-1H-3-benzazepine;

Ex 126. 7-(3-methyl-5-isoxazolyl)-3-(3-{[4-methyl-5-(6-quinolinyl)-4H-1,2,4-triazol-3-yl]thio}propyl)-2,3,4,5-tetrahydro-1H-3-benzazepine;

Ex 127. 7-(3-methyl-5-isoxazolyl)-3-(3-{[4-methyl-5-(2-methyl-5-quinolinyl)-4H-1,2,4-triazol-3-yl]thio}propyl)-2,3,4,5-tetrahydro-1H-3-benzazepine;

Ex 128. 7-(3-methyl-5-isoxazolyl)-3-(3-{[4-methyl-5-(2-methyl-6-quinolinyl)-4H-1,2,4-triazol-3-yl]thio}propyl)-2,3,4,5-tetrahydro-1H-3-benzazepine;

Ex 129. 3-(3-{[5-(2,4-difluorophenyl)-4-methyl-4H-1,2,4-triazol-3-yl]thio}propyl)-7-(3-methyl-5-isoxazolyl)-2,3,4,5-tetrahydro-1H-3-benzazepine;

Ex 130. 7-(5-methyl-3-isoxazolyl)-3-(3-{[4-methyl-5-(2-methyl-6-quinolinyl)-4H-1,2,4-triazol-3-yl]thio}propyl)-2,3,4,5-tetrahydro-1H-3-benzazepine;

Ex 131. 3-(3-{[5-(2,4-difluorophenyl)-4-methyl-4H-1,2,4-triazol-3-yl]thio}propyl)-7-(5-methyl-3-isoxazolyl)-2,3,4,5-tetrahydro-1H-3-benzazepine;

Ex 132. 3-(3-{[5-(1H-indol-5-yl)-4-methyl-4H-1,2,4-triazol-3-yl]thio}propyl)-7-(5-methyl-3-isoxazolyl)-2,3,4,5-tetrahydro-1H-3-benzazepine;

Ex 133. 7-(5-methyl-3-isoxazolyl)-3-(3-{[4-methyl-5-(2-methyl-5-quinolinyl)-4H-1,2,4-triazol-3-yl]thio}propyl)-2,3,4,5-tetrahydro-1H-3-benzazepine;

Ex 134. 7-(5-methyl-3-isoxazolyl)-3-(3-{[4-methyl-5-(1H-pyrrolo[2,3-b]pyridin-3-yl)-4H-1,2,4-triazol-3-yl]thio}propyl)-2,3,4,5-tetrahydro-1H-3-benzazepine;

Ex 135. 3-(3-{[5-(8-fluoro-5-quinolinyl)-4-methyl-4H-1,2,4-triazol-3-yl]thio}propyl)-7-(5-methyl-3-isoxazolyl)-2,3,4,5-tetrahydro-1H-3-benzazepine;

Ex 136. 3-{3-[(5-cyclohexyl-4-methyl-4H-1,2,4-triazol-3-yl)thio]propyl}-7-(5-methyl-3-isoxazolyl)-2,3,4,5-tetrahydro-1H-3-benzazepine;

Ex 137. 3-(3-{[5-(8-fluoro-2-methyl-5-quinolinyl)-4-methyl-4H-1,2,4-triazol-3-yl]thio}propyl)-7-(5-methyl-3-isoxazolyl)-2,3,4,5-tetrahydro-1H-3-benzazepine;

Ex 138. 4-[4-methyl-5-({3-[7-(5-methyl-3-isoxazolyl)-1,2,4,5-tetrahydro-3H-3-benzazepin-3-yl]propyl}thio)-4H-1,2,4-triazol-3-yl]benzonitrile;

Ex 139. 3-(3-{[5-(1-benzothien-2-yl)-4-methyl-4H-1,2,4-triazol-3-yl]thio}propyl)-7-(5-methyl-3-isoxazolyl)-2,3,4,5-tetrahydro-1H-3-benzazepine;

Ex 140. 3-(3-{[5-(1H-indol-6-yl)-4-methyl-4H-1,2,4-triazol-3-yl]thio}propyl)-7-(5-methyl-3-isoxazolyl)-2,3,4,5-tetrahydro-1H-3-benzazepine;

Ex 141. 7-(5-methyl-3-isoxazolyl)-3-(3-{[4-methyl-5-(2-naphthalenyl)-4H-1,2,4-triazol-3-yl]thio}propyl)-2,3,4,5-tetrahydro-1H-3-benzazepine;

Ex 142. 3-(3-{[5-(1-benzothien-3-yl)-4-methyl-4H-1,2,4-triazol-3-yl]thio}propyl)-7-(5-methyl-3-isoxazolyl)-2,3,4,5-tetrahydro-1H-3-benzazepine;

Ex 143. 3-(3-{[5-(2,3-dimethyl-6-quinoxalinyl)-4-methyl-4H-1,2,4-triazol-3-yl]thio}propyl)-7-(5-methyl-3-isoxazolyl)-2,3,4,5-tetrahydro-1H-3-benzazepine;

Ex 144. 3-(3-{[5-(1H-indol-4-yl)-4-methyl-4H-1,2,4-triazol-3-yl]thio}propyl)-7-(5-methyl-3-isoxazolyl)-2,3,4,5-tetrahydro-1H-3-benzazepine;

Ex 145. 3-[4-methyl-5-({3-[7-(5-methyl-3-isoxazolyl)-1,2,4,5-tetrahydro-3H-3-benzazepin-3-yl]propyl}thio)-4H-1,2,4-triazol-3-yl]benzonitrile;

Ex 146. 7-(5-methyl-3-isoxazolyl)-3-(3-{[4-methyl-5-(1,6-naphthyridin-2-yl)-4H-1,2,4-triazol-3-yl]thio}propyl)-2,3,4,5-tetrahydro-1H-3-benzazepine;

Ex 147. 3-(3-{[5-(1-benzofuran-4-yl)-4-methyl-4H-1,2,4-triazol-3-yl]thio}propyl)-7-(5-methyl-3-isoxazolyl)-2,3,4,5-tetrahydro-1H-3-benzazepine;

Ex 148. 7-(5-methyl-3-isoxazolyl)-3-(3-{[1-methyl-5-(6-quinolinyl)-1H-imidazol-2-yl]thio}propyl)-2,3,4,5-tetrahydro-1H-3-benzazepine;

Ex 149. 3-(3-{[5-(8-chloro-2-methyl-5-quinolinyl)-4-methyl-4H-1,2,4-triazol-3-yl]thio}propyl)-7-(5-methyl-3-isoxazolyl)-2,3,4,5-tetrahydro-1H-3-benzazepine;

Ex 150. 7-(5-methyl-3-isoxazolyl)-3-(3-{[4-methyl-5-(1-methyl-1H-indol-3-yl)-4H-1,2,4-triazol-3-yl]thio}propyl)-2,3,4,5-tetrahydro-1H-3-benzazepine;

Ex 151. 3-(3-{[5-(1-benzofuran-2-yl)-4-methyl-4H-1,2,4-triazol-3-yl]thio}propyl)-7-(5-methyl-3-isoxazolyl)-2,3,4,5-tetrahydro-1H-3-benzazepine;

Ex 152. 3-(3-{[5-(1-isoquinolinyl)-4-methyl-4H-1,2,4-triazol-3-yl]thio}propyl)-7-(5-methyl-3-isoxazolyl)-2,3,4,5-tetrahydro-1H-3-benzazepine;

Ex 153. 3-(3-{[5-(3-isoquinolinyl)-4-methyl-4H-1,2,4-triazol-3-yl]thio}propyl)-7-(5-methyl-3-isoxazolyl)-2,3,4,5-tetrahydro-1H-3-benzazepine;

Ex 154. 7-(5-methyl-3-isoxazolyl)-3-(3-{[4-methyl-5-(2-methyl-1,6-naphthyridin-3-yl)-4H-1,2,4-triazol-3-yl]thio}propyl)-2,3,4,5-tetrahydro-1H-3-benzazepine;

Ex 155. 7-(5-methyl-3-isoxazolyl)-3-(3-{[4-methyl-5-(1-methyl-1H-indol-2-yl)-4H-1,2,4-triazol-3-yl]thio}propyl)-2,3,4,5-tetrahydro-1H-3-benzazepine;

Ex 156. 3-(3-{[5-(1H-indol-2-yl)-4-methyl-4H-1,2,4-triazol-3-yl]thio}propyl)-7-(5-methyl-3-isoxazolyl)-2,3,4,5-tetrahydro-1H-3-benzazepine;

Ex 157. 7-(5-methyl-3-isoxazolyl)-3-(3-{[4-methyl-5-(2-quinolinyl)-4H-1,2,4-triazol-3-yl]thio}propyl)-2,3,4,5-tetrahydro-1H-3-benzazepine;

Ex 158. 7-(5-methyl-3-isoxazolyl)-3-(3-{[4-methyl-5-(2-quinoxalinyl)-4H-1,2,4-triazol-3-yl]thio}propyl)-2,3,4,5-tetrahydro-1H-3-benzazepine;

Ex 159. 3-(3-{[5-(5,6-dimethyl-3-pyridinyl)-4-methyl-4H-1,2,4-triazol-3-yl]thio}propyl)-7-(5-methyl-3-isoxazolyl)-2,3,4,5-tetrahydro-1H-3-benzazepine;

Ex 160. 7-(5-methyl-3-isoxazolyl)-3-(3-{[4-methyl-5-(1-naphthalenyl)-4H-1,2,4-triazol-3-yl]thio}propyl)-2,3,4,5-tetrahydro-1H-3-benzazepine;

Ex 161. 5-[4-methyl-5-({3-[7-(5-methyl-3-isoxazolyl)-1,2,4,5-tetrahydro-3H-3-benzazepin-3-yl]propyl}thio)-4H-1,2,4-triazol-3-yl]-2(1H)-quinolinone;

Ex 162. 3-(3-{[5-(1-benzofuran-7-yl)-4-methyl-4H-1,2,4-triazol-3-yl]thio}propyl)-7-(5-methyl-3-isoxazolyl)-2,3,4,5-tetrahydro-1H-3-benzazepine;

Ex 163. 7-(5-methyl-3-isoxazolyl)-3-(3-{[4-methyl-5-(6-quinoxalinyl)-4H-1,2,4-triazol-3-yl]thio}propyl)-2,3,4,5-tetrahydro-1H-3-benzazepine;

Ex 164. 7-(5-methyl-3-isoxazolyl)-3-(3-{[4-methyl-5-(8-quinolinyl)-4H-1,2,4-triazol-3-yl]thio}propyl)-2,3,4,5-tetrahydro-1H-3-benzazepine;

Ex 165. 3-(3-{[5-(5,6-dimethyl-2-pyridinyl)-4-methyl-4H-1,2,4-triazol-3-yl]thio}propyl)-7-(5-methyl-3-isoxazolyl)-2,3,4,5-tetrahydro-1H-3-benzazepine;

Ex 166. 3-(3-{[4-methyl-5-(2-methyl-6-quinolinyl)-4H-1,2,4-triazol-3-yl]thio}propyl)-7-(2-pyrazinyl)-2,3,4,5-tetrahydro-1H-3-benzazepine;

Ex 167. 3-(3-{[4-methyl-5-(2-methyl-5-quinolinyl)-4H-1,2,4-triazol-3-yl]thio}propyl)-7-(2-pyrazinyl)-2,3,4,5-tetrahydro-1H-3-benzazepine;

Ex 168. 3-(3-{[4-methyl-5-(2-methyl-6-quinolinyl)-4H-1,2,4-triazol-3-yl]thio}propyl)-7-(5-methyl-1,3-oxazol-2-yl)-2,3,4,5-tetrahydro-1H-3-benzazepine;

Ex 169. 3-(3-{[4-ethyl-5-(6-quinolinyl)-4H-1,2,4-triazol-3-yl]thio}propyl)-7-(5-methyl-1,3-oxazol-2-yl)-2,3,4,5-tetrahydro-1H-3-benzazepine;

Ex 170. 3-(3-{[5-(2,4-difluorophenyl)-4-methyl-4H-1,2,4-triazol-3-yl]thio}propyl)-7-(5-methyl-1,3-oxazol-2-yl)-2,3,4,5-tetrahydro-1H-3-benzazepine;

Ex 171. 3-(3-{[4-methyl-5-(2-methyl-5-quinolinyl)-4H-1,2,4-triazol-3-yl]thio}propyl)-7-(5-methyl-1,3-oxazol-2-yl)-2,3,4,5-tetrahydro-1H-3-benzazepine;

Ex 172. 7-(5-methyl-1,3-oxazol-2-yl)-3-(3-{[4-(2-propen-1-yl)-5-(6-quinolinyl)-4H-1,2,4-triazol-3-yl]thio}propyl)-2,3,4,5-tetrahydro-1H-3-benzazepine;

Ex 173. 7-(5-methyl-3-isoxazolyl)-3-{4-[4-methyl-5-(2-methyl-6-quinolinyl)-4H-1,2,4-triazol-3-yl]butyl}-2,3,4,5-tetrahydro-1H-3-benzazepine;

Ex 174. 3-{4-[5-(4-fluorophenyl)-4-methyl-4H-1,2,4-triazol-3-yl]butyl}-7-(5-methyl-3-isoxazolyl)-2,3,4,5-tetrahydro-1H-3-benzazepine;

Ex 175. 7-(ethylsulfonyl)-3-(4-{[4-methyl-5-(6-quinolinyl)-4H-1,2,4-triazol-3-yl]thio}butyl)-2,3,4,5-tetrahydro-1H-3-benzazepine;

Ex 176. 7-(5-methyl-3-isoxazolyl)-3-(4-{[4-methyl-5-(6-quinolinyl)-4H-1,2,4-triazol-3-yl]thio}butyl)-2,3,4,5-tetrahydro-1H-3-benzazepine;

Ex 177. 7-(3-methyl-5-isoxazolyl)-3-(4-{[4-methyl-5-(6-quinolinyl)-4H-1,2,4-triazol-3-yl]thio}butyl)-2,3,4,5-tetrahydro-1H-3-benzazepine;

or a salt thereof.

Note that in the above compound names, morpholine refers to 1,4-morpholine.

These compounds may for example be in the form of their free base or pharmaceutically (i.e. physiologically) acceptable salts thereof.

The present invention also provides a process for preparing a compound of formula (I) or a salt thereof wherein B is a sulfur atom and t is 3, i.e. a compound of formula (IA), which process comprises:

(a) reacting a compound of formula (II):

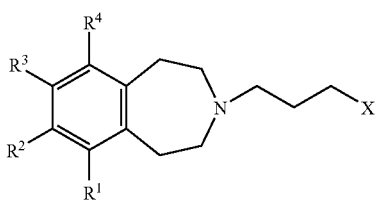

Formula (II)

wherein $R^1$ to $R^4$ are as herein defined and X is a leaving group; with a compound of formula (III):

A—SH                    Formula (III)

wherein A is as herein defined; or (b) to prepare a compound of formula (IA) wherein $R^2$ is $Ar^3$—Z and Z is a bond, reacting a compound of formula (IV):

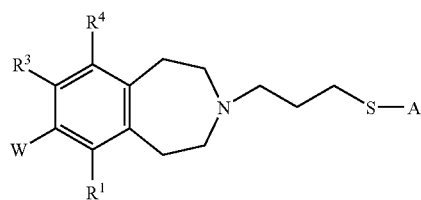

Formula (IV)

wherein $R^1$, $R^3$, $R^4$, and A are as herein defined and W is a halogen atom or a trifluoromethylsulfonyloxy group, or W is a group M selected from a boron derivative (e.g. a boronic acid function $B(OH)_2$) or a metal function such as trialkylstannyl (e.g.

$SnBu_3$), zinc halide or magnesium halide;

with a compound $Ar^3$—$W^1$, wherein $W^1$ is a halogen atom or a trifluoromethylsulfonyloxy group when W is a group M or $W^1$ is a group M as defined above when W is a halogen atom or a trifluoromethylsulfonyloxy group; or (c) to prepare a compound of formula (IA) wherein $R^3$ is $Ar^3$—Z and Z is O or S, reacting a compound of formula (V):

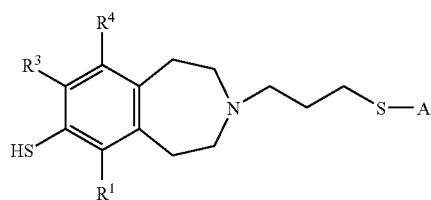

Formula (V)

wherein $R^1$, $R^3$, $R^4$ and A are as herein defined; with a reagent serving to introduce the group $Ar^3$; or (d) interconverting one compound of formula (IA) to a different compound of formula (I) e.g. by:

(i) converting one or more of $R^1$ to $R^4$ from alkoxy (e.g. methoxy) to hydroxy, (ii) converting one or more of $R^2$ or $R^3$ from hydroxy to sulfonyloxy, such as alkylsulfonyloxy e.g. methanesulfonyloxy or trifluoromethanesulfonyloxy, (iii) converting a compound in which A is substituted by one or more groups of the formula (b) as herein defined wherein Y represents S to a compound wherein Y is $SO_2$; or (iv) converting Y from CO to $CH_2$ in a compound in which A is substituted by one or more groups of the formula (b); or (e) to prepare a compound of formula (IA) where A is substituted by one or more groups of the formula (b) as herein defined where Y is a bond, reacting a compound of formula (VI):

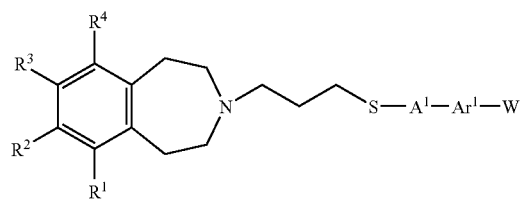

Formula (VI)

wherein $R^1$ to $R^4$ and $Ar^1$ are as herein defined, W is as defined in (c) above, and $A^1$ is the same as herein defined for group A but has a substituent $Ar^1$—W (illustrated) instead of one of the one or more substituents of formula (b) present in the product compound;

with a compound $Ar^2$—$W^1$, wherein $W^1$ is a halogen atom or a trifluoromethylsulfonyloxy group when W is a group M, or $W^1$ is a group M when W as defined in (c) above is a halogen atom or a trifluoromethylsulfonyloxy group;

and optionally thereafter forming a salt of formula (I).

Process (a) may be effected using conventional methods for the formation of a thioether. The leaving group X can be a halogen atom such as chlorine. Alternatively X can be a sulfonyloxy group such $C_{1-4}$alkylsulfonyloxy (e.g. methanesulfonyloxy or trifluoromethanesulfonyloxy); or $Ar^4$-sulfonyloxy wherein $Ar^4$ is optionally substituted phenyl, an optionally substituted 5- or 6-membered aromatic heterocyclic ring, or an optionally substituted bicyclic ring system, preferably optionally substituted phenyl, wherein in each case the optional substituents are one or more $C_{1-2}$alkyl groups; e.g. para-toluenesulfonyloxy. When X is a halogen the reaction may be carried out using a base such as lithium hydroxide in a solvent such as N,N-dimethylformamide.

The invention also provides a compound of formula (II):

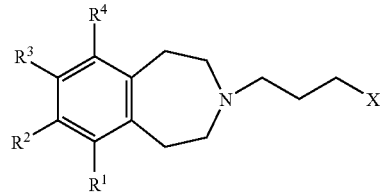

Formula (II)

wherein $R^1$ to $R^4$ are as herein defined, provided that $R^1$ to $R^4$ are not all H, and X is a leaving group. "Leaving group" is as understood by a skilled chemist, i.e. a group which can be displaced by a nucleophile in e.g. a $S_N^2$ or $S_N^1$ type reaction. X can be as hereinabove defined. Specific examples of interest are given in the Descriptions hereinafter.

Reaction of a compound of formula (IV) with $Ar^3$—$W^1$ according to process (b), or a compound of formula (VI) with $Ar^2$—$W^1$ according to process (e), may be effected in the presence of a transition metal e.g., palladium catalyst such as bis-triphenylphosphinepalladium dichloride or tetrakis-triphenylphosphinepalladium (0). When M represents a boronic acid function such as B(OH)$_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulfonyloxy group such as trifluoromethylsulfonyloxy; and W$^1$ is preferably a group M, such as trialkylstannyl or B(OH)$_2$.

In process (c) the reagent serving to introduce the group Ar$^3$ is preferably a compound of formula Ar$^3$—Hal, wherein Hal is a halogen atom. The reaction may be effected in the presence of a base, such as potassium carbonate, in a solvent such as N,N-dimethylformamide.

Interconversion reactions according to process (d) may be effected using methods well known in the art.

A compound of formula (II) may itself be prepared by reacting a compound of formula (VII):

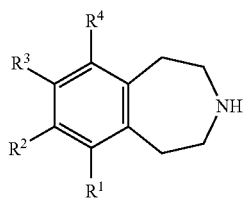

Formula (VII)

wherein R$^1$ to R$^4$ are as hereinbefore defined;
with a compound of formula (VIII):

LCH$_2$CH$_2$CH$_2$X    Formula (VIII)

wherein X is as herein defined and L is a leaving group, e.g., a bromine atom. For typical reaction conditions, see Description 20 hereinafter.

Compounds A—SH of formula (III) may be prepared by methods well known in the art (many such thiols are commercially available). Where the compound of formula (III) is HS-(1,2,4-triazolyl)-R$^7$ (

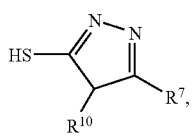

used to make compounds of Formula (IA); R$^{10}$ can for example be Me), this can be prepared from R$^7$—CO$_2$H or the corresponding ester or acid chloride by standard methods. For example, reaction of R$^7$—CO$_2$Et with hydrazine, followed by treatment of the resulting hydrazide with R$^{10}$—NCS (e.g. MeNCS) and cyclisation of the resulting R$^7$CONHNHC(=S)NH—R$^{10}$ under basic conditions gives the desired triazoles. Alternatively, reaction of R$^7$COCl with NH$_2$NHC(=S)NH—

R$^{10}$ in pyridine gives R$^7$CONHNHC(=S)NH—R$^{10}$ (J. Het. Chem., 1995, 32, 183; R$^{10}$=Me).

Where the compound of formula (III) is an imidazole such as

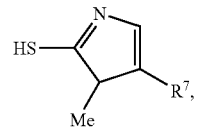

used to make the compounds of Formula (IB), the compound may be prepared by conversion of a ketone R$^7$COMe to R$^7$COCH$_2$NH$_2$ by standard methods and reacting the aminoketone with MeNCS (or other R$^{10}$—NCS) to give the desired imidazole (Acta. Chem. Scand., 1969, 23, 2879). Where the compound of formula (III) is an imidazole such as

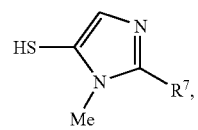

used to make the compounds of Formula (IC), the compound may be prepared either by chlorosulfonation of the parent imidazole, followed by reduction of the ClSO$_2$-group to the HS— group (J. Het. Chem., 1998, 35, 141), or by conversion of the corresponding imidazolone (Tetrahedron, 1989, 45, 6375) to the imidazolthione with for example P$_2$S$_5$ or Lawesson's reagent (J. Med. Chem., 1993, 36, 3371).

Compounds of formula (IV), (V) or (VI) may be prepared by processes analogous to (a), (b), (c), (d) and (e) described above. Compounds Ar$^2$W$^1$, Ar$^3$W$^1$ and Ar$^3$Hal are commercially available or may be prepared by standard methods.

Compounds of formula (VII), where for example R$^1$, R$^2$, R$^3$ or R$^4$ is a halogen, methoxy, acetyl, cyano, carboxylic acid or carboxamide group, are known in the literature (for example see M. Kanao et al., Chem. Pharm. Bull. 1982, 30, 180-188 for the synthesis of 7-methoxy-2,3,4,5-tetrahydro-1H-3-benzazepine; WO 00/21951; and N. E. Austin et al., Bioorg. Med. Chem. Lett., 2000, 10, 2553-2555) or may be prepared by methods well known in the art. Compounds of formula (VIII) are readily available or prepared by known methods. See also Descriptions 1-40 in WO 00/21951 for syntheses of many such compounds, which can be easily varied to achieve the synthesis of other related compounds of Formula (VII).

Conversion of a compound of formula (VII) where R$^2$ or R$^3$ is a cyano or acetyl group to a compound of formula (VII) where R$^2$ or R$^3$ is a group Ar$^3$Z, where Ar is an oxadiazole or an isoxazole ring and Z is a bond, may be carried out by (i) conversion of (VII) to a N-Boc protected compound of formula (IX), where R$^1$ to R$^4$ are as hereinbefore defined, using standard methods; (ii) conversion of R$^2$ or R$^3$ from cyano to oxadiazolyl using known methods, or conversion of acetyl to isoxazolyl using known methods; and (iii) deprotection of a compound of formula (IX) to a compound of formula (VII) using standard methods.

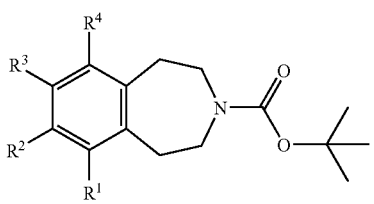

Formula (IX)

Certain specific compounds of Formula (VII), which are used as intermediates in the synthesis of specific examples of compounds of Formula (I) disclosed herein, are novel over the generalised disclosure in WO 00/21951. Hence, the present invention also provides a compound of Formula (X):

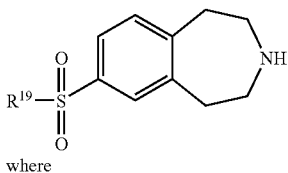

Formula (X)

where

R$^{19}$ = ethyl, N,N-dimethylamino, pyrollidin-1-yl ( N—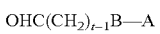 ), or 1,4-morpholin-4-yl ( or a secondary-amine-protected derivative thereof, or a salt of the compound or derivative. These compounds can be made for example according to Descriptions 15a, 21-22, 21-22(a) and 21-22(b) hereinafter. Suitable secondary amine protecting groups which can be present in the protected derivatives are known to the skilled chemist and include alkyloxycarbonyl (e.g. N-tert-butyloxycarbonyl, Boc) and alkanoyl (e.g. acetyl or trifluoroacetyl). The protected derivatives can be prepared using the standard protecting group chemistry on compound (X); for example by using the methods of Descriptions 3 (for Boc protection) or 12 (for acetyl protection) or by changing the protecting group used in the Descriptions (for other protecting groups).

The present invention also provides a compound of Formula (X$^1$):

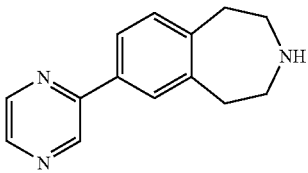

Formula (XI)

or a secondary-amine-protected derivative thereof, or a salt of the compound or derivative. These pyrazin-2-yl compounds and derivatives can be prepared for example by the methods of Descriptions 27 and 28.

The present invention also provides a process for preparing a compound of formula (I) or a salt thereof, which process comprises:

(a) reacting a compound of formula (VII):

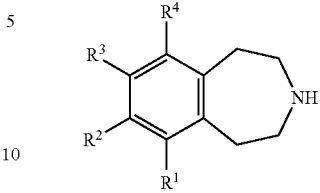

Formula (VII)

with a compounds of formula (XII):

OHC(CH$_2$)$_{t-1}$B—A  Formula (XII)

wherein R$^1$ to R$^4$, t, B and A are as herein defined. The reaction of a compound of Formula (VII) with a compound of Formula (XII) is carried out by a reductive amination by standard methods know to those skilled in the art, for example by the use of sodium triacetoxyborohydride in a solvent such as 1,2-dichloroethane. The aldehydes of Formula (XII) may be prepared by methods known in the art, for example by the procedure described herein for Examples 173 (parts a-f) and Example 175 (parts a and b).

Compounds of formula (I) have been found to exhibit affinity for dopamine receptors, in particular the D$_3$ receptor, and are expected to be useful in the treatment of disease states which require modulation of such receptors, such as psychotic conditions. Many of the compounds of formula (I) have also been found to have greater affinity for dopamine D$_3$ than for D$_2$ receptors. The therapeutic effect of currently available antipsychotic agents (neuroleptics) is generally believed to be exerted via blockade of D$_2$ receptors; however this mechanism is also thought to be responsible for undesirable extrapyramidal side effects (eps) associated with many neuroleptic agents. Without wishing to be bound by theory, it has been suggested that blockade of the recently characterised dopamine D$_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). Preferred compounds of the present invention are therefore those which have higher (e.g. $\geq$10× or $\geq$100× higher) affinity for dopamine D$_3$ than dopamine D$_2$ receptors (such affinity can be measured using standard methodology for example using cloned dopamine receptors—see herein). Said compounds may advantageously be used as selective modulators of D$_3$ receptors.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). From the localisation of D$_3$ receptors, it could also be envisaged that the compounds could also have utility for the treatment of substance abuse where it has been suggested that D3 receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. Such conditions in particular include psychoses/psychotic conditions such as schizophrenia, and substance abuse.

The invention also provides the use of a compound of formula (I) or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a pharmaceutically acceptable salt thereof for use in the treatment of a condition in a mammal for which modulation (especially antagonism/inhibition) of dopamine receptors (especially dopamine $D_3$ receptors) is beneficial.

A preferred use for $D_3$ antagonists according to the present invention is in the treatment of psychoses such as schizophrenia or in the treatment of substance abuse.

Thus, a still further aspect the invention provides a method of treating a psychotic condition (e.g. schizophrenia) or substance abuse which comprises administering to a mammal (e.g. human) in need thereof an effective amount of a compound of formula (I) as herein defined or a pharmaceutically acceptable salt thereof.

Also provided is the use of a compound of formula (I) or a pharmaceutically acceptable salt thereof in the manufacture of a medicament for the treatment of a psychotic condition (e.g. schizophrenia) or substance abuse in a mammal.

Also provided is a compound of formula (I) or a pharmaceutically acceptable salt thereof for use in the treatment of a psychotic condition (e.g. schizophrenia) or substance abuse in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomizing device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Binding Experiments on Cloned Dopamine (e.g. D2, D3 and D4) Receptors

The ability of the compounds to bind selectively to human D2/D3/D4 dopamine receptors can be demonstrated by measuring their binding to cloned receptors. The inhibition constants ($K_i$) of test compounds for displacement of [$^{125}$I]-Iodosulpride binding to human D2/D3 and [$^3$H]-YM-09151 to D4 dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −80° C. Crude cell membranes were prepared by homogenisation followed by high-speed centrifugation, and characterisation of cloned receptors achieved by radioligand binding.

Preparation of Cho Cell Membranes: Cell Pellets were Gently Thawed at Room temperature, and resuspended in about 20 volumes of ice-cold Extraction buffer; 5 mM EDTA, 50 mM Trizma pre-set crystals (pH7.4@37° C.), 1 mM $MgCl_2$, 5 mM KCl and 120 mM NaCl. The suspension was homogenised using an Ultra-Turrax at full speed for 15 seconds. The homogenate was centrifuged at 18,000 r.p.m for 15 min at 4° C. in a Sorvall RC5C centrifuge. Supernatant was discarded, and homogenate re-suspended in extraction buffer then centrifugation was repeated. The final pellet was resuspended in 50 mM Trizma pre-set crystals (pH 7.4 @ 37° C.) and stored in 1 ml aliquot tubes at −80° C. (D2=3.0E+08 cells, D3=7.0E+07 cells and D4=1.0E+08 cells). The protein content was determined using a BCA protocol and bovine serum albumin as a standard (Smith, P. K., et al., Measurement of protein using bicinchoninic acid. Anal. Biochem. 150, 76-85 (1985)).

Binding experiments: Crude D2/D3 cell membranes were incubated with 0.03 nM [$^{125}$I]-Iodosulpride (~2000 Ci/mmol; Amersham, U. K.) and D4 with 0.8 nM [$^3$H]-YM-09151 (~85 Ci/mmol; NEN, UK), and the test compound in a buffer containing 50 mM Trizma pre-set crystals (pH 7.4 @ 37° C.), 120 mM NaCl, 5 mM KCl, 2 mM $CaCl_2$, 1 mM $MgCl_2$, 0.3% (w/v) bovine serum albumin. The total volume is 0.2 ml and incubated in a water bath at 37° C. for 40 minutes. Following incubation, samples were filtered onto GF/B Unifilters using a Can berra Packard Filtermate, and washed four times with ice-cold 50 mM Trizma pre-set crystals (pH 7.4 @ 37° C.). The radioactivity on the filters was measured using a Canberra Packard Topcount Scintillation counter. Non-specific binding was defined with 10 µM SKF-102161 (YM-09151). For competition curves, 10 serial log concentrations of competing cold drug were used (Dilution range: 10 µM-10 pM). Competition curves were analysed using Inflexion, an iterative curve fitting programme in Excel. Results were expressed as pKi values where pKi=−log 10 [Ki].

The exemplified compounds have pKi values within the range of 7.5-9.5 at the dopamine D3 receptor. Selected especially preferred compounds are as follows, with pKi values between 8.0-9.5. pKi results are only estimated to be accurate to about ±0.2-0.3.

Examples: 1, 5, 8, 13, 14, 22, 51, 61, 63, 67, 70, 72, 74, 91, 93, 95, 96, 99, 100, 126, 130, 131, 133, 135, 137, 138, 143, 146, 168, 169, 173, 176.

Functional Activity at Cloned Dopamine Receptors

The functional activity of compounds at human D2 and human D3 receptors (i.e. agonism or antagonism) may be determined using a Cytosensor Microphysiometer (McConnell H M et al Science 1992 257 1906-1912). In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16-18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90 s. The pump was on for the first 60 s and the acidification rate determined between 68 and 88 s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995), Vol. 115, 160P]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

EXAMPLES

The invention is further illustrated by the following non-limiting examples:

Description 1

2,3,4,5-Tetrahydro-1H-3-benzazepine 1,2-Phenylenediacetonitrile (7.5 g, 48 mmol) dissolved in ethanol (150 ml) was added to Raney Ni (2 g) which had been previously washed with ethanol (3×20 ml). The mixture was then hydrogenated at 50° C. at 50 psi pressure with shaking for 24 h. The reaction mixture was then cooled to room temperature and filtered through a pad of kieselguhr and washed through with ethanol (100 ml). The filtrate was evaporated in vacuo to give a brown oil which was chromatographed on silica gel (100 g), eluting with 2-10% methanol in $CH_2Cl_2$ to give the title compound as a brown oil (2.45 g, 35%).

Mass spectrum (API$^+$) Found: 148 (MH$^+$). $C_{10}H_{13}N$ requires 147.

Description 2

7-Hydroxy-2,3,4,5-tetrahydro-1H-3-benzazepine, hydrobromide

7-Methoxy-2,3,4,5-tetrahydro-1H-3-benzazepine (10 g) (known from M. Kanao et al., *Chem. Pharm. Bull.* 1982, 30, 180-188) in 48% aqueous hydrobromic acid (350 ml) was allowed to stir at 100° C. for 4 h. The mixture was cooled to 20° C. then evaporated to dryness in vacuo to give the title compound (14.5 g) as a brown solid.

Mass spectrum (API$^+$): Found 164 (MH$^+$). $C_{10}H_{13}NO$ requires 163.

$^1$H NMR (DMSO) δ: 2.80-3.25 (8H, m), 4.42 (2H, br s), 6.50-6.70 (2H, m), 6.98 (1H, d, J=8 Hz), 8.86 (1H, br s).

Description 3

3-(tert-Butyloxycarbonyl)-7-hydroxy-2,3,4,5-tetrahydro-1H-3-benzazepine

To a solution of 7-hydroxy-2,3,4,5-tetrahydro-1H-3-benzazepine, hydrobromide (14.5 g) in tetrahydrofuran (100 ml) and water (70 ml), was added triethylamine (8 g), followed by a solution of di-tert-butyl dicarbonate (14 g) in THF (20 ml). The resulting mixture was allowed to stir at 20° C. for 16 h, partitioned between ethyl acetate (200 ml) and water (200 ml). The aqueous layer was washed with ethyl acetate (100 ml). The combined organic extracts were washed with saturated aqueous sodium bicarbonate (100 ml), dried ($Na_2SO_4$) and evaporated to dryness in vacuo. The resulting oil was purified by silica gel chromatography. Elution with ethyl acetate in hexane (10%-30%) gave the title compound (8 g).

Mass spectrum (API$^+$): Found 164 (MH$^+$-Boc). $C_{15}H_{21}NO_3$ requires 263.

$^1$H NMR (CDCl$_3$) δ: 1.48 (9H, s), 2.75-2.87 (4H, m), 3.40-3.60 (4H, m), 4.95 (1H, s), 6.50-6.62 (2H, m), 6.96 (1H, d, J=8 Hz).

Description 4

3-(tert-Butyloxycarbonyl)-7-trifluoromethylsulfonyloxy-2,3,4,5-tetrahydro-1H-3-benzazepine To a stirred mixture of 3-(tert-butyloxycarbonyl)-7-hydroxy-2,3,4,5-tetrahydro-1H-3-benzazepine (7 g) and triethylamine (5.4 ml) in dry dichloromethane under argon at −20° C., was added, dropwise, trifluoromethanesulfonic anhydride (5 ml). The resulting mixture was allowed to warm slowly to 20° C. over 16 h, then was poured into saturated aqueous sodium bicarbonate (200 ml) and extracted with dichloromethane (2×150 ml). The combined organic extracts were washed with brine (150 ml), dried ($Na_2SO_4$) and evaporated in vacuo to give an amber oil. Silica gel chromatography, eluting with ethyl acetate in hexane (10%-30%) gave the title compound (7 g) as an amber oil.

Mass spectrum (API$^+$): Found 396 (MH$^+$). $C_{16}H_{20}F_3NO_5S$ requires 395.

$^1$H NMR (CDCl$_3$) δ: 1.48 (9H, s), 2.85-2.95 (4H, m), 3.5-3.65 (4H, m), 7.00-7.05 (2H, m), 7.15-7.27 (1H, m).

Description 5

3-(tert-Butyloxycarbonyl)-7-cyano-2,3,4,5-tetrahydro-1H-3-benzazepine

A mixture of 3-(tert-butyloxycarbonyl)-7-trifluoromethylsulfonyloxy-2,3,4,5-tetrahydro-1H-3-benzazepine (4.78 g, 12.1 mmol), zinc cyanide (1.42 g, 15.6 mmol) and tetrakistriphenylphosphine palladium (0) (1.4 g, 1.2 mmol, 10 mol %), in dry dimethylformamide (50 ml) was stirred at 100° C. for 3 h under argon. After cooling to room temperature the reaction mixture was diluted with ethyl acetate (120 ml) and filtered. The filtrate was washed with saturated aqueous sodium bicarbonate (100 ml), then water (2×50 ml), then brine (50 ml). The organic layer was dried over sodium sulfate and evaporated in vacuo to give brown oil, which was purified by chromatography on silica gel with 20-100% ethyl acetate—hexane elution to give the title compound (0.765 g, 23%) as a brown oil.

Mass spectrum (API$^+$): Found 173 (MH$^+$-Boc). $C_{16}H_{20}N_2O_2$ requires 272.

$^1$H NMR (CDCl$_3$) δ: 1.47 (9H, s), 2.93 (4H, m), 3.56 (4H, m), 7.21 (1H, d, J=8 Hz), 7.42 (2H, m).

Description 6

7-Cyano-2,3,4,5-tetrahydro-1H-3-benzazepine

A mixture of 3-(tert-butyloxycarbonyl)-7-cyano-2,3,4,5-tetrahydro-1H-3-benzazepine (765 mg, 2.81 mmol) and trifluoroacetic acid (2 ml), in dichloromethane (20 ml) was stirred at 40° C. for 1 h. The reaction mixture was evaporated to dryness in vacuo and partitioned between ethyl acetate (50 ml) and water (50 ml). The aqueous layer was basified using potassium carbonate and re-extracted with ethyl acetate (2×30 ml). The combined basic organic extracts were dried over sodium sulfate and evaporated in vacuo to give the title compound as a colourless oil (212 mg, 44%).

Mass spectrum (API$^+$): Found 173 (MH$^+$). $C_{11}H_{12}N_2$ requires 172.

$^1$H NMR (CDCl$_3$) δ: 2.04 (1H, br s), 2.95 (8H, m), 7.18 (1H, d, J=8 Hz), 7.38 (2H, m).

Description 7

3-(tert-Butyloxycarbonyl)-7-(3-(5-methyl)-1,2,4-oxadiazolyl)-2,3,4,5-tetrahydro-1H-3-benzazepine To a suspension of sodium methoxide (0.6 g, 11 mmol) in anhydrous methanol (12 ml) under argon, was added hydroxylamine hydrochloride (0.76 g, 11 mmol), followed by 3-(tert-butyloxycarbonyl)-7-cyano-2,3,4,5-tetrahydro-1H-3-benzazepine (1.5 g, 5.5 mmol). The mixture was stirred under reflux for 16 h, then allowed to cool to room temperature. The methanol was evaporated in vacuo and the resulting residue partitioned between dichloromethane (100 ml) and water (100 ml). The aqueous layer was washed with more $CH_2Cl_2$ (100 ml). The combined organic extracts were dried and evaporated in vacuo to give a solid (1.8 g), which was mixed with acetic anhydride (15 ml) and heated at 120° C. for 2 h. Excess acetic anhydride was evaporated in vacuo and the resulting oily residue partitioned between $CH_2Cl_2$ (250 ml) and saturated sodium bicarbonate solution (250 ml). The organic layer was washed with more bicarbonate solution (200 ml), dried, and evaporated to give an oil. Gravity silica gel chromatography eluting with ethyl acetate in hexane gave the title compound (3.2 g, 73%) as a colourless oil.

¹H NMR (CDCl₃) δ: 1.49 (9H, s), 2.65 (3H, s), 2.96 (4H, m), 3.58 (4H, m), 7.22 (1H, d, J=8 Hz), 7.80 (2H, m).

Description 8

7-(3-(5-Methyl)-1,2,4-oxadiazolyl)-2,3,4,5-tetrahydro-1H-3-benzazepine

A solution of 3-(tert-butyloxycarbonyl)-7-(3-(5-methyl)-1,2,4-oxadiazolyl)-2,3,4,5-tetrahydro-1H-3-benzazepine (1.2 g, 3.6 mmol) in CH₂Cl₂ (15 ml) and trifluoroacetic acid (15 ml) was heater under reflux for 2 h. Solvent was evaporated in vacuo and the residue partitioned between diethyl ether (50 ml) and water (50 ml). The aqueous layer was saturated with potassium carbonate then extracted with CH₂Cl₂ (2×100 ml). The combined organic extracts were dried and evaporated in vacuo to give the title compound (0.74 g, 88%) as an oil.

Mass spectrum (API⁺): Found 230 (MH⁺). $C_{13}H_{15}N_3O$ requires 229.

¹H NMR (CDCl₃) δ: 1.80 (1H, br s), 2.65 (3H, s), 2.90-3.00 (8H, m), 7.20 (1H, d, J=8 Hz), 7.75-7.85 (2H, m).

Description 9

7-(3-(tert-Butyloxycarbonyl)-2,3,4,5-tetrahydro-1H-3-benzazepinyl)carboxamide

To a solution of 3-(tert-butyloxycarbonyl)-7-cyano-2,3,4,5-tetrahydro-1H-3-benzazepine (5.44 g, 20 mmol) cooled in ice bath, was added potassium carbonate (0.4 g) in water (1 ml), followed by dropwise addition of 30% w/w hydrogen peroxide (2.4 ml). The resulting mixture was stirred at 5° C. for 5 min, then the ice-bath was removed. After another 5 min, water (100 ml) was added. The solid precipitate was collected by filtration and dried to give the title compound (4.35 g, 75%) as a colourless solid.

¹H NMR (CDCl₃) δ: 1.48 (9H, s), 2.96 (4H, m), 3.56 (4H, m), 5.60-6.30 (2H, br d), 7.19 (1H, d, J=8 Hz), 7.50-7.80 (2H, m).

Description 10

3-(tert-Butyloxycarbonyl)-7-(5-(3-methyl)-1,2,4-oxadiazolyl)-2,3,4,5-tetrahydro-1H-3-benzazepine A mixture of 7-(3-(tert-butyloxycarbonyl)-2,3,4,5-tetrahydro-1H-3-benzazepinyl)carboxamide (4.29 g, 14.8 mmol) and N,N-dimethyl acetamide dimethyl acetal (6 ml, 41 mmol) was heated at 125° C. under argon. Methanol was removed from the reaction by means of a distillation condenser over 2 h. The reaction mixture was further evaporated in vacuo to give a thick brown oily residue. To this residue was added, in order, dioxan (10 ml), 5M sodium hydroxide (4 ml), hydroxylamine hydrochloride (1.4 g, 20 mmol) and 70% aqueous acetic acid (20 ml). The combined mixture was allowed to stir at room temperature for 15 min and then at 90° C. for 1 h. The mixture was treated with water (100 ml) and extracted with CH₂Cl₂ (2×150 ml). Combined organic extracts were washed with saturated sodium bicarbonate (100 ml), dried and evaporated in vacuo to give an oil. Gravity silica gel chromatography, eluting with ethyl acetate in hexane, gave the title compound (3.9 g, 80%) as a colourless solid.

¹H NMR (CDCl₃) δ: 1.49 (9H, s), 2.47 (3H, s), 2.98 (4H, m), 3.60 (4H, m), 7.27 (1H, d, J=8 Hz), 7.80-7.90 (2H, m).

Description 11

7-(5-(3-Methyl)-1,2,4-oxadiazolyl)-2,3,4,5-tetrahydro-1H-3-benzazepine

A solution of 3-(tert-butyloxycarbonyl)-7-(5-(3-methyl)-1,2,4-oxadiazolyl)-2,3,4,5-tetrahydro-1H-3-benzazepine (3.8 g, 11.6 mmol) in CH₂Cl₂ (50 ml) and trifluoroacetic acid (12 ml) was heated under reflux for 2 h. Solvent was evaporated in vacuo and the residue partitioned between diethyl ether (200 ml) and water (200 ml). The aqueous layer was saturated with potassium carbonate then extracted with CH₂Cl₂ (3×200 ml). The combined organic extracts were dried and evaporated in vacuo to give the title compound (2.4 g, 91%) as a colourless solid.

Mass spectrum (API⁺): Found 230 (MH⁺). $C_{13}H_{15}N_3O$ requires 229.

¹H NMR (CDCl₃) δ: 1.86 (1H, br s), 2.47 (3H, s), 3.00 (8H, m), 7.25 (1H, d, J=8 Hz), 7.80-7.90 (2H, m).

Description 12

3-Acetyl-2,3,4,5-tetrahydro-1H-3-benzazepine

A solution of acetic anhydride (6.37 g, 0.062 mol) in dichloromethane (50 ml) was added dropwise to a stirred solution of 2,3,4,5-tetrahydro-1H-3-benzazepine (8.35 g, 0.057 mol) and triethylamine (8.7 ml) in dichloromethane (50 ml) at 0° C. under argon. After stirring at room temperature for 18 h, water (80 ml) was added and the organic layer separated. The organic layer was washed with 0.5 M hydrochloric acid (50 ml), saturated sodium bicarbonate solution (50 ml), water (50 ml) and then dried (Na₂SO₄). Evaporation of the solvent in vacuo gave the title compound (10.24 g, 95%) as a yellow oil which solidified on standing.

¹H NMR (CDCl₃) δ: 2.18 (3H, s), 2.85-3.00 (4H, m), 3.55-3.60 (2H, m), 3.72-3.80 (2H, m), 7.10-7.20 (4H, m).

Mass Spectrum AP⁺: Found 190 (MH⁺). $C_{12}H_{15}NO$ requires 189.

Description 13

3-Acetyl-7-chlorosulfonyl-2,3,4,5-tetrahydro-1H-3-benzazepine

A solution of 3-acetyl-2,3,4,5-tetrahydro-1H-3-benzazepine (4.0 g, 0.021 mol) in dichloromethane (25 ml) was added dropwise to a stirred solution of chlorosulphonic acid in dichloromethane (25 ml) at −70° C. under argon. After warming to room temperature, the reaction was stirred for 18 h before being quenched in ice/water (200 ml). The resulting mixture was extracted with ethyl acetate (3×100 ml), dried (Na₂SO₄) and the solvent evaporated in vacuo to give the title compound (2.74 g, 45%) as a pale yellow solid.

¹H NMR: δ (CDCl₃): 2.21 (3H, s), 3.0-3.10 (4H, m), 3.60-3.70 (2H, m), 3.74-3.80 (2H, m), 7.35-7.40 (1H, m), 7.80-7.85 (2H, m).

Mass spectrum AP⁺: Found 288 & 290 (MH⁺). $C_{12}H_{14}NSO_2Cl$ requires 287 & 289.

Description 14

3-Acetyl-7-methylsulfonyl-2,3,4,5-tetrahydro-1H-3-benzazepine

To a stirred solution of sodium sulphite (1.60 g, 12.6 mmol) and sodium hydrogen carbonate (1.14 g, 13.56 mmol) in water (25 ml) was added 3-acetyl-7-chlorosulfonyl-2,3,4,5-tetrahydro-1H-3-benzazepine (2.6 g, 9.04 mmol) in tetrahydrofuran (10 ml). The reaction mixture was then heated at 75° C. for 2 h, cooled to 30° C. and methyl iodide (2.8 ml, 45.20 mmol) added. After stirring at 50° C. for 24 h, the reaction mixture was cooled to room temperature and partitioned between water (50 ml) and ethyl acetate (100 ml). The aqueous layer was then separated and further extracted with ethyl acetate (2×80 ml). The combined organics were then dried ($Na_2SO_4$) and the solvent removed in vacuo to give the title compound (1.77 g, 73%) as a pale yellow solid.

$^1$H NMR ($CDCl_3$) 2.20 (3H, s), 2.99-3.05 (4H, m), 3.06 (3H, s), 3.61-3.64 (2H, m), 3.73-3.77 (2H, m), 7.32-7.37 (1H, m), 7.7-7.75 (2H, m).

Mass Spectrum $AP^+$: Found 268 ($MH^+$). $C_{13}H_{17}NSO_3$ requires 267.

Description 15

7-Methylsulfonyl-2,3,4,5-tetrahydro-1H-3-benzazepine

A solution of 3-acetyl-7-methylsulfonyl-2,3,4,5-tetrahydro-1H-3-benzazepine (1.75 g, 6.55 mmol) in 5 M hydrochloric acid was heated at reflux for 18 h. The reaction mixture was then cooled to room temperature, basified to pH=12 with potassium carbonate and the solvent evaporated in vacuo. The solid residue was then extracted with ethyl acetate (5×60 ml) and the combined organics dried ($Na_2SO_4$). The solvent was then evaporated in vacuo to give the title compound (450 mg, 32%) as a pale yellow oil.

$^1$H NMR ($CDCl_3$) 1.88 (1H, br s), 2.95-3.13 (8H, m), 3.04 (3H, s), 7.25-7.30 (1H, d), 7.65-7.72 (2H, m).

Mass Spectrum $AP^+$: Found 226 ($MH^+$). $C_{11}H_{15}NSO_2$ requires 225.

Description 15a

7-Ethylsulfonyl-2,3,4,5-tetrahydro-1H-3-benzazepine

This compound was prepared in a similar manner to Descriptions 14 and 15, using ethyl iodide instead of methyl iodide.

Mass Spectrum $AP^+$: Found 240 ($MH^+$). $C_{12}H_{17}NSO_2$ requires 239.

Description 16

3-Trifluoracetyl-7-(5-methyl-isoxazol-3-yl)-2,3,4,5-tetrahydro-1H-3-benzazepine (a) Trifluoroacetic anhydride (13.2 ml) was added to a solution of 7-cyano-2,3,4,5-tetrahydro-1H-3-benzazepine (14.5 g) and triethylamine (14.2 ml) in dichloromethane (300 ml) at 0° C. The reaction mixture was allowed to warm to room temperature over 1.5 h, then washed with saturated sodium bicarbonate solution (300 ml), the organic layer dried and evaporated to give 3-trifluoracetyl-7-cyano-2,3,4,5-tetrahydro-1H-3-benzazepine as a yellow oil (20.3 g).

(b) 3-Trifluoracetyl-7-cyano-2,3,4,5-tetrahydro-1H-3-benzazepine (20.3 g) and nickel-aluminium alloy (35.5 g) in 75% aq. formic acid (400 ml) were heated at 80° C. for 3 h. The reaction was allowed to cool, filtered and the filtrate extracted with ethyl acetate. The combined organic layers were washed with saturated sodium bicarbonate solution, dried and evaporated to give 3-trifluoracetyl-2,3,4,5-tetrahydro-1H-3-benzazepine-7-carbaldehyde (20.0 g) as a yellow oil.

(c) 3-Trifluoracetyl-2,3,4,5-tetrahydro-1H-3-benzazepine-7-carbaldehyde (20.0 g) and hydroxylamine hydrochloride (6.1 g) in pyridine (140 ml) were stirred overnight and the reaction then evaporated in vacuo. The residue was partitioned between ethyl acetate and 10% sodium carbonate solution and the combined organic layers dried and evaporated to give 3-trifluoracetyl-2,3,4,5-tetrahydro-1H-3-benzazepine-7-carbaldehyde oxime (17.2 g) as a yellow solid.

(d) To a solution of 3-Trifluoracetyl-2,3,4,5-tetrahydro-1H-3-benzazepine-7-carbaldehyde oxime (17.2 g) in chloroform (700 ml) was added N-bromosuccinimide (11.8 g), portionwise over 5 min., and the mixture stirred for 1.5 h. 2-Chloropropene (30.3 ml) was added and the reaction cooled to −20° C. Triethylamine (25.1 ml) in chloroform was added over 10 min. and the reaction stirred at room temperature for 18 h. The solution was washed with 2M HCl, dried and evaporated and the residue chromatographed on Si gel, gradient eluting with 10-20% EtOAc in hexane to give the title compound (7.1 g) as a yellow oil.

Mass spectrum ($AP^+$): Found 325 [$MH^+$] $C_{16}H_{15}N_2O_2F_3$ requires 324.

Description 17

7-(5-Methyl-isoxazol-3-yl)-2,3,4,5-tetrahydro-1H-3-benzazepine

A mixture of 3-trifluoracetyl-7-(5-methyl-isoxazol-3-yl)-2,3,4,5-tetrahydro-1H-3-benzazepine (7.1 g) and $K_2CO_3$ (12.1 g) in 1:1 methanol:water (400 ml) was heated at 50° C. for 1 h. The mixture was cooled, poured into water (500 ml) and extracted with dichloromethane. The combined organic layers were dried and evaporated in vacuo to give the title compound as a yellow oil (3.9 g).

Mass spectrum ($AP^+$): Found 229 [$MH^+$] $C_{14}H_{16}N_2O$ requires 228.

Description 17a 7-(5-Methyl-isoxazol-3-yl)-2,3,4,5-tetrahydro-1H-3-benzazepine hydrochloride a) 7-(1-Hydroxyimino-ethyl)-1,2,4,5-tetrahydro-benzo[d]azepine-3-carboxylic acid tert-butyl ester 7-Acetyl-3-(tert-butyloxycarbonyl)-2,3,4,5-tetrahydro-1H-3-benzazepine (8.9 g, 30.8 mmol) was dissolved in pyridine (30 ml) and hydroxylamine hydrochloride (2.3 g, 33 mmol) was added and the mixture stirred for 2 h at room temperature. The solvent was evaporated and hexane (300 ml) and water (100 ml) were added and the colourless precipitate was filtered and washed with hexane (3×100 ml). The compound was dried in vacuo to give the title compound (6.23 g, 66%).

Mass Spectrum $AP^+$: Found 205 ([M-Boc]$^+$). $C_{17}H_{24}N_2O_3$ requires 304.

b) 7-(5-Methyl-isoxazol-3-yl)-1,2,4,5-tetrahydro-benzo[d] azepine-3-carboxylic acid tert-butyl ester 7-(1-Hydroxyimino-ethyl)-1,2,4,5-tetrahydro-benzo[d] azepine-3-carboxylic acid tert-butyl ester (2.89 g, 9.5 mmol) was cooled to 0° C. in tetrahydrofuran (70 ml) under argon. Butyllithium (7.6 ml, 2.5M in hexane, 19 mmol) was added dropwise to give an orange solution which was stirred for 1 h. N-Methyl-N-methoxy acetamide (824 mg, 8 mmol) was added dropwise in tetrahydrofuran (30 ml) over 3 min. The mixture was stirred for 1 h and then poured into water (27 ml) and concentrated sulphuric acid (3 ml). The resulting mixture was heated to reflux for 1 h and then cooled and neutralised with solid sodium bicarbonate. The mixture was partitioned between dichloromethane (200 ml) and water (100 ml) and the layers separated. The aqueous portion was extracted with dichloromethane (2×100 ml) and the combined organic extracts were evaporated. The residue was treated with dichloromethane (50 ml) and di-tert-butyl dicarbonate (2.18 g, 10 mmol) and the mixture stirred for 20 min, washed with water (50 ml) and evaporated. The residue was treated with pyridine (10 ml) and hydroxylamine hydrochloride (0.77 g, 11 mmol) and the mixture stirred for 1 h. The solvent was evaporated and the residue dissolved in dichloromethane (50 ml) which was washed with dilute hydrochloric acid (3×50 ml, 0.5M). The solvent was evaporated and the residue was purified by silica gel chromatography (eluent dichloromethane) which gave the title compound as a colourless solid (447 mg, 61%).

Mass Spectrum AP$^+$: Found 229 ([M-Boc]$^+$). $C_{19}H_{24}N_2O_3$ requires 328.

c) 7-(5-Methyl-isoxazol-3-yl)-2,3,4,5-tetrahydro-1H-3-benzazepine hydrochloride 7-(5-Methyl-isoxazol-3-yl)-1,2,4,5-tetrahydro-benzo[d] azepine-3-carboxylic acid tert-butyl ester (1.9 g, 5.8 mmol) was treated with ethanol (20 ml) followed by a saturated ethanolic hydrochloride solution (20 ml). The mixture was stirred for 12 h until a precipitate was observed. Diethyl ether (100 ml) was added and the precipitate filtered and dried in vacuo to give the title compound as a colourless solid (1.25 g, 81%).

Mass Spectrum AP$^+$: Found 229 ([M+H]$^+$). $C_{14}H_{16}N_2O$ requires 228.

$^1$H NMR (MeOD) δ: 2.47 (3H, s), 3.20 (4H, m), 3.33 (4H, m), 6.55 (1H, s), 7.34 (1H, d, J=8 Hz), 7.64 (1H, d, J=8 Hz), 7.68 (1H, s).

Description 18

3-(tert-Butyloxycarbonyl)-7-methanesulfonyloxy-2, 3,4,5-tetrahydro-1H-3-benzazepine A solution of 3-(tert-butyloxycarbonyl)-7-hydroxy-2,3,4, 5-tetrahydro-1H-3-benzazepine (3.0 g, 0.011 mol), methanesulfonylchloride (1.44 g, 0.013 mol), triethylamine (1.27 g, 0.013 mol) and dichloromethane (50 ml) was stirred at room temperature for 18 h. The reaction mixture was then partitioned between dichloromethane (50 ml) and a saturated solution of sodium hydrogen carbonate (50 ml). The organic layer was separated, washed with water (50 ml) and then dried (Na$_2$SO$_4$). The solvent was then evaporated in vacuo to give the title compound (3.85 g, 99%) as a pale yellow oil.

$^1$H NMR (CDCl$_3$) δ: 1.48 (9H, s), 2.86-2.92 (4H, m), 3.13 (3H, s), 3.53-3.56 (4H, m), 7.00-7.03 (2H, m), 7.13-7.16 (1H, m).

Mass spectrum (AP$^+$): Found 242 [M-BOC]H$^+$. $C_{16}H_{23}NSO_5$ requires 341.

Description 19

7-Methanesulfonyloxy-2,3,4,5-tetrahydro-1H-3-benzazepine

A solution of 3-(tert-butyloxycarbonyl)-7-methanesulfonyloxy-2,3,4,5-tetrahydro-1H-3-benzazepine (3.8 g, 0.011 mol), trifluoroacetic acid (3.76 g, 0.033 mol) and dichloromethane (50 ml) was heated at 50° C. for 5 h. The solvents were then evaporated in vacuo and the residue partitioned between water (200 ml) and ethyl acetate (150 ml). The aqueous layer was removed and washed with ethyl acetate (100 ml) and then basified to pH 14 with 40% sodium hydroxide. The suspension was then extracted with ethyl acetate (3×150 ml) and the combined organic layers dried (Na$_2$SO$_4$). The solvents were evaporated in vacuo to give the title compound (2.15 g, 80%) as a colourless oil.

$^1$H NMR (CDCl$_3$) δ: 2.88-3.00 (8H, m), 3.13 (3H, s), 6.99-7.03 (2H, m), 7.12 (1H, d).

Mass spectrum (AP$^+$): Found 242 (MH)$^+$. $C_{11}H_{15}NSO_3$ requires 241.

Description 20

3-(3-Chloropropyl)-7-methanesulfonyloxy-2,3,4,5-tetrahydro-1H-3-benzazepine

A mixture of 7-methanesulfonyloxy-2,3,4,5-tetrahydro-1H-3-benzazepine (1.75 g, 7.3 mmol), 1-bromo-3-chloropropane (0.80 ml, 8.1 mmol) and triethylamine (3 ml, 21.5 mmol) in anhydrous tetrahydrofuran (25 ml) was heated at reflux for 5 h. The mixture was cooled, evaporated in vacuo and the residue partitioned between water (100 ml) and ethyl acetate (100 ml). The aqueous layer was extracted with ethyl acetate (100 ml) and the combined organics washed with brine (150 ml), dried (Na$_2$SO$_4$) and evaporated in vacuo. Purification by chromatography on silica gel using 10-70% ethyl acetate in hexane gradient elution gave the title compound as a pale orange oil (1.22 g, 53%).

Mass spectrum (API$^+$): Found 318 (MH$^+$). $C_{14}H_{20}^{35}ClNO_3S$ requires 317.

$^1$H NMR δ 1.85-2.05 (2H, m), 2.55-2.70 (6H, m), 2.85-2.95 (4H, m), 3.12 (3H, s), 3.60-3.66 (2H, t, J=6.5 Hz), 6.95-7.15 (3H, m).

The following compounds were prepared in a similar manner to Description 20:

(a) 3-(3-Chloropropyl)-7-cyano-2,3,4,5-tetrahydro-1H-3-benzazepine

Mass spectrum (API$^+$): Found 249 (MH$^+$). $C_{14}H_{17}^{35}ClN_2$ requires 248. Prepared from the compound of Description 6

(b) 3-(3-Chloropropyl)-7-(5-methyl-1,2,4-oxadiazol-3-yl)-2,3,4,5-tetrahydro-1H-3-benzazepine Mass spectrum (API$^+$): Found 306 (MH$^+$). $C_{16}H_{20}^{35}ClN_3O$ requires 305. Prepared from the compound of Description 8.

(c) 3-(3-Chloropropyl)-7-methylsulfonyl-2,3,4,5-tetrahydro-1H-3-benzazepine

Mass spectrum (API$^+$): Found 302 (MH$^+$). $C_{14}H_{20}^{35}ClNO_2S$ requires 301. Prepared from the compound of Description 15.

(d) 3-(3-Chloropropyl)-7-(morpholin-4-yl)sulfonyl-2,3,4,5-tetrahydro-1H-3-benzazepine Mass spectrum (API$^+$): Found 373 (MH$^+$). $C_{17}H_{25}{}^{35}ClN_2O_3S$ requires 372. Prepared from the compound of Description 22.

(e) 3-(3-Chloropropyl)-7-(5-methyl-oxazol-2-yl)-2,3,4,5-tetrahydro-1H-3-benzazepine Mass spectrum (API$^+$): Found 305 (MH$^+$). $C_{17}H_{21}{}^{35}ClN_2O$ requires 304. Prepared from the compound of Description 25.

(f) 3-(3-Chloropropyl)-7-ethylsulfonyl-2,3,4,5-tetrahydro-1H-3-benzazepine

Mass spectrum (API$^+$): Found 316 (MH$^+$). $C_{15}H_{22}{}^{35}ClNO_2S$ requires 315. Prepared from the compound of Description 15a.

(g) 3-(3-Chloropropyl)-7-(pyrrolidine-1-sulfonyl)-2,3,4,5-tetrahydro-1H-3-benzazepine Mass spectrum (API$^+$): Found 357 (MH$^+$). $C_{17}H_{25}{}^{35}ClN_2O_2S$ requires 356. Prepared from the compound of Description 22(a).

(h) 3-(3-Chloropropyl)-2,3,4,5-tetrahydro-1H-3-benzazepine-7-sulfonic acid dimethylamide Mass spectrum (API$^+$): Found 331 (MH$^+$). $C_{15}H_{23}{}^{35}ClN_2O_2S$ requires 330. Prepared from the compound of Description 22(b).

(i) 3-(3-Chloropropyl)-7-pyrazin-2-yl-2,3,4,5-tetrahydro-1H-3-benzazepine

Mass spectrum (API$^+$): Found 302 (MH$^+$). $C_{17}H_{20}{}^{35}ClN_3$ requires 301. Prepared from the compound of Description 28.

(j) 3-(3-Chloropropyl)-7-(5-methyl-isoxazol-3-yl)-2,3,4,5-tetrahydro-1H-3-benzazepine Mass spectrum (API$^+$): Found 305 (MH$^+$). $C_{17}H_{21}{}^{35}ClN_2O$ requires 304. Prepared from the compound of Description 17.

Description 21

3-Acetyl-7-(morpholin-4-yl)sulfonyl-2,3,4,5-tetrahydro-1H-3-benzazepine

A mixture of 3-acetyl-7-chlorosulfonyl-2,3,4,5-tetrahydro-1H-3-benzazepine (4.0 g, 13.9 mmol), morpholine (1.8 ml, 20.8 mmol) and triethylamine (2.14 ml, 15.3 mmol) in tetrahydrofuran (120 ml) was heated at 60° C. for 3 h. The reaction mixture was then cooled, filtered and the filtrate evaporated in vacuo to give a yellow solid. Crystallisation from dichloromethane/n-hexane gave the title compound as an off-white solid (4.4 g, 94 Mass Spectrum AP$^+$: Found 339 (MH$^+$). $C_{16}H_{22}N_2SO_4$ requires 338.

Description 22

7-(Morpholin-4-yl)sulfonyl-2,3,4,5-tetrahydro-1H-3-benzazepine

A solution of 3-acetyl-7-(morpholin-4-yl)sulfonyl-2,3,4,5-tetrahydro-1H-3-benzazepine (3.0 g, 8.9 mmol) in 5 M hydrochloric acid was heated at reflux for 18 h. The reaction mixture was then cooled to room temperature, basified to pH=12 with potassium carbonate and the solvent evaporated in vacuo. The solid residue was then extracted with ethyl acetate (5×100 ml) and the combined organics dried (Na$_2$SO$_4$). The solvent was then evaporated in vacuo to give the title compound (1.49 g, 57%) as a pale yellow oil.

Mass Spectrum AP$^+$: Found 297 (MH$^+$). $C_{14}H_{20}N_2SO_3$ requires 296.

The following compounds were prepared in a similar manner to Descriptions 21 and 22:

(a) 7-(Pyrrolidine-1-sulfonyl)-2,3,4,5-tetrahydro-1H-3-benzazepine

Mass Spectrum AP$^+$: Found 281 (MH$^+$). $C_{14}H_{20}N_2SO_2$ requires 280. Prepared using pyrollidine instead of morpholine in Description 21.

(b) 2,3,4,5-Tetrahydro-1H-3-benzazepine-7-sulfonic acid dimethylamide

Mass Spectrum AP$^+$: Found 255 (MH$^+$). $C_{12}H_{18}N_2SO_2$ requires 254. Prepared using dimethylamine instead of morpholine in Description 21.

Description 23

3-(tert-Butyloxycarbonyl)-2,3,4,5-tetrahydro-1H-3-benzazepine-7-carboxylic acid prop-2-ynyl amide A mixture of 3-(tert-butyloxycarbonyl)-7-cyano-2,3,4,5-tetrahydro-1H-3-benzazepine (10 g, 37 mmol) and KOH (4.1 g, 73 mmol) in EtOH (100 ml) and water (20 ml) was heated under reflux for 24 h. Mixture allowed to cool and evaporated in vacuo and the residue redissolved in water (150 ml). The solution was acidified to pH4 and the precipitate filtered and dried. The crude acid (5 g, 17 mmol) was then dissolved in dichloromethane (100 ml), under Argon and propargylamine (0.77 g, 14 mmol), EDC (2.9 g 15 mmol) and HOBT (200 mg) added and the reaction stirred for 18 h. Saturated NaHCO$_3$ solution (100 ml) was added and the organic layer separated. The aqueous layer was re-extracted with dichloromethane and the combined organic layers dried and evaporated in vacuo. The residue was purified by silica gel chromatography (gradient elution, hexane/ethyl acetate) to give the title compound (3.8 g) as a colourless solid.

Mass Spectrum AP$^+$: Found 327 ([M–H]$^+$). $C_{19}H_{24}N_2O_3$ requires 328.

Description 24

3-(tert-Butyloxycarbonyl)-7-(5-methyl-oxazol-2-yl)-2,3,4,5-tetrahydro-1H-3-benzazepine A mixture of 2,3,4,5-tetrahydro-1H-3-benzazepine-7-carboxylic acid prop-2-ynyl amide (3.8 g) and mercury (II) acetate (350 mg) in glacial acetic acid was heated under reflux for 1.5 h. After cooling, the solvent was removed in vacuo and the residue partitioned between EtOAc (200 ml) and saturated NaHCO$_3$ solution (100 ml). The aqueous layer was re-extracted with EtOAc and the combined organic layers dried and evaporated in vacuo. The residue was purified using silica gel chromatography (gradient elution, hexane/EtOAc) to give the title compound (2.35 g) as a colourless oil.

Mass Spectrum AP$^+$: Found 229 ([M-Boc]$^+$). $C_{19}H_{24}N_2O_3$ requires 328.

Description 25

7-(5-Methyl-oxazol-2-yl)-2,3,4,5-tetrahydro-1H-3-benzazepine

Prepared from Description 24 by a similar procedure to that of Description 6.

Mass Spectrum AP$^+$: Found 229 (MH$^+$). $C_{14}H_{16}N_2O$ requires 228.

Description 26

7-Acetyl-3-(tert-butyloxycarbonyl)-2,3,4,5-tetrahydro-1H-3-benzazepine

To a stirred solution of 3-(tert-butyloxycarbonyl)-7-trifluoromethylsulfonyloxy-2,3,4,5-tetrahydro-1H-3-benzazepine (10 g, 25.3 mmol) in anhydrous dimethylformamide (100 ml) under argon at room temperature, was added triethylamine (7.05 ml, 50.6 mmol), butyl vinyl ether (16.4 ml, 126.6 mmol), 1,3-bis(diphenylphosphino)propane (0.412 g, 1 mmol) and palladium acetate (0.202 g, 0.9 mmol) sequentially. The resultant mixture was heated at 85° C. for 1.5 h and cooled to room temperature. 4% Aqueous hydrochloric acid (150 ml) was added and stirring continued for 0.5 h. The reaction mixture was extracted with dichloromethane (3×300 ml) and the combined organics washed with water (4×500 ml), dried (Na$_2$SO$_4$) and evaporated in vacuo to afford a brown gum. Chromatography on silica gel with 0-30% ethyl acetate—hexane gradient elution gave the title compound (5.8 g, 79%) as a colourless solid.

$^1$H NMR (CDCl$_3$) δ: 1.49 (9H, s), 2.58 (3H, s), 2.96 (4H, m), 3.57 (4H, m), 7.21 (1H, d, J=8 Hz), 7.72 (2H, m).

Description 27

3-(tert-Butyloxycarbonyl)-7-(pyrazin-2-yl)-2,3,4,5-tetrahydro-1H-3-benzazepine

To a stirred solution of 7-acetyl-3-(tert-butyloxycarbonyl)-2,3,4,5-tetrahydro-1H-3-benzazepine (12 g, 42 mmol) in dioxan (60 ml) was added selenium dioxide (4.61 g, 42 mmol) in dioxan (60 ml) and water (15 ml). The mixture was heated under reflux for 18 h., cooled and the solid residue filtered. The filtrate was evaporated in vacuo and the residue azeotroped with toluene to give an orange gum which was dissolved in ethanol and added dropwise to a stirred solution of ethylenediamine (3 g, 50 mmol) in ethanol at 0° C. After the addition was complete, KOH (2.6 g, 46 mmol) was added and the reaction heated under reflux for 3 h. The reaction mixture was then allowed to cool and evaporated in vacuo. The residue was partitioned between water and dichloromethane and the combined organic extracts dried and evaporated in vacuo to give a brown gum. Purification by silica gel chromatography (eluant 20% EtOAc:hexane) gave the title compound as a yellow oil (3.5 g).

Mass Spectrum AP$^+$: Found 226 ([M-Boc]$^+$). $C_{19}H_{23}N_3O_2$ requires 325.

Description 28

7-(Pyrazin-2-yl)-2,3,4,5-tetrahydro-1H-3-benzazepine

Prepared from Description 27 by a similar procedure to that of Description 6.

Mass Spectrum AP$^+$: Found 226 (MH$^+$). $C_{14}H_{14}N_3$ requires 225.

Description 29

5-Isoquinolin-1-yl-4-methyl-4H-[1,2,4]triazole-3-thiol

Hydroxybenzotriazole (0.078 g), 1-(3-dimethylaminopropyl)-3-ethylcarbodiimide hydrochloride (0.11 g) and triethylamine were added successively to a cooled solution (0° C.) of 4-methyl-3-thiosemicarbazide (0.061 g) and 1-isoquinoline carboxylic acid (0.10 g) in dimethylformamide (3 ml). Following addition the cooling bath was removed and the mixture was stirred at room temperature over night and then the reaction mixture was evaporated to dryness. To the residue was added sodium hydroxide solution (0.5 M, 5 ml) and the mixture was stirred at 80° C. for 3 h. The mixture was cooled to room temperature and the pH adjusted to pH 6 using hydrochloric acid solution (2M) and the resulting precipitate was filtered and dried in vacuo to give the title compound (0.11 g, 78%) as an off-white solid.

Mass Spectrum AP$^+$: Found 243 ([MH]$^+$). $C_{12}H_{10}N_4S$ requires 242.

$^1$H NMR (DMSO) δ: 3.65 (3H, s), 7.78 (1H, t, J=8 Hz), 7.89 (1H, t, J=8 Hz), 8.08 (1H, d, J=6 Hz), 8.13 (1H, d, J=8 Hz), 8.51 (1H, d, J=8 Hz), 8.71 (1H, d, J=6 Hz), 14.21 (1H, br s).

Examples

The Compounds of Examples tabulated below were all prepared using the following general method:—

A mixture of the appropriate chloropropyl benzazepine from Description 20 (1.57 mmol), appropriate thiol (1.57 mmol) and lithium hydroxide (1.57 mmol) in anhydrous DMF (5 ml) were heated at 100° C. for 2 h. The cooled reaction mixture was partitioned between water and ethyl acetate, the organic layer dried (Na$_2$SO$_4$) and evaporated in vacuo. Chromatography on silica gel using 30-100% ethyl acetate in hexane gradient elution gave the title compounds.

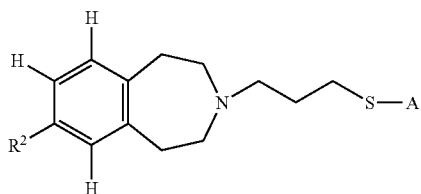

| Example | R² | A | Data |
|---|---|---|---|
| 1 | MeSO₂O— | 5-methyl-3-phenyl-4-methyl-1,2,4-triazol-yl | Mass spectrum (API⁺): Found 473 (MH⁺). C₂₃H₂₈N₄O₃S₂ required 472. ¹H NMR δ: 1.95-2.10(2H, m), 2.60-2.70(6H, m), 2.85-2.95(4H, m), 3.12(3H, s), 3.30-3.34(2H, t, J=7.2Hz), 3.60(3H, s), 6.95-7.05(2H, m), 7.05-7.15(1H, m), 7.45-7.55(3H, m), 7.60-7.70(2H, m). |
| 2 | NC— | 5-methyl-3-phenyl-4-methyl-1,2,4-triazol-yl | Mass spectrum (API⁺): Found 404(MH⁺). C₂₃H₂₅N₅S requires 403. |
| 3 | 3,5-dimethyl-1,2,4-oxadiazol-yl | 5-methyl-3-phenyl-4-methyl-1,2,4-triazol-yl | Mass spectrum (API⁺): Found 461(MH⁺). C₂₅H₂₈N₆OS requires 460. |
| 4 | MeSO₂— | 5-methyl-3-phenyl-4-methyl-1,2,4-triazol-yl | Mass spectrum (API⁺): Found 457(MH⁺). C₂₃H₂₈N₄O₂S₂ requires 456. |
| 5 | MeSO₂— | 3,4-diphenyl-5-methyl-1H-pyrazol-yl | Mass spectrum (API⁺): Found 518(MH⁺). C₂₉H₃₁N₃O₂S₂ requires 517. |
| 6 | MeSO₂— | 5-methyl-3-(quinolin-6-yl)-4-methyl-1,2,4-triazol-yl | Mass spectrum (API⁺): Found 508(MH⁺). C₂₆H₂₉N₅O₂S₂ requires 507. |
| 7 | MeSO₂O— | 5-methyl-3-(furan-2-yl)-4-methyl-1,2,4-triazol-yl | Mass spectrum (API⁺): Found 463(MH⁺). C₂₁H₂₆N₄O₄S₂ requires 462. |
| 8 | MeSO₂O— | 5-methyl-3-(thiophen-2-yl)-4-methyl-1,2,4-triazol-yl | Mass spectrum (API⁺): Found 479(MH⁺). C₂₁H₂₆N₄O₃S₃ requires 478. |
| 9 | MeSO₂O— | 5-methyl-3-(pyridin-4-yl)-4-methyl-1,2,4-triazol-yl | Mass spectrum (API⁺): Found 474(MH⁺). C₂₂H₂₇N₅O₃S₂ requires 473. |

-continued

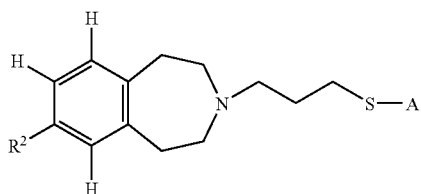

| Example | R² | A | Data |
|---|---|---|---|
| 10 | MeSO₂O— | 3-(4-tert-butylphenyl)-4,5-dimethyl-1,2,4-triazole | Mass spectrum (API⁺): Found 529(MH⁺). $C_{27}H_{36}N_4O_3S_2$ requires 528. |
| 11 | MeSO₂O— | 3-(5-methylisoxazol-3-yl)-4,5-dimethyl-1,2,4-triazole | Mass spectrum (API⁺): Found 478(MH⁺). $C_{21}H_{27}N_5O_4S_2$ requires 477. |
| 12 | MeSO₂O— | 3-(2,4-dichlorophenyl)-4,5-dimethyl-1,2,4-triazole | Mass spectrum (API⁺): Found 541(MH⁺). $C_{23}H_{26}{}^{35}Cl_2N_4O_3S_2$ requires 540. |
| 13 | MeSO₂O— | 3-(quinolin-6-yl)-4,5-dimethyl-1,2,4-triazole | Mass spectrum (API⁺): Found 524(MH⁺). $C_{26}H_{29}N_5O_3S_2$ requires 523. |
| 14 | MeSO₂O— | 3-(4-fluorophenyl)-4,5-dimethyl-1,2,4-triazole | Mass spectrum (API⁺): Found 491(MH⁺). $C_{23}H_{27}FN_4O_3S_2$ requires 490. |
| 15 | MeSO₂O— | 3-(4-trifluoromethylphenyl)-4,5-dimethyl-1,2,4-triazole | Mass spectrum (API⁺): Found 541(MH⁺). $C_{24}H_{27}F_3N_4O_3S_2$ requires 540. |
| 16 | MeSO₂O— | 5-(4-chlorophenyl)-1,2-dimethylimidazole | Mass spectrum (API⁺): Found 506(MH⁺). $C_{24}H_{28}{}^{35}ClN_3O_3S_2$ requires 505. |
| 17 | MeSO₂O— | 2-phenyl-5-methyl-1,3,4-oxadiazole | Mass spectrum (API⁺): Found 460(MH⁺). $C_{22}H_{25}N_3O_4S_2$ requires 459. |
| 18 | MeSO₂O— | 2-methylbenzoxazole | Mass spectrum (API⁺): Found 433(MH⁺). $C_{21}H_{24}N_2O_4S_2$ requires 432. |

-continued

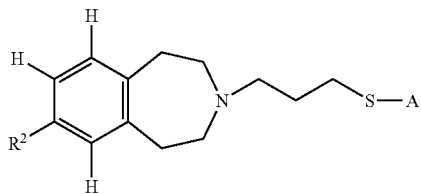

| Example | R² | A | Data |
|---|---|---|---|
| 19 | MeSO₂O— | 3,4-dimethyl-4H-1,2,4-triazol-5-yl | Mass spectrum (API⁺): Found 397(MH⁺). C₁₇H₂₄N₄O₃S₂ requires 396. |
| 20 | MeSO₂O— | 1,2-dimethyl-1H-imidazol-5-yl | Mass spectrum (API⁺): Found 396(MH⁺). C₁₈H₂₅N₃O₃S₂ requires 395. |
| 21 | MeSO₂O— | 2,3,5-trimethylfuran-4-yl | Mass spectrum (API⁺): Found 410(MH⁺). C₂₀H₂₇NO₄S₂ requires 409. |
| 22 | MeSO₂O— | 2-methyl-4,5-diphenyl-1H-imidazol-1-yl | Mass spectrum (API⁺): Found 534(MH⁺). C₂₉H₃₁N₃O₃S₂ requires 533. |
| 23 | MeSO₂O— | benzimidazol-2-yl | Mass spectrum (API⁺): Found 432(MH⁺). C₂₁H₂₅N₃O₃S₂ requires 431. |
| 24 | MeSO₂O— | pyridin-2-yl | Mass spectrum (API⁺): Found 393(MH⁺). C₁₉H₂₄N₂O₃S₂ requires 392. |
| 25 | MeSO₂O— | pyrimidin-2-yl | Mass spectrum (API⁺): Found 394(MH⁺). C₁₈H₂₃N₃O₃S₂ requires 393. |
| 26 | MeSO₂O— | quinolin-2-yl | Mass spectrum (API⁺): Found 443(MH⁺). C₂₃H₂₆N₂O₃S₂ requires 442. |
| 27 | MeSO₂O— | 4-(trifluoromethyl)pyrimidin-2-yl | Mass spectrum (API⁺): Found 462(MH⁺). C₁₉H₂₂F₃N₃O₃S₂ requires 461. |
| 28 | MeSO₂O— | 4-phenylpyrimidin-2-yl | Mass spectrum (API⁺): Found 470(MH⁺). C₂₄H₂₇N₃O₃S₂ requires 469. |

-continued

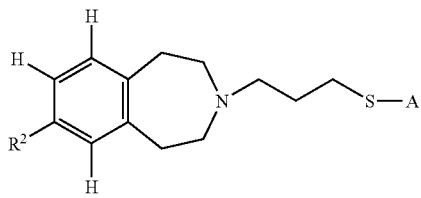

| Example | R² | A | Data |
|---|---|---|---|
| 29 | MeSO₂O— | 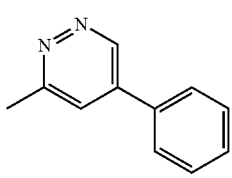 | Mass spectrum (API⁺): Found 470(MH⁺). $C_{24}H_{27}N_3O_3S_2$ requires 469. |
| 30 | MeSO₂O— | 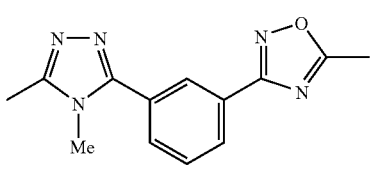 | Mass spectrum (API⁺): Found 555(MH⁺). $C_{26}H_{30}N_6O_4S_2$ requires 554. |
| 31 | MeSO₂O— | 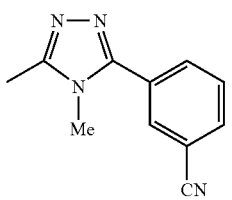 | Mass spectrum (API⁺): Found 498(MH⁺). $C_{24}H_{27}N_5O_3S_2$ requires 497. |
| 32 | MeSO₂O— | 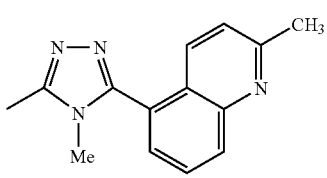 | Mass spectrum (API⁺): Found 598(MH⁺). $C_{27}H_{31}N_5O_3S_2$ requires 537. |
| 33 | MeSO₂O— | 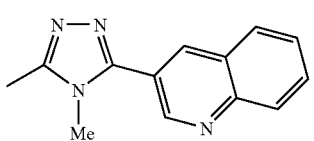 | Mass spectrum (API⁺): Found 524(MH⁺). $C_{26}H_{29}N_5O_3S_2$ requires 523. |
| 34 | MeSO₂O— | 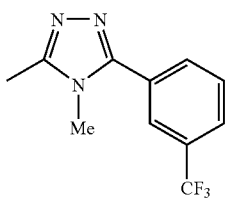 | Mass spectrum (API⁺): Found 541(MH⁺). $C_{24}H_{27}F_3N_4O_3S_2$ requires 540. |
| 35 | MeSO₂O— | 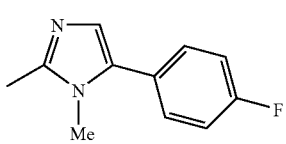 | Mass spectrum (API⁺): Found 490(MH⁺). $C_{24}H_{28}FN_3O_3S_2$ requires 489. |

-continued

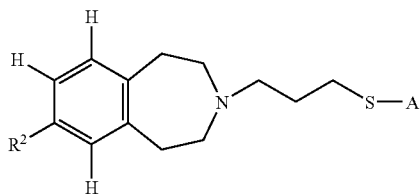

| Example | R² | A | Data |
|---|---|---|---|
| 36 | MeSO₂O— | 2-methyl-4,5-diphenyl-1-methyl-imidazole | Mass spectrum (API⁺): Found 548(MH⁺). $C_{30}H_{33}N_3O_3S_2$ requires 547. |
| 37 | MeSO₂O— | 5-methyl-3-(2-fluorophenyl)-4-methyl-1,2,4-triazole | Mass spectrum (API⁺): Found 491(MH⁺). $C_{23}H_{27}FN_4O_3S_2$ requires 490. |
| 38 | MeSO₂O— | 5-methyl-3-(3-fluorophenyl)-4-methyl-1,2,4-triazole | Mass spectrum (API⁺): Found 491(MH⁺). $C_{23}H_{27}FN_4O_3S_2$ requires 490. |
| 39 | MeSO₂O— | 5-methyl-3-(3,4-difluorophenyl)-4-methyl-1,2,4-triazole | Mass spectrum (API⁺): Found 509(MH⁺). $C_{23}H_{26}F_2N_4O_3S_2$ requires 508. |
| 40 | MeSO₂O— | 5-methyl-3-cyclohexyl-4-methyl-1,2,4-triazole | Mass spectrum (API⁺): Found 479(MH⁺). $C_{23}H_{34}N_4O_3S_2$ requires 478. |
| 41 | MeSO₂O— | 5-methyl-3-(4-fluorophenyl)-4-methyl-1,2,4-triazole | Mass spectrum (API⁺): Found 475(MH⁺). $C_{23}H_{27}FN_4O_2S_2$ requires 474. |
| 42 | MeSO₂O— | 2-methyl-4-phenyl-thiazole | Mass spectrum (API⁺): Found 459(MH⁺). $C_{23}H_{26}N_2O_2S_2$ requires 458. |
| 43 | MeSO₂O— | 5-methyl-3-[(E)-2-(4-fluorophenyl)vinyl]-4-methyl-1,2,4-triazole | Mass spectrum (API⁺): Found 501(MH⁺). $C_{25}H_{29}FN_4O_2S_2$ requires 500. |

-continued

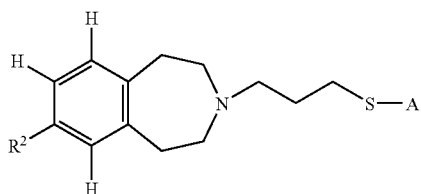

| Example | R² | A | Data |
|---|---|---|---|
| 44 | EtSO₂— | 5-methyl-4-methyl-3-(4-fluorophenyl)-1,2,4-triazole | Mass spectrum (API⁺): Found 489(MH⁺). $C_{24}H_{29}FN_4O_2S_2$ requires 488. |
| 45 | EtSO₂— | 5-methyl-4-methyl-3-(quinolin-6-yl)-1,2,4-triazole | Mass spectrum (API⁺): Found 522(MH⁺). $C_{27}H_{31}N_5O_2S_2$ requires 521. |
| 46 | EtSO₂— | 5-methyl-1-methyl-2-phenylimidazole | Mass spectrum (API⁺): Found 470(MH⁺). $C_{25}H_{31}N_3O_2S_2$ requires 469. |
| 47 | pyrrolidin-NSO₂- | 5-methyl-4-methyl-3-(4-fluorophenyl)-1,2,4-triazole | Mass spectrum (API⁺): Found 530(MH⁺). $C_{26}H_{32}FN_5O_2S_2$ requires 529. |
| 48 | pyrrolidin-NSO₂- | 5-methyl-4-methyl-3-(quinolin-6-yl)-1,2,4-triazole | Mass spectrum (API⁺): Found 563(MH⁺). $C_{29}H_{34}N_6O_2S_2$ requires 562. |
| 49 | pyrrolidin-NSO₂- | 2-methyl-4,5-diphenylimidazole | Mass spectrum (API⁺): Found 573(MH⁺). $C_{32}H_{36}N_4O_2S_2$ requires 572. |
| 50 | morpholin-NSO₂- | 5-methyl-4-methyl-3-(4-fluorophenyl)-1,2,4-triazole | Mass spectrum (API⁺): Found 546(MH⁺). $C_{26}H_{32}FN_5O_3S_2$ requires 545. |
| 51 | morpholin-NSO₂- | 5-methyl-4-methyl-3-(quinolin-6-yl)-1,2,4-triazole | Mass spectrum (API⁺): Found 579(MH⁺). $C_{29}H_{34}N_6O_3S_2$ requires 578. |
| 52 | 3-methylpyrazin-2-yl | 5-methyl-4-methyl-3-(4-fluorophenyl)-1,2,4-triazole | Mass spectrum (API⁺): Found 475(MH⁺). $C_{26}H_{27}FN_6S$ requires 474. |

-continued

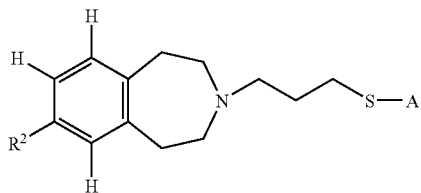

| Example | R² | A | Data |
|---|---|---|---|
| 53 | 3-methylpyrazin-2-yl | 5-methyl-4-methyl-3-(quinolin-6-yl)-4H-1,2,4-triazol-3-yl | Mass spectrum (API⁺): Found 508(MH⁺). $C_{29}H_{29}N_7S$ requires 507. |
| 54 | Me₂NSO₂— | 5-methyl-4-methyl-3-(4-fluorophenyl)-4H-1,2,4-triazol-3-yl | Mass spectrum (API⁺): Found 504(MH⁺). $C_{24}H_{30}FN_5O_2S_2$ requires 503. |
| 55 | Me₂NSO₂— | 5-methyl-4-methyl-3-(quinolin-6-yl)-4H-1,2,4-triazol-3-yl | Mass spectrum (API⁺): Found 537(MH⁺). $C_{27}H_{32}N_6O_2S_2$ requires 536. |
| 56 | MeSO₂— | 5-methyl-4-methyl-3-(quinolin-4-yl)-4H-1,2,4-triazol-3-yl | Mass spectrum (API⁺): Found 508(MH⁺). $C_{26}H_{29}N_5O_2S_2$ requires 507. |
| 57 | EtSO₂— | 5-methyl-4-methyl-3-[3-(5-methyl-1,3,4-oxadiazol-2-yl)phenyl]-4H-1,2,4-triazol-3-yl | Mass spectrum (API⁺): Found 553(MH⁺). $C_{27}H_{32}N_6O_3S_2$ requires 552. |
| 58 | EtSO₂— | 5-methyl-4-methyl-3-(3-methylquinolin-6-yl)-4H-1,2,4-triazol-3-yl | Mass spectrum (API⁺): Found 536(MH⁺). $C_{28}H_{33}N_5O_2S_2$ requires 535. |
| 59 | EtSO₂— | 5-methyl-4-methyl-3-[(E)-2-(4-fluorophenyl)ethenyl]-4H-1,2,4-triazol-3-yl | Mass spectrum (API⁺): Found 515(MH⁺). $C_{26}H_{31}FN_4O_2S_2$ requires 514. |
| 60 | 2,5-dimethyloxazol-4-yl | 5-methyl-4-methyl-3-(4-fluorophenyl)-4H-1,2,4-triazol-3-yl | Mass spectrum (API⁺): Found 478(MH⁺). $C_{26}H_{28}FN_5OS$ requires 477. |

-continued

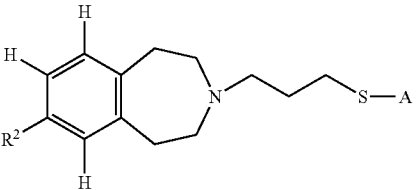

| Example | R² | A | Data |
|---|---|---|---|
| 61 | 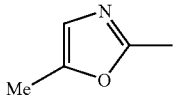 | 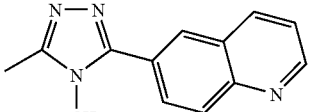 | Mass spectrum (API⁺): Found 511(MH⁺). $C_{29}H_{30}N_6OS$ requires 510. |
| 62 | 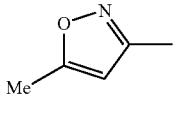 | 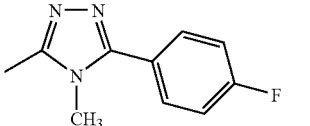 | Mass spectrum (API⁺): Found 478(MH⁺). $C_{26}H_{28}FN_5OS$ requires 477. |
| 63 | 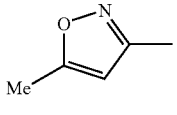 | 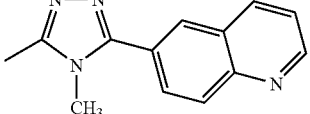 | Mass spectrum (API⁺): Found 511(MH⁺). $C_{29}H_{30}N_6OS$ requires 510. |
| 64 | 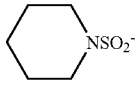 | 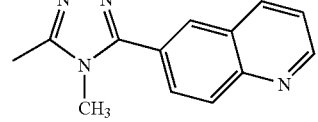 | Mass spectrum (API⁺): Found 577(MH⁺). $C_{30}H_{36}N_6O_2S_2$ requires 576. |
| 65 | 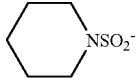 | 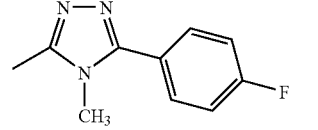 | Mass spectrum (API⁺): Found 544(MH⁺). $C_{27}H_{34}FN_5O_2S_2$ requires 543. |
| 66 | PhSO₂— | 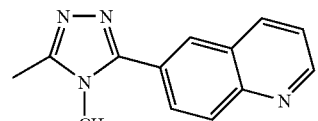 | Mass spectrum (API⁺): Found 570(MH⁺). $C_{31}H_{31}N_5O_2S_2$ requires 569. |
| 67 | PhSO₂— | 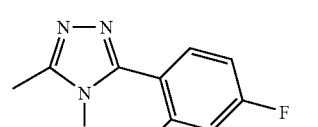 | Mass spectrum (API⁺): Found 555(MH⁺). $C_{28}H_{28}F_2N_4O_2S_2$ requires 554. |
| 68 | PhSO₂— | 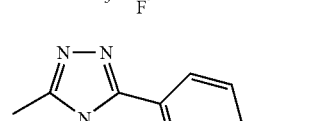 | Mass spectrum (API⁺): Found 537(MH⁺). $C_{28}H_{29}FN_4O_2S_2$ requires 536. |
| 69 | 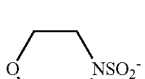 | 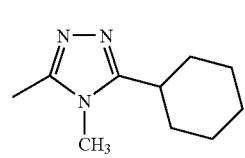 | Mass spectrum (API⁺): Found 534(MH⁺). $C_{26}H_{39}N_2O_3S_2$ requires 533. |

-continued

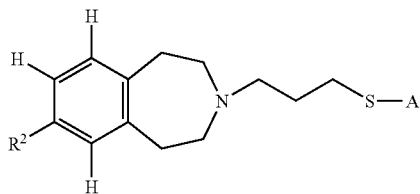

| Example | R² | A | Data |
|---|---|---|---|
| 70 | 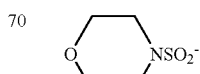 | 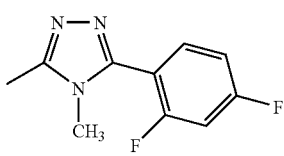 | Mass spectrum (API⁺): Found 564(MH⁺). $C_{26}H_{31}F_2N_5O_3S_2$ requires 563. |
| 71 | 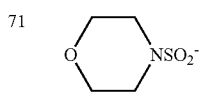 | 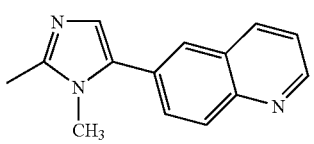 | Mass spectrum (API⁺): Found 578(MH⁺). $C_{30}H_{35}N_5O_3S_2$ requires 577. |
| 72 | MeSO₂— | 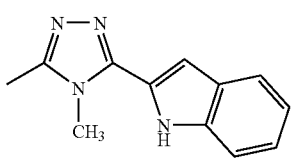 | Mass spectrum (API⁺): Found 496(MH⁺). $C_{25}H_{29}N_5O_2S_2$ requires 495. |
| 73 | MeSO₂— | 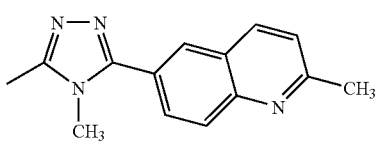 | Mass spectrum (API⁺): Found 522(MH⁺). $C_{27}H_{31}N_5O_2S_2$ requires 521. |
| 74 | MeSO₂— | 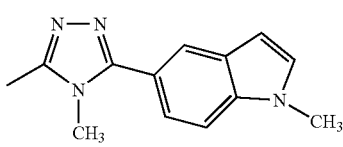 | Mass spectrum (API⁺): Found 510(MH⁺). $C_{26}H_{31}N_5O_2S_2$ requires 509. |
| 75 | MeSO₂— | 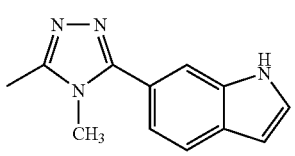 | Mass spectrum (API⁺): Found 496(MH⁺). $C_{25}H_{29}N_5O_2S_2$ requires 495. |
| 76 | MeSO₂— | 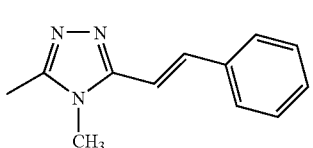 | Mass spectrum (API⁺): Found 501(MH⁺). $C_{25}H_{29}FN_4O_2S_2$ requires 500. |
| 77 | MeSO₂— | 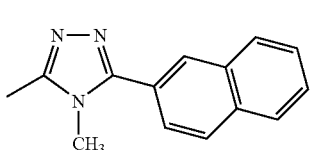 | Mass spectrum (API⁺): Found 507(MH⁺). $C_{27}H_{30}N_4O_2S_2$ requires 506. |

-continued

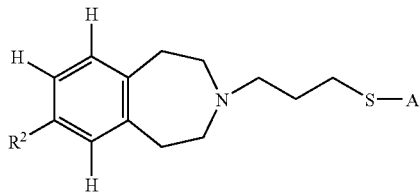

| Example | R² | A | Data |
|---------|-----|---|------|
| 78 | MeSO₂— | 4-methyl-5-methyl-3-(benzothiophen-2-yl)-1,2,4-triazole | Mass spectrum (API⁺): Found 513(MH⁺). C$_{25}$H$_{28}$N$_4$O$_2$S$_3$ requires 512. |
| 79 | MeSO₂— | 4-methyl-5-methyl-3-(1-methylindol-2-yl)-1,2,4-triazole | Mass spectrum (API⁺): Found 510(MH⁺). C$_{26}$H$_{31}$N$_5$O$_2$S$_2$ requires 509. |
| 80 | MeSO₂— | 4-methyl-5-methyl-3-(benzofuran-2-yl)-1,2,4-triazole | Mass spectrum (API⁺): Found 497(MH⁺). C$_{25}$H$_{28}$N$_4$O$_3$S$_2$ requires 496. |
| 81 | MeSO₂— | 4-methyl-5-methyl-3-(indol-5-yl)-1,2,4-triazole | Mass spectrum (API⁺): Found 496(MH⁺). C$_{25}$H$_{29}$N$_5$O$_2$S$_2$ requires 495. |
| 82 | MeSO₂— | 4-methyl-5-methyl-3-(1-methylindol-3-yl)-1,2,4-triazole | Mass spectrum (API⁺): Found 510(MH⁺). C$_{26}$H$_{31}$N$_5$O$_2$S$_2$ requires 509. |
| 83 | MeSO₂— | 4-methyl-5-methyl-3-(indol-4-yl)-1,2,4-triazole | Mass spectrum (API⁺): Found 496(MH⁺). C$_{25}$H$_{29}$N$_5$O$_2$S$_2$ requires 495. |
| 84 | MeSO₂— | 4-methyl-5-methyl-3-[3-(5-methyl-1,2,4-oxadiazol-3-yl)phenyl]-1,2,4-triazole | Mass spectrum (API⁺): Found 539(MH⁺). C$_{26}$H$_{30}$N$_6$O$_3$S$_2$ requires 538. |
| 85 | MeSO₂— | 4-methyl-5-methyl-3-(indol-7-yl)-1,2,4-triazole | Mass spectrum (API⁺): Found 496(MH⁺). C$_{25}$H$_{29}$N$_5$O$_2$S$_2$ requires 495. |

-continued

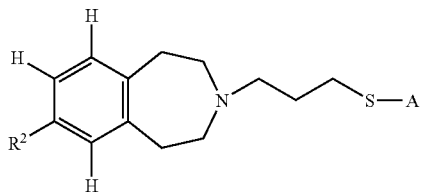

| Example | R² | A | Data |
|---|---|---|---|
| 86 | MeSO₂— | 3-(1,4-dimethyl-4H-1,2,4-triazol-3-yl)-benzo[b]thiophene | Mass spectrum (API⁺): Found 513(MH⁺). C₂₅H₂₈N₄O₂S₃ requires 512. |
| 87 | MeSO₂— | 3-(1,4-dimethyl-4H-1,2,4-triazol-3-yl)-thieno[3,2-b]pyridine | Mass spectrum (API⁺): Found 514(MH⁺). C₂₄H₂₇N₅O₂S₃ requires 513. |
| 88 | MeSO₂— | 4-ethyl-3-methyl-5-phenyl-4H-1,2,4-triazole | Mass spectrum (API⁺): Found 471(MH⁺). C₂₄H₃₀N₄O₂S₂ requires 470. |
| 89 | EtSO₂— | 6-(1,4-dimethyl-4H-1,2,4-triazol-3-yl)-1H-indole | Mass spectrum (API⁺): Found 510(MH⁺). C₂₆H₃₁N₅O₂S₂ requires 509. |
| 90 | EtSO₂— | 5-(1,4-dimethyl-4H-1,2,4-triazol-3-yl)-1H-indole | Mass spectrum (API⁺): Found 510(MH⁺). C₂₆H₃₁N₅O₂S₂ requires 509. |
| 91 | EtSO₂— | 2-(1,4-dimethyl-4H-1,2,4-triazol-3-yl)-thieno[3,2-b]pyridine | Mass spectrum (API⁺): Found 527(MH⁺). C₂₆H₃₀N₄O₂S₃ requires 526. |
| 92 | EtSO₂— | 3-cyclohexyl-1,5-dimethyl-4H-1,2,4-triazole | Mass spectrum (API⁺): Found 477(MH⁺). C₂₄H₃₆N₄O₂S₂ requires 476. |
| 93 | EtSO₂— | 2-(1,4-dimethyl-4H-1,2,4-triazol-3-yl)-1H-indole | Mass spectrum (API⁺): Found 510(MH⁺). C₂₆H₃₁N₅O₂S₂ requires 509. |

-continued

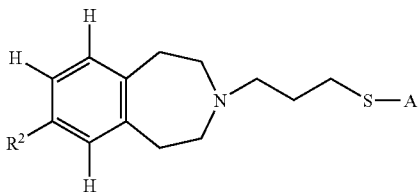

| Example | R² | A | Data |
|---|---|---|---|
| 94 | EtSO₂— | 4,5-dimethyl-4H-1,2,4-triazol-3-yl linked to 2-methylquinolin-6-yl | Mass spectrum (API⁺): Found 536(MH⁺). C₂₈H₃₃N₅O₂S₂ requires 535. |
| 95 | EtSO₂— | 4,5-dimethyl-4H-1,2,4-triazol-3-yl linked to benzofuran-2-yl | Mass spectrum (API⁺): Found 511(MH⁺). C₂₆H₃₀N₄O₃S₂ requires 510. |
| 96 | EtSO₂— | 4,5-dimethyl-4H-1,2,4-triazol-3-yl linked to benzofuran-4-yl | Mass spectrum (API⁺): Found 511(MH⁺). C₂₆H₃₀N₄O₃S₂ requires 510. |
| 97 | EtSO₂— | 1,2-dimethyl-1H-imidazol-5-yl linked to quinolin-6-yl | Mass spectrum (API⁺): Found 521(MH⁺). C₂₈H₃₂N₄O₂S₂ requires 520. |
| 98 | EtSO₂— | 5-methyl-3-phenyl-4H-1,2,4-triazol-3-yl | Mass spectrum (API⁺): Found 457(MH⁺). C₂₃H₂₈N₄O₂S₂ requires 456. |
| 99 | EtSO₂— | 4,5-dimethyl-4H-1,2,4-triazol-3-yl linked to 1-methylindol-2-yl | Mass spectrum (API⁺): Found 524(MH⁺). C₂₇H₃₃N₅O₂S₂ requires 523. |
| 100 | EtSO₂— | 4,5-dimethyl-4H-1,2,4-triazol-3-yl linked to benzofuran-7-yl | Mass spectrum (API⁺): Found 511(MH⁺). C₂₆H₃₀N₄O₃S₂ requires 510. |
| 101 | EtSO₂— | 1,2-dimethyl-1H-imidazol-5-yl linked to 4-fluorophenyl | Mass spectrum (API⁺): Found 488(MH⁺). C₂₅H₃₀FN₃O₂S₂ requires 487. |

-continued

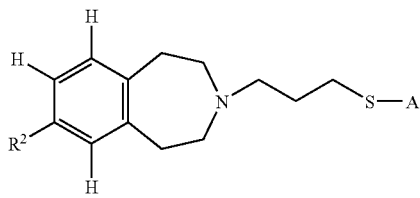

| Example | R² | A | Data |
|---|---|---|---|
| 102 | EtSO₂— | (4-methyl-5-methyl-1,2,4-triazol-3-yl)-1H-indol-3-yl | Mass spectrum (API⁺): Found 510(MH⁺). $C_{26}H_{31}N_5O_2S_2$ requires 509. |
| 103 | EtSO₂— | (4-methyl-5-methyl-1,2,4-triazol-3-yl)-2,4-difluorophenyl | Mass spectrum (API⁺): Found 507(MH⁺). $C_{24}H_{28}F_2N_4O_2S_2$ requires 506. |
| 104 | EtSO₂— | (1,2-dimethylimidazol-5-yl)phenyl | Mass spectrum (API⁺): Found 470(MH⁺). $C_{25}H_{31}N_3O_2S_2$ requires 469. |
| 105 | EtSO₂— | (4-methyl-5-methyl-1,2,4-triazol-3-yl)-3-(3-methylisoxazol-5-yl)phenyl | Mass spectrum (API⁺): Found 552(MH⁺). $C_{28}H_{33}N_5O_3S_2$ requires 551. |
| 106 | EtSO₂— | (4-methyl-5-methyl-1,2,4-triazol-3-yl)benzothiophen-3-yl | Mass spectrum (API⁺): Found 527(MH⁺). $C_{26}H_{30}N_4O_2S_3$ requires 526. |
| 107 | EtSO₂— | (4-methyl-5-methyl-1,2,4-triazol-3-yl)-1H-indol-4-yl | Mass spectrum (API⁺): Found 510(MH⁺). $C_{26}H_{31}N_5O_2S_2$ requires 509. |
| 108 | EtSO₂— | (4-methyl-5-methyl-1,2,4-triazol-3-yl)-3-(pyrazin-2-yl)phenyl | Mass spectrum (API⁺): Found 549(MH⁺). $C_{28}H_{32}N_6O_2S_2$ requires 548. |
| 109 | EtSO₂— | (4-methyl-5-methyl-1,2,4-triazol-3-yl)-1H-indol-7-yl | Mass spectrum (API⁺): Found 510(MH⁺). $C_{26}H_{31}N_5O2S_2$ requires 509. |

-continued

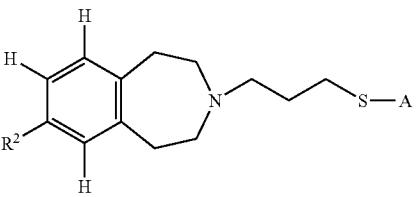

| Example | R² | A | Data |
|---|---|---|---|
| 110 | EtSO₂— | 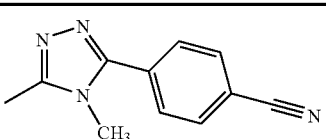 | Mass spectrum (API⁺): Found 496(MH⁺). $C_{25}H_{29}N_5O_2S_2$ requires 495. |
| 111 | EtSO₂— | 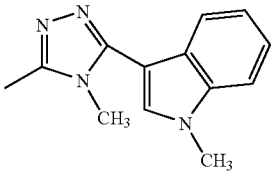 | Mass spectrum (API⁺): Found 524(MH⁺). $C_{27}H_{33}N_5O_2S_2$ requires 523. |
| 112 | EtSO₂— | 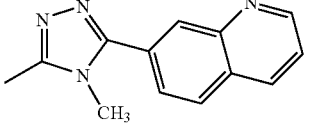 | Mass spectrum (API⁺): Found 522(MH⁺). $C_{27}H_{31}N_5O_2S_2$ requires 521. |
| 113 | EtSO₂— | 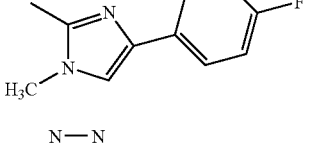 | Mass spectrum (API⁺): Found 488(MH⁺). $C_{25}H_{30}FN_3O_2S_2$ requires 487. |
| 114 | 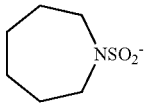 | 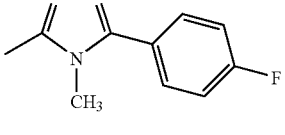 | Mass spectrum (API⁺): Found 558(MH⁺). $C_{28}H_{36}FN_5O_2S_2$ requires 557. |
| 115 | 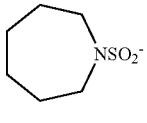 | 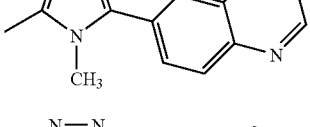 | Mass spectrum (API⁺): Found 591(MH⁺). $C_{31}H_{38}N_6O_2S_2$ requires 590. |
| 116 | 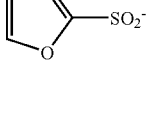 | 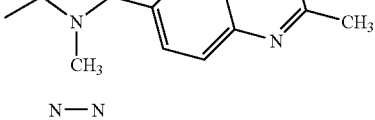 | Mass spectrum (API⁺): Found 574(MH⁺). $C_{30}H_{31}N_5O_3S_2$ requires 573. |
| 117 | 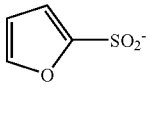 | 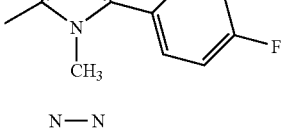 | Mass spectrum (API⁺): Found 527(MH⁺). $C_{26}H_{27}FN_4O_3S_2$ requires 526. |
| 118 | 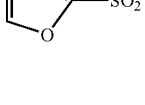 | 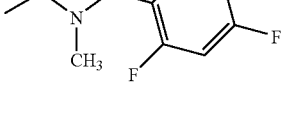 | Mass spectrum (API⁺): Found 545(MH⁺). $C_{26}H_{26}F_2N_4O_3S_2$ requires 544. |

-continued

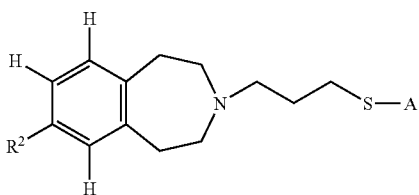

| Example | R² | A | Data |
|---|---|---|---|
| 119 | 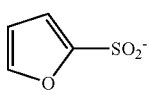 | 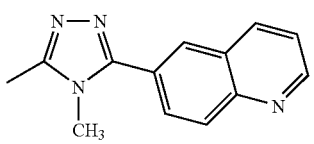 | Mass spectrum (API⁺): Found 560(MH⁺). $C_{29}H_{29}N_5O_3S_2$ requires 559. |
| 120 | MeSO₂O— | 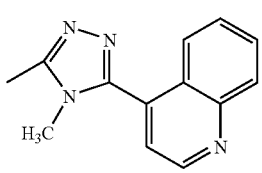 | Mass spectrum (API⁺): Found 524(MH⁺). $C_{26}H_{29}N_5O_3S_2$ requires 523. |
| 121 | 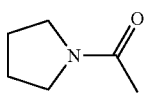 | 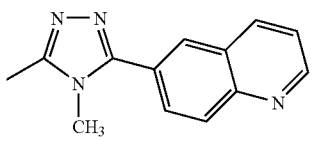 | Mass spectrum (API⁺): Found 527(MH⁺). $C_{30}H_{34}N_6OS$ requires 526. |
| 122 | 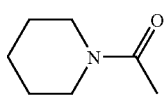 | 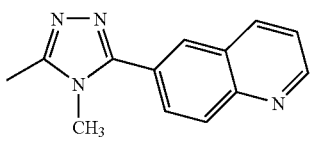 | Mass spectrum (API⁺): Found 541(MH⁺). $C_{31}H_{36}N_6OS$ requires 540. |
| 123 | 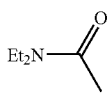 | 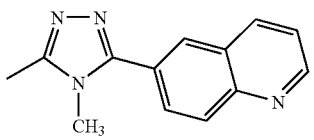 | Mass spectrum (API⁺): Found 529(MH⁺). $C_{30}H_{36}N_6OS$ requires 528. |
| 124 | 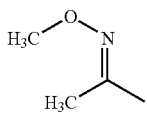 | 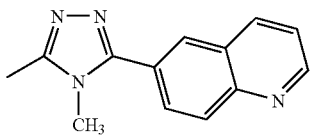 | Mass spectrum (API⁺): Found 501(MH⁺). $C_{28}H_{32}N_6OS$ requires 500. |
| 125 | 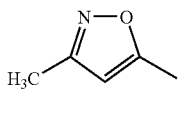 | 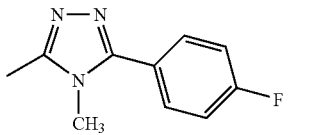 | Mass spectrum (API⁺): Found 478(MH⁺). $C_{26}H_{28}FN_5OS$ requires 477. |
| 126 | 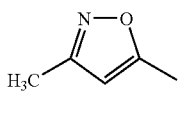 | 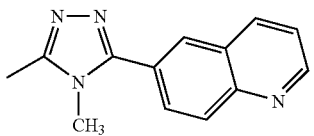 | Mass spectrum (API⁺): Found 511(MH⁺). $C_{29}H_{30}N_6OS$ requires 510. |

-continued

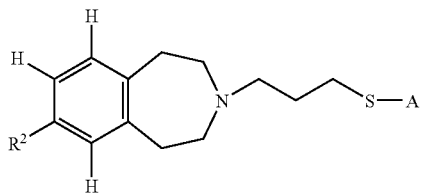

| Example | R² | A | Data |
|---|---|---|---|
| 127 | 3-methylisoxazol-5-yl | 5-(2-methylquinolin-5-yl)-4-methyl-4H-1,2,4-triazol-3-yl | Mass spectrum (API⁺): Found 525(MH⁺). C₃₀H₃₂N₆OS requires 524. |
| 128 | 3-methylisoxazol-5-yl | 5-(2-methylquinolin-6-yl)-4-methyl-4H-1,2,4-triazol-3-yl | Mass spectrum (API⁺): Found 525(MH⁺). C₃₀H₃₂N₆OS requires 524. |
| 129 | 3-methylisoxazol-5-yl | 5-(2,4-difluorophenyl)-4-methyl-4H-1,2,4-triazol-3-yl | Mass spectrum (API⁺): Found 496(MH⁺). C₂₆H₂₇F₂N₅OS requires 495. |
| 130 | 5-methylisoxazol-3-yl | 5-(2-methylquinolin-6-yl)-4-methyl-4H-1,2,4-triazol-3-yl | Mass spectrum (API⁺): Found 525(MH⁺). C₃₀H₃₂N₆OS requires 524. |
| 131 | 5-methylisoxazol-3-yl | 5-(2,4-difluorophenyl)-4-methyl-4H-1,2,4-triazol-3-yl | Mass spectrum (API⁺): Found 496(MH⁺). C₂₆H₂₇F₂N₅OS requires 495. |
| 132 | 5-methylisoxazol-3-yl | 5-(1H-indol-5-yl)-4-methyl-4H-1,2,4-triazol-3-yl | Mass spectrum (API⁺): Found 499(MH⁺). C₂₈H₃₀N₆OS requires 498. |
| 133 | 5-methylisoxazol-3-yl | 5-(2-methylquinolin-5-yl)-4-methyl-4H-1,2,4-triazol-3-yl | Mass spectrum (API⁺): Found 525(MH⁺). C₃₀H₃₂N₆OS requires 524. |
| 134 | 5-methylisoxazol-3-yl | 5-(1H-pyrrolo[2,3-b]pyridin-3-yl)-4-methyl-4H-1,2,4-triazol-3-yl | Mass spectrum (API⁺): Found 500(MH⁺). C₂₇H₂₉N₇OS requires 499. |

-continued

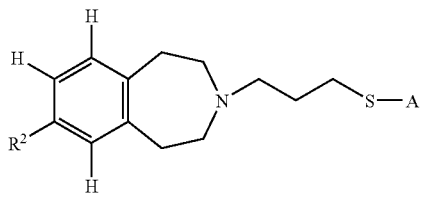

| Example | R² | A | Data |
|---|---|---|---|
| 135 | 5-methyl-3-isoxazolyl | 5-(8-fluoroquinolin-5-yl)-1,4-dimethyl-1,2,4-triazol-3-yl | Mass spectrum (API⁺): Found 529(MH⁺). $C_{29}H_{29}FN_6OS$ requires 528. |
| 136 | 5-methyl-3-isoxazolyl | 5-cyclohexyl-1,4-dimethyl-1,2,4-triazol-3-yl | Mass spectrum (API⁺): Found 466(MH⁺). $C_{26}H_{35}N_5OS$ requires 465. |
| 137 | 5-methyl-3-isoxazolyl | 5-(8-fluoro-2-methylquinolin-5-yl)-1,4-dimethyl-1,2,4-triazol-3-yl | Mass spectrum (API⁺): Found 543(MH⁺). $C_{30}H_{31}FN_6OS$ requires 542. |
| 138 | 5-methyl-3-isoxazolyl | 5-(4-cyanophenyl)-1,4-dimethyl-1,2,4-triazol-3-yl | Mass spectrum (API⁺): Found 485(MH⁺). $C_{27}H_{28}N_6OS$ requires 484. |
| 139 | 5-methyl-3-isoxazolyl | 5-(benzothiophen-2-yl)-1,4-dimethyl-1,2,4-triazol-3-yl | Mass spectrum (API⁺): Found 561(MH⁺). $C_{28}H_{29}N_5OS_2$ requires 515. |
| 140 | 5-methyl-3-isoxazolyl | 5-(1H-indol-6-yl)-1,4-dimethyl-1,2,4-triazol-3-yl | Mass spectrum (API⁺): Found 499(MH⁺). $C_{28}H_{30}N_6OS$ requires 498. |
| 141 | 5-methyl-3-isoxazolyl | 5-(naphthalen-2-yl)-1,4-dimethyl-1,2,4-triazol-3-yl | Mass spectrum (API⁺): Found 510(MH⁺). $C_{30}H_{31}N_5OS$ requires 509. |
| 142 | 5-methyl-3-isoxazolyl | 5-(benzothiophen-3-yl)-1,4-dimethyl-1,2,4-triazol-3-yl | Mass spectrum (API⁺): Found 516(MH⁺). $C_{28}H_{29}N_5OS_2$ requires 515. |

-continued

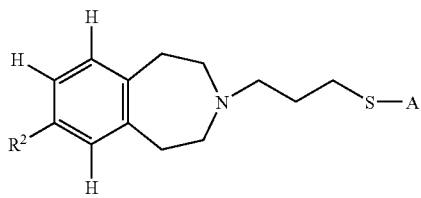

| Example | R² | A | Data |
|---|---|---|---|
| 143 | 5-methyl-3-isoxazolyl | 4-methyl-5-(2,3-dimethylquinoxalin-6-yl)-4H-1,2,4-triazol-3-yl | Mass spectrum (API⁺): Found 540(MH⁺). $C_{30}H_{33}N_7OS$ requires 539. |
| 144 | 5-methyl-3-isoxazolyl | 4-methyl-5-(1H-indol-4-yl)-4H-1,2,4-triazol-3-yl | Mass spectrum (API⁺): Found 499(MH⁺). $C_{28}H_{30}N_6OS$ requires 498. |
| 145 | 5-methyl-3-isoxazolyl | 4-methyl-5-(3-cyanophenyl)-4H-1,2,4-triazol-3-yl | Mass spectrum (API⁺): Found 485(MH⁺). $C_{27}H_{28}N_6OS$ requires 484. |
| 146 | 5-methyl-3-isoxazolyl | 4-methyl-5-(1,6-naphthyridin-2-yl)-4H-1,2,4-triazol-3-yl | Mass spectrum (API⁺): Found 512(MH⁺). $C_{28}H_{29}N_7OS$ requires 511. |
| 147 | 5-methyl-3-isoxazolyl | 4-methyl-5-(benzofuran-4-yl)-4H-1,2,4-triazol-3-yl | Mass spectrum (API⁺): Found 500(MH⁺). $C_{28}H_{29}N_5O_2S$ requires 499. |
| 148 | 5-methyl-3-isoxazolyl | 1-methyl-5-(quinolin-6-yl)-1H-imidazol-2-yl | Mass spectrum (API⁺): Found 510(MH⁺). $C_{30}H_{31}N_5OS$ requires 509. |
| 149 | 5-methyl-3-isoxazolyl | 4-methyl-5-(8-chloro-2-methylquinolin-5-yl)-4H-1,2,4-triazol-3-yl | Mass spectrum (API⁺): Found 559(MH⁺). $C_{30}H_{31}{}^{35}ClN_6OS$ requires 558. |
| 150 | 5-methyl-3-isoxazolyl | 4-methyl-5-(1-methyl-1H-indol-3-yl)-4H-1,2,4-triazol-3-yl | Mass spectrum (API⁺): Found 513(MH⁺). $C_{29}H_{32}N_6OS$ requires 512. |

-continued

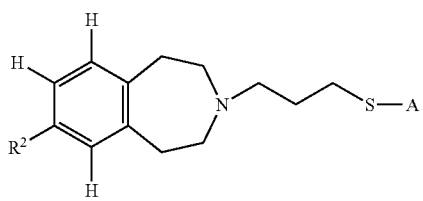

| Example | R² | A | Data |
|---|---|---|---|
| 151 | 5-methyl-isoxazol-3-yl | 5-methyl-4-methyl-1,2,4-triazol-3-yl-benzofuran-2-yl | Mass spectrum (API⁺): Found 500(MH⁺). $C_{28}H_{29}N_5O_2S$ requires 499. |
| 152 | 5-methyl-isoxazol-3-yl | 5-methyl-4-methyl-1,2,4-triazol-3-yl-isoquinolin-1-yl | Mass spectrum (API⁺): Found 511(MH⁺). $C_{29}H_{30}N_6OS$ requires 510. |
| 153 | 5-methyl-isoxazol-3-yl | 5-methyl-4-methyl-1,2,4-triazol-3-yl-isoquinolin-3-yl | Mass spectrum (API⁺): Found 511(MH⁺). $C_{29}H_{30}N_6OS$ requires 510. |
| 154 | 5-methyl-isoxazol-3-yl | 5-methyl-4-methyl-1,2,4-triazol-3-yl-(2-methyl-1,6-naphthyridin-3-yl) | Mass spectrum (API⁺): Found 526(MH⁺). $C_{29}H_{31}N_7OS$ requires 525. |
| 155 | 5-methyl-isoxazol-3-yl | 5-methyl-4-methyl-1,2,4-triazol-3-yl-(1-methyl-indol-2-yl) | Mass spectrum (API⁺): Found 513(MH⁺). $C_{29}H_{32}N_6OS$ requires 512. |
| 156 | 5-methyl-isoxazol-3-yl | 5-methyl-4-methyl-1,2,4-triazol-3-yl-indol-2-yl | Mass spectrum (API⁺): Found 499(MH⁺). $C_{28}H_{30}N_6OS$ requires 498. |
| 157 | 5-methyl-isoxazol-3-yl | 5-methyl-4-methyl-1,2,4-triazol-3-yl-quinolin-2-yl | Mass spectrum (API⁺): Found 511(MH⁺). $C_{29}H_{30}N_6OS$ requires 510. |
| 158 | 5-methyl-isoxazol-3-yl | 5-methyl-4-methyl-1,2,4-triazol-3-yl-quinoxalin-2-yl | Mass spectrum (API⁺): Found 512(MH⁺). $C_{28}H_{29}N_7OS$ requires 511. |
| 159 | 5-methyl-isoxazol-3-yl | 5-methyl-4-methyl-1,2,4-triazol-3-yl-(2,3-dimethylpyridin-5-yl) | Mass spectrum (API⁺): Found 489(MH⁺). $C_{27}H_{32}N_6OS$ requires 488. |

-continued

| Example | R² | A | Data |
|---------|----|---|------|
| 160 | 5-methyl-3-isoxazolyl | 5-methyl-4-methyl-3-(1-naphthyl)-4H-1,2,4-triazol-3-yl | Mass spectrum (API⁺): Found 510(MH⁺). C₃₀H₃₁N₅OS requires 509. |
| 161 | 5-methyl-3-isoxazolyl | 5-methyl-4-methyl-3-(2-oxo-1,2-dihydroquinolin-6-yl)-4H-1,2,4-triazol-3-yl | Mass spectrum (API⁺): Found 527(MH⁺). C₂₉H₃₀N₆O₂S requires 526. |
| 162 | 5-methyl-3-isoxazolyl | 5-methyl-4-methyl-3-(benzofuran-7-yl)-4H-1,2,4-triazol-3-yl | Mass spectrum (API⁺): Found 500(MH⁺). C₂₈H₂₉N₅O₂S requires 499. |
| 163 | 5-methyl-3-isoxazolyl | 5-methyl-4-methyl-3-(quinoxalin-6-yl)-4H-1,2,4-triazol-3-yl | Mass spectrum (API⁺): Found 512(MH⁺). C₂₈H₂₉N₇OS requires 511. |
| 164 | 5-methyl-3-isoxazolyl | 5-methyl-4-methyl-3-(quinolin-8-yl)-4H-1,2,4-triazol-3-yl | Mass spectrum (API⁺): Found 511(MH⁺). C₂₉H₃₀N₆OS requires 510. |
| 165 | 5-methyl-3-isoxazolyl | 5-methyl-4-methyl-3-(2,3-dimethylpyridin-5-yl)-4H-1,2,4-triazol-3-yl | Mass spectrum (API⁺): Found 489(MH⁺). C₂₇H₃₂N₆OS requires 488. |
| 166 | 3-pyrazinyl | 5-methyl-4-methyl-3-(2-methylquinolin-6-yl)-4H-1,2,4-triazol-3-yl | Mass spectrum (API⁺): Found 544(MNa⁺). C₃₀H₃₁N₇S requires 521. |
| 167 | 3-pyrazinyl | 5-methyl-4-methyl-3-(2-methylquinolin-6-yl)-4H-1,2,4-triazol-3-yl | Mass spectrum (API⁺): Found 544(MNa⁺). C₃₀H₃₁N₇S requires 521. |

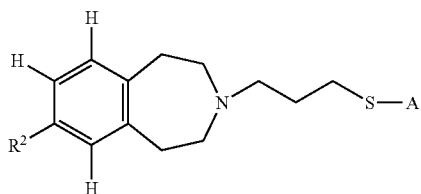

| Example | R² | A | Data |
|---|---|---|---|
| 168 | 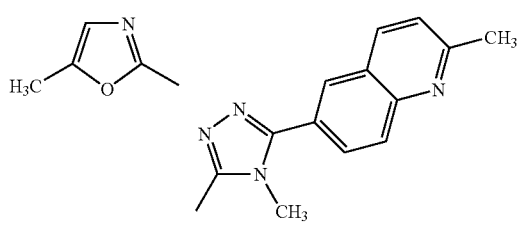 | | Mass spectrum (API⁺): Found 525(MH⁺). $C_{30}H_{32}N_6OS$ requires 524. |
| 169 | 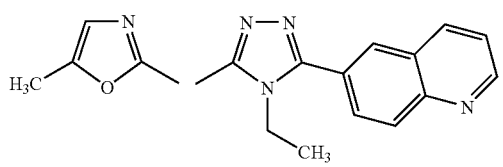 | | Mass spectrum (API⁺): Found 525(MH⁺). $C_{30}H_{32}N_6OS$ requires 524. |
| 170 | 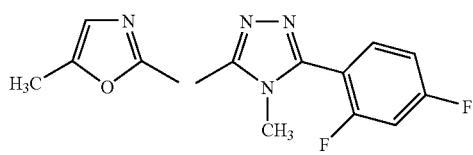 | | Mass spectrum (API⁺): Found 496(MH⁺). $C_{26}H_{27}F_2N_5OS$ requires 495. |
| 171 | 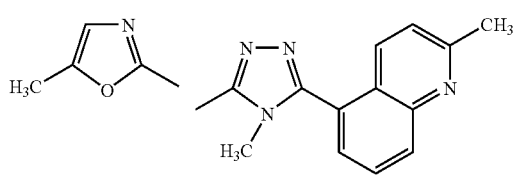 | | Mass spectrum (API⁺): Found 525(MH⁺). $C_{30}H_{32}N_6OS$ requires 524. |
| 172 | 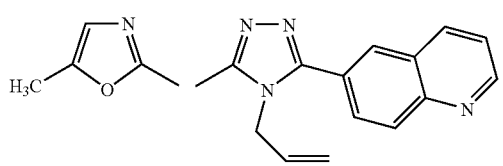 | | Mass spectrum (API⁺): Found 537(MH⁺). $C_{31}H_{32}N_6OS$ requires 536. |

Example 173

7-(5-Methyl-3-isoxazolyl)-3-{4-[4-methyl-5-(2-methyl-6-quinolinyl)-4H-1,2,4-triazol-3-yl]butyl}-2,3,4,5-tetrahydro-1H-3-benzazepine hydrochloride

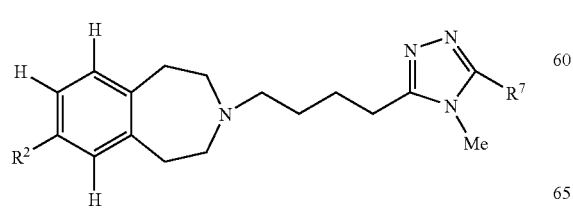

a) 4-[1,3]Dioxan-2-yl-butyric acid methyl ester

Methyl 5,5-dimethoxyvalerate (20.0 g, 0.114 mol), propane-1,3-diol (13 g, 0.17 mol) and para-toluene sulphonic acid (2.17 g, 0.0114 mol) were heated under Dean-Stark conditions in toluene (100 ml) for 4 h. The mixture was cooled to room temperature and diluted with diethyl ether (100 ml) and then neutralized with solid sodium bicarbonate. The solid was filtered and the filtrate evaporated to give a pale yellow oil (22.3 g). A 10 g portion of this was then purified by silica gel chromatography (eluent 30% EtOAc:hexane) which gave the title compound as a colourless oil (6.82 g).

b) 4-[1,3]Dioxan-2-yl-butyric acid

4-[1,3]Dioxan-2-yl-butyric acid methyl ester (6.8 g, 0.036 mol) was added to a stirred solution of sodium hydroxide (1.87 g, 0.047 mol) in water (30 ml) and methanol (30 ml). The mixture was stirred for 18 h at room temperature and then the solvent evaporated. The residue was partitioned between ethyl acetate (100 ml) and water (100 ml) and cooled to 0° C. The mixture was acidified with hydrochloric acid (1M) to pH 2 and the layers separated. The aqueous layer was further extracted with cold ethyl acetate (100 ml) and the combined organic layers washed with brine (100 ml) and then dried ($Na_2SO_4$). The solvents were evaporated and the crude solid (5.56 g) was used in the next step.

c) 4-[1,3] Dioxan-2-yl-N-methyl-butyramide

To 4-[1,3]dioxan-2-yl-butyric acid (2.55 g, 0.015 mol) in dichloromethane (200 ml) was added methylamine (2M in THF, 8.1 ml, 0.016 mol), 1-(3-dimethylaminopropyl)-3-ethylcarbodiimide hydrochloride (3.09 g, 0.016 mol) and hydroxybenzotriazole (2.16 g, 0.016 mol) and the mixture stirred at room temperature overnight. The organic layer was washed with saturated sodium bicarbonate solution (200 ml) and the aqueous layer extracted with dichloromethane (4×50 ml). The combined organics were dried ($Na_2SO_4$) and evaporated to give a colourless oil (3.2 g)

Mass Spectrum $AP^+$: Found 188 ($[MH]^+$). $C_9H_{17}NO_3$ requires 187.

d) 2-Methyl-quinoline-6-carboxylic acid N'-(4-[1,3] dioxan-2-yl-1-methylimino-butyl)-hydrazide 4-[1,3]Dioxan-2-yl-N-methyl-butyramide (1 g, 5.35 mmol) was cooled to −78° C. in dry dichloromethane (10 ml) under argon and phosphorus oxychloride (0.65 ml, 7 mmol) was added dropwise. The mixture was warmed to room temperature to give an amber solution which was re-cooled to 0° C. This solution was added dropwise to a suspension of 2-methyl-quinoline-6-carboxylic acid hydrazide (1 g, 5 mmol) in chloroform (20 ml) and the mixture stirred at room temperature overnight. The mixture was poured into water (300 ml), basified with sodium hydroxide solution (5M) and extracted with dichloromethane (3×200 ml). The combined organic portions were dried ($Na_2SO_4$), filtered and evaporated to give the desired compound as a brown oil (1.28 g, 83%).

Mass Spectrum $AP^-$: Found 369 ($[M–H]^-$). $C_{20}H_{26}N_4O_3$ requires 370.

e) 6-[5-(3-[1,3] Dioxan-2-yl-propyl)-4-methyl-4H-[1,2,4] triazol-3-yl]-2-methyl-quinoline 2-Methyl-quinoline-6-carboxylic acid N'-(4-[1,3] dioxan-2-yl-1-methylimino-butyl)-hydrazide (1.28 g, 3.4 mmol) was heated in ethyl acetate (20 ml) for 4 h. The solvent was evaporated and the residue was purified by silica gel chromatography (eluent 20% MeOH:EtOAc) which gave the title compound as a brown solid (109 mg, 10%).

Mass Spectrum $AP^+$: Found 353 ($[MH]^+$). $C_{20}H_{24}N_4O_2$ requires 352.

f) 4-[4-Methyl-5-(2-methyl-quinolin-6-yl)-4H-[1,2,4] triazol-3-yl]-butyraldehyde 6-[5-(3-[1,3]Dioxan-2-yl-propyl)-4-methyl-4H-[1,2,4] triazol-3-yl]-2-methyl-quinoline (109 mg, 0.31 mmol) was heated in water (20 ml) and concentrated sulphuric acid (0.5 ml) at 100° C. for 3 h. The mixture was cooled to room temperature, basified with solid sodium bicarbonate and extracted with dichloromethane (3×50 ml). The combined organic portions were dried ($Na_2SO_4$), filtered and evaporated to give the desired compound as an off-white solid (76 mg, 84%).

Mass Spectrum $AP^+$: Found 295 ($[MH]^+$). $C_{17}H_{18}N_4O$ requires 294.

g) 7-(5-Methyl-isoxazol-3-yl)-3-{4-[4-methyl-5-(2-methyl-quinolin-6-yl)-4H-[1,2,4] triazol-3-yl]-butyl}-2,3,4,5-tetrahydro-1H-benzo[d] azepine 4-[4-Methyl-5-(2-methyl-quinolin-6-yl)-4H-[1,2,4]triazol-3-yl]-butyraldehyde (76 mg, 0.25 mmol) and 7-(5-Methyl-isoxazol-3-yl)-2,3,4,5-tetrahydro-1H-benzo[d]azepine (55 mg, 0.24 mmol) were stirred at room temperature in dichloromethane (5 ml) for 30 min. Sodium triacetoxyborohydride (55 mg, 0.26 mmol) was then added and the mixture stirred over the weekend. The mixture was diluted with dichloromethane (50 ml) and washed with saturated sodium bicarbonate solution (30 ml). The aqueous was extracted with further dichloromethane (50 ml) and the combined organic portions were dried ($Na_2SO_4$), filtered and evaporated to give the desired compound as an off-white solid (26 mg).

Mass Spectrum $AP^+$: Found 507 ($[MH]^+$). $C_{31}H_{34}N_6O$ requires 506.

$^1$H NMR ($CDCl_3$) δ: 1.72 (2H, m), 1.93 (2H, m), 2.46 (3H, s), 2.57 (3H, t, J=7 Hz), 2.66 (4H, m), 2.79 (3H, s), 2.91 (6H, m), 3.64 (3H, s), 6.26 (1H, s), 7.16 (1H, d, J=8 Hz), 7.37 (1H, d, J=9 Hz), 7.49 (1H, dd, J=2, 8 Hz), 7.54 (1H, s), 7.89 (1H, dd, J=2, 9 Hz), 8.11 (3H, m).

The following compound was prepared in a similar manner to example 173:

Example 174

3-{4-[5-(4-Fluorophenyl)-4-methyl-4H-1,2,4-triazol-3-yl]butyl}-7-(5-methyl-3-isoxazolyl)-2,3,4,5-tetrahydro-1H-3-benzazepine Mass spectrum ($API^+$): Found 460 ($MH^+$). $C_{27}H_{30}N_5OF$ requires 459.

Example 175

7-(Ethylsulfonyl)-3-(4-{[4-methyl-5-(6-quinolinyl)-4H-1,2,4-triazol-3-yl]thio}butyl)-2,3,4,5-tetrahydro-1H-3-benzazepine a) 6-{5-[3-(5,5-Dimethyl-[1,3] dioxan-2-yl)-propylsulfanyl]-4-methyl-4H-[1,2,4] triazol-3-yl}-quinoline 4-Methyl-5-quinolin-6-yl-4H-[1,2,4]triazole-3-thiol (0.5 g, 2.07 mmol), 2-(3-Bromo-propyl)-5,5-dimethyl-[1,3]dioxane (0.49 g, 2.07 mmol) and lithium hydroxide (50 mg) were heated in dimethylformamide at 100° C. for 3 h. The mixture was cooled and partitioned between water (80 ml) and ethyl acetate (100 ml). The layers were separated and the aqueous re-extracted with ethyl acetate (100 ml). The combined organic portions were washed with brine (100 ml) and then dried ($Na_2SO_4$), filtered and evaporated to give a colourless oil. Purification by silica gel chromatography (eluent EtOAc—10% MeOH:EtOAc) which gave the title compound as a colourless solid (0.53 g, 65%).

Mass Spectrum AP$^+$: Found 399 ([MH]$^+$). $C_{21}H_{26}N_4SO_2$ requires 398.

b) 4-(4-Methyl-5-quinolin-6-yl-4H-[1,2,4]triazol-3-ylsulfanyl)-butyraldehyde

6-{5-[3-(5,5-Dimethyl-[1,3]dioxan-2-yl)-propylsulfanyl]-4-methyl-4H-[1,2,4]triazol-3-yl}-quinoline (0.51 g, 1.28 mmol) was heated in water (30 ml) and sulphuric acid (1.92 mmol) at 100° C. for 3 h. The mixture was cooled and basified with sodium carbonate. The aqueous mixture was extracted with dichloromethane (3×50 ml) and the combined organic portions were dried ($Na_2SO_4$), filtered and evaporated to give the title compound as a colourless oil (0.38 g, 95%).

Mass Spectrum AP$^+$: Found 313 ([MH]$^+$). $C_{16}H_{16}N_4SO$ requires 312.

c) 7-(Ethylsulfonyl)-3-(4-{[4-methyl-5-(6-quinolinyl)-4H-1,2,4-triazol-3-yl]thio}butyl)-2,3,4,5-tetrahydro-1H-3-benzazepine 4-(4-Methyl-5-quinolin-6-yl-4H-[1,2,4]triazol-3-ylsulfanyl)-butyraldehyde (0.1 g, 0.32 mmol) and 7-Ethanesulfonyl-2,3,4,5-tetrahydro-1H-benzo[d]azepine (0.11 g, 0.45 mmol) were stirred at room temperature in dichloromethane (4 ml) for 20 min. Sodium triacetoxyborohydride (71 mg, 0.34 mmol) was then added and the mixture stirred overnight. The mixture was diluted with dichloromethane (50 ml) and washed with saturated sodium bicarbonate solution (30 ml). The aqueous was extracted with further dichloromethane (50 ml) and the combined organic portions were dried ($Na_2SO_4$), filtered and evaporated to give a yellow oil. Purification by silica gel chromatography (eluent 10% MeOH:EtOAc) which gave the title compound as a colourless oil (35 mg, 21%).

Mass Spectrum AP$^+$: Found 536 ([MH]$^+$). $C_{28}H_{33}N_5S_2O_2$ requires 535.

$^1$H NMR (CDCl$_3$) δ: 1.28 (3H, t, J=7 Hz), 1.71 (2H, m), 1.90 (2H, m), 2.54 (2H, t, J=7 Hz), 2.65 (4H, m), 2.99 (4H, m), 3.10 (2H, t, 7 Hz), 3.37 (2H, t, J=7 Hz), 3.69 (3H, s), 7.26 (1H, d, J=8 Hz), 7.50 (1H, m), 7.61 (1H, s), 7.64 (1H, d, J=8 Hz), 7.97 (1H, d, J=8 Hz), 8.16 (1H, s), 8.24 (2H, d, J=9 Hz), 9.00 (1H, m).

The following compounds were prepared in a similar manner to Description 175:

Example 176

7-(5-Methyl-3-isoxazolyl)-3-(4-{[4-methyl-5-(6-quinolinyl)-4H-1,2,4-triazol-3-yl]thio}butyl)-2,3,4,5-tetrahydro-1H-3-benzazepine Mass Spectrum AP$^+$: Found 525 ([MH]$^+$). $C_{30}H_{32}N_6SO$ requires 524.

Example 177

7-(3-Methyl-5-isoxazolyl)-3-(4-{[4-methyl-5-(6-quinolinyl)-4H-1,2,4-triazol-3-yl]thio}butyl)-2,3,4,5-tetrahydro-1H-3-benzazepine Mass Spectrum AP$^+$: Found 525 ([MH]$^+$). $C_{30}H_{32}N_6SO$ requires 524.

The invention claimed is:

1. A compound of formula (I)

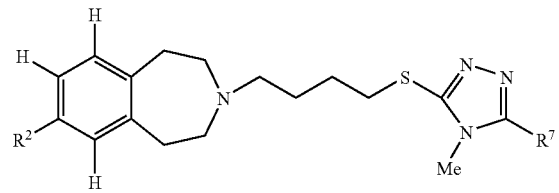

wherein $R^2$ is $C_{1-4}$alkylthio, $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group; or a group $R^5OCO(CH_2)_p$, $R^5CON(R^6)(CH_2)_p$, $R^5R^6NCO(CH_2)_p$ or $R^5R^6NSO_2(CH_2)_p$, in which p is zero or an integer from 1 to 4, and each of $R^5$ and $R^6$ independently are hydrogen or a $C_{1-4}$alkyl group, or, in groups $R^5CON(R^6)(CH_2)_p$, $R^5R^6NCO(CH_2)_p$ and $R^5R^6NSO_2(CH_2)_p$, $R^5CONR^6$ or $R^5R^6N$ together form a 4-, 5-, 6- or 7-membered azacyclic group optionally containing one additional O, N or S atom in the azacycle and having 3-8 carbon atoms; or a group $Ar^3$—Z, wherein $Ar^3$ is an optionally substituted phenyl ring or an optionally substituted 5- or 6-membered aromatic heterocyclic ring and Z is a bond, O, S, $SO_2$, or $CH_2$;

$R^7$ is quinolinyl, unsubstituted or substituted by one or more substituents selected from the group consisting of halo, hydroxyl, oxo, cyano, nitro, $C_{1-4}$alkyl, $C_{1-4}$alkoxy, $C_{1-4}$alkylenedioxy, $C_{1-4}$alkanoyl, $C_{1-4}$alkylsulfonyl, $C_{1-4}$alkylsulfonyloxy, $C_{1-4}$alkylsulfinyl, $C_{1-4}$alkylthio, $R^{13}SO_2N(R^{14})$—, $R^{13}R^{14}NSO_2$—, $R^{13}R^{14}N$, $R^{13}R^{14}NCO$—, or $R^{13}CON(R^{14})$— where in each of $R^{13}$ and $R^{14}$ independently are hydrogen or $C_{1-4}$alkyl, or $R^{13}R^{14}$ together form a $C_{3-6}$ alkylene chain;

$R^{10}$ is H or $C_{1-4}$alkyl;

or a salt thereof.

2. A compound according to claim 1 wherein:

$R^2$ is $C_{1-4}$alkylsulfonyl; $C_{1-4}$alkylsulfonyloxy; $R^5R^6NSO_2$ group where each of $R^5$ and $R^6$ independently represents a hydrogen atom or a $C_{1-4}$alkyl group, or $R^5R^6N$ together form a 4-, 5-, 6- or 7-membered azacyclic group optionally containing one additional O, N or S atom in the azacycle and having 3-8 carbon atoms; or a group $Ar^3Z$, where Z is a bond and $Ar^3$ is an optionally substituted 5- or 6-membered heterocyclic aromatic ring;

or a pharmaceutically acceptable salt thereof.

3. A compound according to claim 1 which is:

3-(3-{[4-methyl-5-(6-quinolinyl)-4H-1,2,4-triazol-3-yl]thio} propyl)-7-(methylsulfonyl)-2,3,4,5-tetrahydro-1H-3-benzazepine;

3-(3-{[4-methyl-5-(6-quinolinyl)-4H-1,2,4-triazol-3-yl]thio}propyl)-2,3,4,5-tetrahydro-1H-3-benzazepin-7-yl methanesulfonate;

3-(3-{[4-methyl-5-(2-methyl-5-quinolinyl)-4H-1,2,4-triazol-3-yl]thio} propyl)-2,3,4,5-tetrahydro-1H-3-benzazepin-7-yl methanesulfonate;

3-(3-{[4-methyl-5-(3-quinolinyl)-4H-1,2,4-triazol-3-yl]thio}propyl)-2,3,4,5-tetrahydro-1H-3-benzazepin-7-yl methanesulfonate;

7-(ethylsulfonyl)-3-(3-{[4-methyl-5-(6-quinolinyl)-4H-1,2,4-triazol-3-yl]thio}propyl)-2,3,4,5-tetrahydro-1H-3-benzazepine;

3-(3-{[4-methyl-5-(6-quinolinyl)-4H-1,2,4-triazol-3-yl]thio} propyl)-7-(1-pyrrolidinylsulfonyl)-2,3,4,5-tetrahydro-1H-3-benzazepine;

3-(3-{[4-methyl-5-(6-quinolinyl)-4H-1,2,4-triazol-3-yl]thio} propyl)-7-(2-pyrazinyl)-2,3,4,5-tetrahydro-1H-3-benzazepine;

N,N-dimethyl-3-(3-{[4-methyl-5-(6-quinolinyl)-4H-1,2,4-triazol-3-yl]thio} propyl)-2,3,4,5-tetrahydro-1H-3-benzazepine-7-sulfonamide;

3-(3-{[4-methyl-5-(4-quinolinyl)-4H-1,2,4-triazol-3-yl]thio} propyl)-7-(methylsulfonyl)-2,3,4,5-tetrahydro-1H-3-benzazepine;

7-(ethylsulfonyl)-3-(3-{[4-methyl-5-(2-methyl-5-quinolinyl)-4H-1,2,4-triazol-3-yl]thio}propyl)-2,3,4,5-tetrahydro-1H-3-benzazepine;

7-(5-methyl-1,3-oxazol-2-yl)-3-(3-{[4-methyl-5-(6-quinolinyl)-4H-1,2,4-triazol-3-yl]thio}propyl)-2,3,4,5-tetrahydro-1H-3-benzazepine;

7-(5-methyl-3-isoxazolyl)-3-(3-{[4-methyl-5-(6-quinolinyl)-4H-1,2,4-triazol-3-yl]thio}propyl)-2,3,4,5-tetrahydro-1H-3-benzazepine;

3-(3-{[4-methyl-5-(6-quinolinyl)-4H-1,2,4-triazol-3-yl]thio} propyl)-7-(1-piperidinylsulfonyl)-2,3,4,5-tetrahydro-1H-3-benzazepine;

3-(3-{[4-methyl-5-(6-quinolinyl)-4H-1,2,4-triazol-3-yl]thio} propyl)-7-(phenylsulfonyl)-2,3,4,5-tetrahydro-1H-3-benzazepine;

3-(3-{[4-methyl-5-(2-methyl-6-quinolinyl)-4H-1,2,4-triazol-3-yl]thio} propyl)-7-(methylsulfonyl)-2,3,4,5-tetrahydro-1H-3-benzazepine;

7-(ethylsulfonyl)-3-(3-{[4-methyl-5-(2-methyl-6-quinolinyl)-4H-1,2,4-triazol-3-yl]thio}propyl)-2,3,4,5-tetrahydro-1H-3-benzazepine;

7-(hexahydro-1H-azepin-1-ylsulfonyl)-3-(3-{[4-methyl-5-(6-quinolinyl)-4H-1,2,4-triazol-3-yl]thio}propyl)-2,3,4,5-tetrahydro-1H-3-benzazepine;

7-(2-furanylsulfonyl)-3-(3-{[4-methyl-5-(6-quinolinyl)-4H-1,2,4-triazol-3-yl]thio}propyl)-2,3,4,5-tetrahydro-1H-3-benzazepine;

3-(3-{[4-methyl-5-(4-quinolinyl)-4H-1,2,4-triazol-3-yl]thio}propyl)-2,3,4,5-tetrahydro-1H-3-benzazepin-7-yl methanesulfonate;

3-(3-{[4-methyl-5-(6-quinolinyl)-4H-1,2,4-triazol-3-yl]thio} propyl)-7-(1-pyrrolidinylcarbonyl)-2,3,4,5-tetrahydro-1H-3-benzazepine;

3-(3-{[4-methyl-5-(6-quinolinyl)-4H-1,2,4-triazol-3-yl]thio} propyl)-7-(1-piperidinylcarbonyl)-2,3,4,5-tetrahydro-1H-3-benzazepine;

N,N-diethyl-3-(3-{[4-methyl-5-(6-quinolinyl)-4H-1,2,4-triazol-3-yl]thio} propyl)-2,3,4,5-tetrahydro-1H-3-benzazepine-7-carboxamide;

7-(3-methyl-5-isoxazolyl)-3-(3-{[4-methyl-5-(6-quinolinyl)-4H-1,2,4-triazol-3-yl]thio}propyl)-2,3,4,5-tetrahydro-1H-3-benzazepine;

7-(3-methyl-5-isoxazolyl)-3-(3-{[4-methyl-5-(2-methyl-5-quinolinyl)-4H-1,2,4-triazol-3-yl]thio}propyl)-2,3,4,5-tetrahydro-1H-3-benzazepine;

7-(3-methyl-5-isoxazolyl)-3-(3-{[4-methyl-5-(2-methyl-6-quinolinyl)-4H-1,2,4-triazol-3-yl]thio}propyl)-2,3,4,5-tetrahydro-1H-3-benzazepine;

7-(5-methyl-3-isoxazolyl)-3-(3-{[4-methyl-5-(2-methyl-6-quinolinyl)-4H-1,2,4-triazol-3-yl]thio}propyl)-2,3,4,5-tetrahydro-1H-3-benzazepine;

7-(5-methyl-3-isoxazolyl)-3-(3-{[4-methyl-5-(2-methyl-5-quinolinyl)-4H-1,2,4-triazol-3-yl]thio}propyl)-2,3,4,5-tetrahydro-1H-3-benzazepine;

3-(3-{[5-(8-fluoro-5-quinolinyl)-4-methyl-4H-1,2,4-triazol-3-yl]thio} propyl)-7-(5-methyl-3-isoxazolyl)-2,3,4,5-tetrahydro-1H-3-benzazepine;

3-(3-{[5-(8-fluoro-2-methyl-5-quinolinyl)-4-methyl-4H-1,2,4-triazol-3-yl]thio}propyl)-7-(5-methyl-3-isoxazolyl)-2,3,4,5-tetrahydro-1H-3-benzazepine;

3-(3-{[5-(8-chloro-2-methyl-5-quinolinyl)-4-methyl-4H-1,2,4-triazol-3-yl]thio}propyl)-7-(5-methyl-3-isoxazolyl)-2,3,4,5-tetrahydro-1H-3-benzazepine;

7-(5-methyl-3-isoxazolyl)-3-(3-{[4-methyl-5-(2-quinolinyl)-4H-1,2,4-triazol-3-yl]thio}propyl)-2,3,4,5-tetrahydro-1H-3-benzazepine;

5-[4-methyl-5-({3-[7-(5-methyl-3-isoxazolyl)-1,2,4,5-tetrahydro-3H-3-benzazepin-3-yl]propyl}thio)-4H-1,2,4-triazol-3-yl]-2(1H)-quinolinone;

7-(5-methyl-3-isoxazolyl)-3-(3-{[4-methyl-5-(8-quinolinyl)-4H-1,2,4-triazol-3-yl]thio}propyl)-2,3,4,5-tetrahydro-1H-3-benzazepine;

3-(3-{[4-methyl-5-(2-methyl-6-quinolinyl)-4H-1,2,4-triazol-3-yl]thio} propyl)-7-(2-pyrazinyl)-2,3,4,5-tetrahydro-1H-3-benzazepine;

3-(3-{[4-methyl-5-(2-methyl-5-quinolinyl)-4H-1,2,4-triazol-3-yl]thio} propyl)-7-(2-pyrazinyl)-2,3,4,5-tetrahydro-1H-3-benzazepine;

3-(3-{[4-methyl-5-(2-methyl-6-quinolinyl)-4H-1,2,4-triazol-3-yl]thio} propyl)-7-(5-methyl-1,3-oxazol-2-yl)-2,3,4,5-tetrahydro-1H-3-benzazepine;

3-(3-{[4-ethyl-5-(6-quinolinyl)-4H-1,2,4-triazol-3-yl]thio} propyl)-7-(5-methyl-1,3-oxazol-2-yl)-2,3,4,5-tetrahydro-1H-3-benzazepine;

3-(3-{[4-methyl-5-(2-methyl-5-quinolinyl)-4H-1,2,4-triazol-3-yl]thio} propyl)-7-(5-methyl-1,3-oxazol-2-yl)-2,3,4,5-tetrahydro-1H-3-benzazepine;

or a hydrochloride salt thereof, or another pharmaceutically acceptable salt thereof.

4. A pharmaceutical composition comprising a compound of formula (I) as defined in claim 1, or a pharmaceutically acceptable salt thereof, and a pharmaceutically acceptable carrier.

5. A method of treating schizophrenia which comprises administering to a mammal in need thereof an effective amount of a compound of formula (I) according to claim 1, or a pharmaceutically acceptable salt thereof.

6. A compound which is 7-(ethylsulfonyl)-3-(4-{[4-methyl-5-(6-quinolinyl)-4H-1,2,4-triazol-3-yl]thio} butyl)-2,3,4,5-tetrahydro-1H-3-benzazepine;

7-(5-methyl-3-isoxazolyl)-3-(4-{[4-methyl-5-(6-quinolinyl)-4H-1,2,4-triazol-3-yl]thio} butyl)-2,3,4,5-tetrahydro-1H-3-benzazepine;

7-(3-methyl-5-isoxazolyl)-3-(4-{[4-methyl-5-(6-quinolinyl)-4H-1,2,4-triazol-3-yl]thio} butyl)-2,3,4,5-tetrahydro-1H-3-benzazepine;

or a hydrochloride salt thereof, or another pharmaceutically acceptable salt thereof.

7. A compound which is:

3-(3-{[5-(1-isoquinolinyl)-4-methyl-4H-1,2,4-triazol-3-yl]thio} propyl)-7-(5-methyl-3-isoxazolyl)-2,3,4,5-tetrahydro-1H-3-benzazepine;

3-(3-{[5-(3-isoquinolinyl)-4-methyl-4H-1,2,4-triazol-3-yl]thio} propyl)-7-(5-methyl-3-isoxazolyl)-2,3,4,5-tetrahydro-1H-3-benzazepine;

or a hydrochloride salt thereof, or another pharmaceutically acceptable salt thereof.

8. A compound which is:

3-(3-{[1-methyl-5-(6-quinolinyl)-1H-imidazol-2-yl]thio} propyl)-7-(4-morpholinylsulfonyl)-2,3,4,5-tetrahydro-1H-3-benzazepine;

7-(ethylsulfonyl)-3-(3-{[1-methyl-5-(6-quinolinyl)-1H-imidazol-2-yl]thio} propyl)-2,3,4,5-tetrahydro-1H-3-benzazepine;

7-(5-methyl-3-isoxazolyl)-3-(3-{[1-methyl-5-(6-quinolinyl)-1H-imidazol-2-yl]thio}propyl)-2,3,4,5-tetrahydro-1H-3-benzazepine;

7-(5-methyl-3-isoxazolyl)-3-(3-{[4-methyl-5-(6-quinoxalinyl)-4H-1,2,4-triazol-3-yl]thio}propyl)-2,3,4,5-tetrahydro-1H-3-benzazepine;

7-(5-methyl-1,3-oxazol-2-yl)-3-(3-{[4-(2-propen-1-yl)-5-(6-quinolinyl)-4H-1,2,4-triazol-3-yl]thio}propyl)-2,3,4,5-tetrahydro-1H-3-benzazepine;

7-(5-methyl-3-isoxazolyl)-3-{4-[4-methyl-5-(2-methyl-6-quinolinyl)-4H-1,2,4-triazol-3-yl]butyl}-2,3,4,5-tetrahydro-1H-3-benzazepine;

7-(ethylsulfonyl)-3-(4-{[4-methyl-5-(6-quinolinyl)-4H-1,2,4-triazol-3-yl]thio} butyl)-2,3,4,5-tetrahydro-1H-3-benzazepine;

7-(5-methyl-3-isoxazolyl)-3-(4-{[4-methyl-5-(6-quinolinyl)-4H-1,2,4-triazol-3-yl]thio} butyl)-2,3,4,5-tetrahydro-1H-3-benzazepine;

7-(3-methyl-5-isoxazolyl)-3-(4-{[4-methyl-5-(6-quinolinyl)-4H-1,2,4-triazol-3-yl]thio} butyl)-2,3,4,5-tetrahydro-1H-3-benzazepine;

or a hydrochloride salt thereof, or another pharmaceutically acceptable salt thereof.

\* \* \* \* \*